US012102676B2

(12) United States Patent
Amanna et al.

(10) Patent No.: US 12,102,676 B2
(45) Date of Patent: *Oct. 1, 2024

(54) INACTIVATING PATHOGENS AND PRODUCING HIGHLY IMMUNOGENIC INACTIVATED VACCINES USING A DUAL OXIDATION PROCESS

(71) Applicant: Najít Technologies, Inc., Beaverton, OR (US)

(72) Inventors: Ian J. Amanna, Hillsboro, OR (US); Elizabeth A. Poore, Portland, OR (US)

(73) Assignee: Najít Technologies, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/136,808

(22) Filed: Apr. 19, 2023

(65) Prior Publication Data

US 2023/0346910 A1 Nov. 2, 2023

Related U.S. Application Data

(60) Continuation of application No. 17/497,810, filed on Oct. 8, 2021, now Pat. No. 11,633,470, which is a division of application No. 16/300,540, filed as application No. PCT/US2017/032030 on May 10, 2017, now Pat. No. 11,141,475.

(60) Provisional application No. 62/334,588, filed on May 11, 2016, provisional application No. 62/334,357, filed on May 10, 2016, provisional application No. 62/334,406, filed on May 10, 2016.

(51) Int. Cl.
| | | |
|---|---|---|
| *A61K 39/145* | (2006.01) | |
| *A61K 33/40* | (2006.01) | |
| *A61K 39/00* | (2006.01) | |
| *A61K 39/02* | (2006.01) | |
| *A61K 39/112* | (2006.01) | |
| *A61K 39/12* | (2006.01) | |
| *A61K 39/275* | (2006.01) | |
| *A61P 31/14* | (2006.01) | |
| *A61P 31/16* | (2006.01) | |
| *C12N 7/00* | (2006.01) | |

(52) U.S. Cl.
CPC ............ *A61K 39/145* (2013.01); *A61K 33/40* (2013.01); *A61K 39/02* (2013.01); *A61K 39/0283* (2013.01); *A61K 39/105* (2013.01); *A61K 39/12* (2013.01); *A61K 39/275* (2013.01); *A61P 31/14* (2018.01); *A61P 31/16* (2018.01); *C12N 7/00* (2013.01); *A61K 2039/521* (2013.01); *A61K 2039/5252* (2013.01); *C12N 2760/16131* (2013.01); *C12N 2760/16134* (2013.01); *C12N 2760/16163* (2013.01); *C12N 2760/16171* (2013.01); *C12N 2770/24134* (2013.01); *C12N 2770/24163* (2013.01); *C12N 2770/24171* (2013.01); *C12N 2770/36134* (2013.01); *C12N 2770/36163* (2013.01); *C12N 2770/36171* (2013.01); *Y02A 50/30* (2018.01)

(58) Field of Classification Search
CPC .. A61K 39/145; A61K 33/40; A61K 39/0283; A61K 39/105; A61K 39/275; A61K 2039/521; A61K 2039/5252; C12N 7/00; C12N 2760/16131; C12N 2760/16134; C12N 2760/16163
See application file for complete search history.

(56) References Cited

U.S. PATENT DOCUMENTS

| | | |
|---|---|---|
| 3,981,772 A | 9/1976 | Poverenny |
| 4,235,871 A | 11/1980 | Papahadjopoulos |
| 4,501,728 A | 2/1985 | Geho |
| 4,525,349 A | 6/1985 | Montagnon |
| 4,837,028 A | 6/1989 | Allen |
| 4,902,505 A | 2/1990 | Pardridge |
| 4,957,735 A | 9/1990 | Huang |

(Continued)

FOREIGN PATENT DOCUMENTS

| | | |
|---|---|---|
| CN | 105031635 A | 11/2015 |
| JP | H04-230328 A | 8/1992 |

(Continued)

OTHER PUBLICATIONS

Aarthi, D., et al., "Validation of Binary Ethyleneimine (BEI) Used as an Inactivant for Foot and Mouth Disease Tissue Culture Vaccine," Bilogiicals 32:153-156, 2004.

(Continued)

*Primary Examiner* — Snigdha Maewall
(74) *Attorney, Agent, or Firm* — Barry L. Davison; Davis Wright Tremaine LLP

(57) ABSTRACT

Provided are surprisingly effective methods for inactivating pathogens, and for producing highly immunogenic vaccine compositions containing an inactivated pathogen rendered noninfectious by exposure to a Fenton reagent, or by exposure to a Fenton reagent or a component thereof in combination with a methisazone reagent selected from the group consisting of methisazone, methisazone analogs, functional group(s)/substructure(s) of methisazone, and combinations thereof. The methods efficiently inactivate pathogens, while substantially retaining pathogen antigenicity and/or immunogenicity, and are suitable for inactivating pathogens, or for the preparation of vaccines for a wide variety of pathogens with genomes comprising RNA or DNA, including viruses and bacteria. Also provided are highly immunogenic inactivated vaccine compositions prepared by using any of the disclosed methods, and methods for eliciting an immune response in a subject by administering such vaccine compositions.

31 Claims, 21 Drawing Sheets

(56) References Cited

U.S. PATENT DOCUMENTS

| | | | |
|---|---|---|---|
| 5,004,697 A | 4/1991 | Pardridge |
| 5,019,369 A | 5/1991 | Presant |
| 5,055,303 A | 10/1991 | Riley, Jr. |
| 5,188,837 A | 2/1993 | Domb |
| 5,254,342 A | 10/1993 | Shen |
| 5,268,164 A | 12/1993 | Kozarich |
| 5,270,202 A | 12/1993 | Raychaudhuri |
| 5,271,961 A | 12/1993 | Mathiowitz |
| 5,413,797 A | 5/1995 | Khan |
| 5,506,206 A | 4/1996 | Kozarich |
| 5,514,670 A | 5/1996 | Friedman |
| 5,534,496 A | 7/1996 | Lee |
| 5,585,103 A | 12/1996 | Raychaudhuri |
| 5,662,907 A | 9/1997 | Kubo |
| 5,695,770 A | 12/1997 | Raychaudhuri |
| 5,709,860 A | 1/1998 | Raychaudhuri |
| 5,885,586 A | 3/1999 | Eckhardt |
| 6,651,655 B1 | 11/2003 | Licalsi |
| 6,890,542 B2 | 5/2005 | Mottram |
| 8,124,397 B2 | 2/2012 | Slifka |
| 8,716,000 B2 | 5/2014 | Slifka |
| 2007/0031451 A1 | 2/2007 | Slifka |
| 2011/0318407 A1 | 12/2011 | Baras |

FOREIGN PATENT DOCUMENTS

| | | | |
|---|---|---|---|
| JP | 2001-520365 A | 10/2001 |
| JP | 2012-517979 A | 8/2012 |
| JP | 2015-221803 A | 12/2015 |
| WO | 1997/007674 A1 | 3/1997 |
| WO | 2008/026225 A2 | 3/2008 |
| WO | 2008/026226 A2 | 3/2008 |
| WO | 2008/039171 A2 | 4/2008 |
| WO | 2010/094663 A1 | 8/2010 |
| WO | 2016/063291 A1 | 4/2016 |

OTHER PUBLICATIONS

Amanna, I.J., et al., "Development of a New Hydrogen Peroxide-Based Vaccine Platform," Nature Medicine 18(6):974-979, Jun. 2012.

Barbusiński, K., "Fenton Reaction—Controversy Concerning the Chemistry," Ecological Chemistry and Engineering 16(3):347-358, 2009.

Bauer, D.J., "Clinical Experience With the Antiviral Drug Marboran® (1-Methylisatin 3-Thiosemicarbazone)," The New York Academy of Sciences 130(1):110-117, Jul. 1965.

Bauer, D.J., et al., "Prophylactic Treatment of Small Pox Contacts With N-Methylisatin Beta-Thiosemicarbazone (Compound 33T57, Marboran)," Lancet 2(7306):494-496, Sep. 7, 1963.

Bauer, D.J., "The Antiviral and Synergic Actions of Isatin Thiosemicarbazone and Certain Phenoxypyrimidines in Vaccinia Infection in Mice," The British Journal of Experimental Pathology 36(1):105-114, Feb. 1955.

Dembinski, J. L., et al., "Hydrogen Peroxide Inactivation of Influenza Virus Preserves Antigenic Structure and Immunogenicity," Journal of Virological Methods 207:232-237, Oct. 2014.

Deres, K., et al., "In Vivo Priming of Virus-Specific Cytotoxic T Lymphocytes With Synthetic Lipopeptide Vaccine," Nature 342:561-564, Nov. 30, 1989.

Federal Drug Administration, "21 Code of Federal Regulations: Parts 210 and 211," <http://www.fda.gov/dcer/dmpq/cgmpregs.htm> [retrieved Nov. 26, 2018], 31 pages.

Fox, M.P., et al., "Contact Inactivation of RNA and DNA Viruses by N-Methyl Isatin Beta-Thiosemicarbazone and CuSO4," The New York Academy of Sciences 284(1):533-543, May 1977.

Hunter, R.L., et al., "The Adjuvant Activity of Nonionic Block Polymer Surfactants. I. The Role of Hydrophile-Lipophile Balance," The Journal of Immunology 127(3):1244-1250, Sep. 1981.

Hunter, R.L., and B. Bennett, "The Adjuvant Activity of Nonionic Block Polymer Surfactants. II. Antibody Formation and Inflammation Related to the Structure of Triblock and Octablock Copolymers," The Journal of Immunology 133(6):3167-3175, Dec. 1, 1984.

Jntema, K., et al., "Hydroxyapatite Microcarriers for Biocontrolled Release of Protein Drugs," International Journal of Pharmaceutics 112(3):215-224, Dec. 1994.

Imlay, J.A., et al., "Toxic DNA Damage by Hydrogen Peroxide Through the Fenton Reaction In Vivo and In Vitro." Science 240(4852):640-642, Apr. 29, 1988.

Johnston, T.P., et al., "Sustained Delivery of Interleukin-2 From a Poloxamer 407 Gel Matrix Following Intraperitoneal Injection in Mice," Pharmaceutical Research 9(3):425-434, Mar. 1992.

Kim, J.Y., et al., "Inactivation of MS2 Coliphage by Fenton's Reagent," Water Research 44(8):2647-2653, Apr. 2010.

Langer, R., "Polymer-Controlled Drug Delivery Systems," Accounts of Chemical Research 26(10):537-542, Oct. 1993.

Lippincott Williams & Wilkins, "Nursing: The Series for Clinical Excellence, Deciphering Diagnostic Tests," Lippincott Williams & Wilkins, A Wolters Kluwer Company, Philadelphia, Pennsylvania, 2008, vii, p. 13.

Liu, L., et al., "Comparison of Plaque- and Enzyme-Linked Immunospot-Based Assays to Measure the Neutralizing Activities of Monoclonal Antibodies Specific to Domain III of Dengue Virus Envelope Protein," Clinical and Vaccine Immunology 19(1):73-78, Jan. 2012.

Logan, J.C., et al., "Arenavirus Inactivation on Contact With N-Substituted Isatin Beta-Thiosemicarbazones and Certain Cations," Journal of General Virology 28:271-283, Sep. 1, 1975.

McClatchey, K.D., "Clinical Laboratory Medicine," 2nd ed., Lippincott Williams & Wilkins, A Wolters Kluwer Company, Philadelphia, Pennsylvania, 2002, XIV, p. 452.

Mikelens, P.E., et al., "Association of Nucleic Acids With Comlexes of N-Methyl Isatin-Beta-Thiosemicarbazone and Copper," Biochemical Pharmacology 25(7):821-827, Apr. 1, 1976.

Moor, K., et al., "Peracetic Acid Treatment Generates Potent Inactivated Oral Vaccines From a Broad Range of Culturable Bacterial Species," Frontiers in Immunology 7:1-16, Feb. 11, 2016.

Nguyen, T.T.M., et al., "Microbial Inactivation by Cupric Ion in Combination With H2O2: Role of Reactive Oxidants," Environmental Science & Technology 47(23):13661-13667, 2013.

Nieto-Juarez, J.I., et al., "Inactivation of MS2 Coliphage in Fenton and Fenton-Like Systems: Role of Transition Metals, Hydrogen Peroxide and Sunlight," Environmental Science & Technology 44(9):3351-3356, 2010.

Pakravan, P., and S. Masoudian, "Study on the Interaction Between Isatin-Beta-Thiosemicarbazone and Calf Thymus DNA by Spectroscopic Techniques," Iranian Journal of Pharmaceutical Research 14(1):111-123, 2015.

"Phosphate-Buffered Saline (PBS)," Cold Spring Harbor Protocols, © 2006, <cshprotocols.schip.org/content/2006/1/pdb.rec8247> [retrieved Apr. 3, 2020], 1 page.

Pinto, A.K., et al., "A Hydrogen Peroxide-Inactivated Virus Vaccine Elecits Humoral and Cellular Immunity and Protects Against Lethal West Nile Virus Infection in Aged Mice," Journal of Virology 87(4):1926-1936, Feb. 15, 2013.

Rohde, W., et al., "Binding of N-Methyl Isatin Beta-Thiosemicarbazone-Copper Complexes to Proteins and Nucleic Acids," Journal of Inorganic Biochemistry 10(3):183-194, 1979.

Sagripanti, J.-L., et al., "Mechanism of Copper-Mediated Inactivation of Herpes Simplex Virus," Antimicrobial Agents and Chemotherapy 41(4):812-817, Apr. 1997.

Sagripanti, J.-L., "Metal-Based Formulations With High Microbicidal Activity," Applied and Environmental Microbiology 58(9):3157-3162, Sep. 1992.

Sagripanti, J.-L., et al., "Interaction of Copper With DNA and Antagonism by Other Metals," Toxicology and Applied Pharmacology 110(3):477-485, 1991.

Sagripanti, J.-L., et al., "Virus Inactivation by Copper or Iron Ions Alone and in the Presence of Peroxide," Applied and Environmental Microbiology 59(12):4374-4376, Dec. 1993.

Schmolka, I.R., "A Review of Block Polymer Surfactants," Journal of the American Oil Chemists' Society 54(3):110-116, Mar. 1977.

(56) References Cited

OTHER PUBLICATIONS

Stauffer, F., et al., "New Chemical Method of Viral Inactivation for Vaccine Development Based on Membrane Fusion Inhibition," Vaccine 25(46):7885-7892, Oct. 26, 2007.
Thompson, R.L., et al., "Effect of Heterocyclic and Other Thiosemicarbazone on Vaccinia Infection in the Mouse," The Journal of Immunology 70(3):229-234, Mar. 1, 1953.
Toyokuni, S., and J.-L. Sagripanti, "Association Between 8-Hydroxy-2'-Deoxyguanosine Formation and DNA Strand Breaks Mediated by Copper and Iron," Free Radical Biology & Medicine 20(6):859-864, 1996.
Turner, G.S., et al., "Inactivated Smallpox Vaccine. A Comparison of Inactivation Methods," Epidemiology & Infection 68(2):197-210, 1970.
Warnes, S.L., and C.W. Keevil, "Inactivation of Norovirus on Dry Copper Alloy Surfaces," PLOS One 8(9)(e75017): 1-10, Sep. 9, 2013.
European Office Action dated Apr. 2, 2020, issued in European Patent Application No. 17725054.5, filed May 10, 2017, 12 pages.
European Office Action dated Apr. 2, 2020, issued in European Patent Application No. 17727026.1, filed May 10, 2017, 13 pages.
International Search Report mailed Oct. 16, 2017, issued in corresponding International Patent Application No. PCT/US2017/032029, filed May 10, 2017, 6 pages.
International Search Report mailed Oct. 16, 2017, issued in corresponding International Patent Application No. PCT/US2017/032030, filed May 10, 2017, 5 pages.
Japanese Office Action dated Oct. 1, 2020, issued in Japanese Patent Application No. 2019-511827, filed May 10, 2017, 17 pages.
Japanese Office Action dated Oct. 5, 2020, issued in Japanese Patent Application No. 2019-511828, filed May 10, 2017, 12 pages.

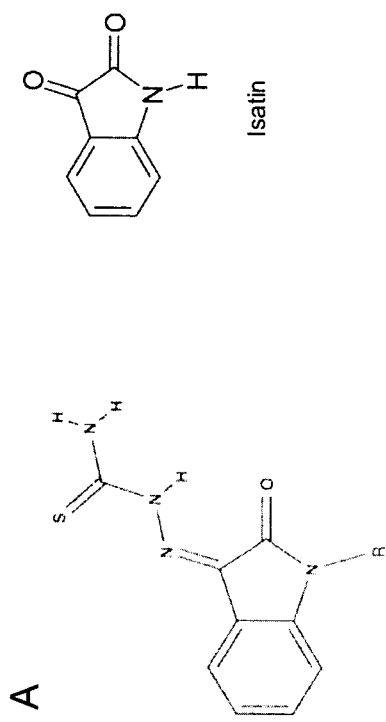
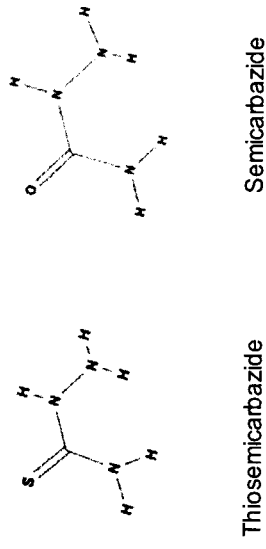
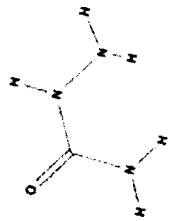
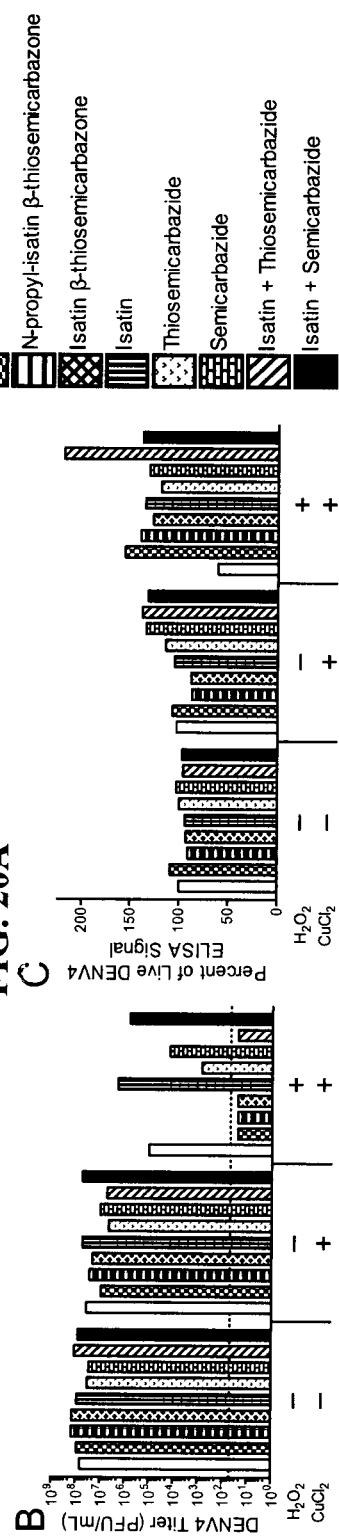
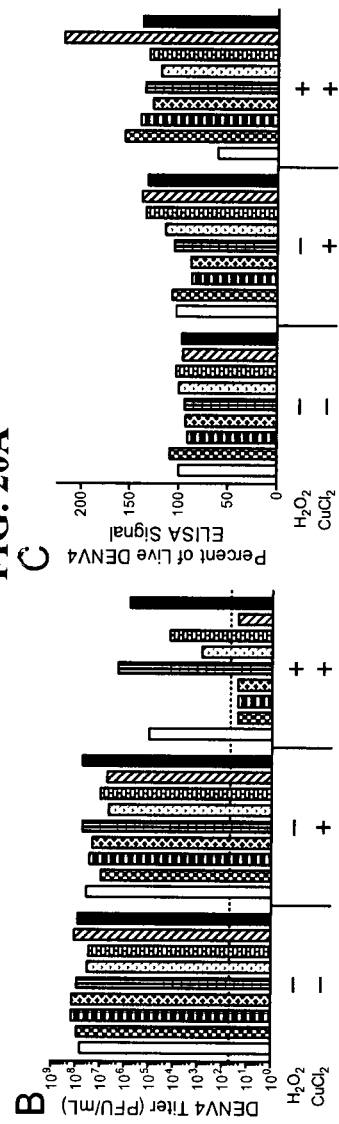
FIG. 20A
FIG. 20B
FIG. 20C

FIGS. 21

INACTIVATING PATHOGENS AND PRODUCING HIGHLY IMMUNOGENIC INACTIVATED VACCINES USING A DUAL OXIDATION PROCESS

CROSS-REFERENCE TO RELATED APPLICATION

This application is a continuation of U.S. patent application Ser. No. 17/497,810, filed Oct. 8, 2021, now U.S. Pat. No. 11,633,470, which is a divisional of U.S. patent application Ser. No. 16/300,540, filed Nov. 9, 2018, now U.S. Pat. No. 11,141,475, which is a 371 National Stage of International Patent Application No. PCT/US2017/032030, filed May 10, 2017, which claims the benefit of U.S. Provisional Patent Application No. 62/334,357, filed May 10, 2016, U.S. Provisional Patent Application No. 62/334,406, filed May 10, 2016, and U.S. Provisional Patent Application No. 62/334,588, filed May 11, 2016, the disclosures of which are herein incorporated by reference in their entirety.

STATEMENT REGARDING FEDERALLY-SPONSORED RESEARCH

This invention was made with government support under Nos. $R_{44}$-AI079898 and $R_{01}$-AI098723 awarded by the National Institute of Health. The government has certain rights in this invention.

FIELD OF THE INVENTION

Aspects of the present invention relate generally to methods for inactivating pathogens and producing highly immunogenic inactivated vaccines against pathogens, relate in more particular aspects to surprisingly effective methods for inactivating pathogens and producing highly immunogenic inactivated vaccines against pathogens having either RNA or DNA genomes, including but not limited to viral and bacterial pathogens, using dual oxidation processes employing Fenton-type chemistry, and relate in even more particular aspects to using single oxidation processes or the disclosed dual oxidation processes, in combination with a methisazone reagent (e.g., methisazone, methisazone analogs, or methisazone functional group(s)/substructure(s), or combinations thereof), to provide substantial advantages over the use of single or dual oxidation processes for viral, bacterial, fungal or parasite inactivation and vaccine production. Additional aspects relate to vaccine compositions (medicaments) containing a pathogen inactivated using the disclosed methods for producing highly immunogenic inactivated vaccines, and to methods for eliciting an immune response in a subject by administering such vaccine compositions.

BACKGROUND

Inactivated vaccines represent a critical component of the health care system for both human and veterinary fields of medicine. However, the process of inactivation (e.g., inactivation by formaldehyde, β-propiolactone (BPL), binary ethylenimine (BEI) inactivation, and hydrogen peroxide ($H_2O_2$)) can damage key antigenic epitopes of target pathogens, leading to suboptimal in vitro and in vivo responses in vaccines and reductions in in vivo vaccine efficacy.

Recent work (see, e.g., U.S. Pat. Nos. 8,124,397 and 8,716,000) has shown that chemical oxidizing agents (e.g., hydrogen peroxide ($H_2O_2$)), while previously known and used in the art only for the ability to destroy and kill pathogens, could be used in methods to prepare immunogenic inactivated viral vaccines. However, even such simple chemical oxidizing agents can give suboptimal results by damaging, to some extent, key antigenic epitopes, and to circumvent this problem, there is yet a pronounced unmet need for better, broadly applicable methods for efficiently inactivating pathogens (viral, bacterial, fungal, and parasitic) while optimally retaining immunogenicity.

Influenza, for example, commonly known as "the flu", is an infectious disease caused by an influenza virus, RNA viruses that make up three of the five genera of the family Orthomyxoviridae. Influenza spreads around the world in a yearly outbreak, resulting in about three to five million cases of severe illness and about 250,000 to 500,000 deaths. Dengue virus (DENV), for example, is the cause of dengue fever. It is a mosquito-borne, positive-sense single stranded RNA virus of the family Flaviviridae; genus *Flavivirus*. Five serotypes of the virus have been found, all of which can cause the full spectrum of disease. Its genome codes for three structural proteins (capsid protein C, membrane protein M, envelope protein E) and seven nonstructural proteins (NS1, NS2a, NS2b, NS3, NS4a, NS4b, NS5). It also includes short non-coding regions on both the 5' and 3' ends.

Chikungunya virus (CHIKV), for example, is a member of the *alphavirus* genus, and Togaviridae family. It is an RNA virus with a positive-sense single-stranded genome of about 11.6 kb. It is a member of the Semliki Forest virus complex and is closely related to Ross River virus, O'nyong'nyong virus, and Semliki Forest virus. Because it is transmitted by arthropods, namely mosquitoes, it can also be referred to as an arbovirus (arthropod-borne virus). In the United States, it is classified as a category C priority pathogen, and work requires biosafety level III precautions. Symptoms include fever and joint pain, typically occurring two to twelve days after exposure. Other symptoms may include headache, muscle pain, joint swelling, and a rash. Most people are better within a week; however, occasionally the joint pain may last for months. The risk of death is around 1 in 1,000. The very young, old, and those with other health problems are at risk of more severe disease.

*Campylobacter* (Gram-negative bacteria), for example, represents a global human pathogen and is responsible for up to 400-500 million cases of bacterial gastroenteritis each year. The economic burden of this bacterial disease is substantial, with annual US costs estimated at up to $5.6 billion. There is no commercial vaccine available for human *Campylobacter* infections and development of a safe and effective vaccine represents an important unmet clinical need. The most frequently reported species in human diseases are *C. jejuni* (subspecies *jejuni*) and *C. coli*. Other species such as *C. lari* and *C. upsaliensis* have also been isolated from patients with diarrhoeal disease, but are reported less frequently.

*Listeria* (e.g., *Listeria monocytogenes*; Gram-positive bacteria) is one of the most virulent foodborne pathogens, with fatality rates due to food-borne listeriosis reaching 20 to 30% in high-risk individuals. Responsible for an estimated 1,600 illnesses and 260 deaths in the United States (U.S.) annually, listeriosis ranks third in total number of deaths among food borne bacterial pathogens, with fatality rates exceeding even *Salmonella* and *Clostridium botulinum*. In the European Union, rates of listeriosis have followed an upward trend that began in 2008, causing 2, 161 confirmed cases and 210 reported deaths in 2014, 16% more than in 2013. Similar to the U.S., listeriosis mortality rates are also higher in the EU compared to other food-borne pathogens.

*Shigella* (e.g., *Shigella dysenteriae*; Gram-negative bacteria) is one of the leading bacterial causes of diarrhea worldwide, causing an estimated 80-165 million cases annually. The number of deaths it causes each year is estimated at between 74,000 and 600,000, and it is in the top four pathogens that cause moderate-to-severe diarrhea in African and South Asian children. *S. flexneri* is the most frequently isolated species worldwide, and accounts for 60% of cases in the developing world; *S. sonnei* causes 77% of cases in the developed world, compared to only 15% of cases in the developing world; and *S. dysenteriae* is usually the cause of epidemics of dysentery, particularly in confined populations such as refugee camps.

The present disclosure satisfies these and other needs for better vaccines.

SUMMARY OF THE INVENTION

Applicants herein disclose and demonstrate for the first time that use of a dual oxidation system, employing Fenton-type chemistry with, for example, $CuCl_2$ and $H_2O_2$, as well as use of $H_2O_2$ with other transition metal/$H_2O_2$ combinations (Fenton reaction combinations), provided a significant advantage in both inactivation and vaccine development over the use of single oxidation approaches. Neither $H_2O_2$ nor $CuCl_2$ alone, for example, were able to maintain robust antigenicity while also ensuring complete viral inactivation, both of which are critical components underlying successful inactivated vaccines. Surprisingly, using a combination of, for example, both $CuCl_2$ and $H_2O_2$, a broad variety of antigenic and immunogenic vaccines were provided, for example, for chikungunya virus (CHIKV, Family: Togaviridae, Genus: *Alphavirus*), dengue virus serotypes 1-4 (DENV 1-4) and yellow fever virus (YFV), Family: Flaviviridae, Genus: *Flavivirus*), vaccinia virus (VV), Family: Poxviridae, Genus: *Orthopoxvirus*) or influenza virus (Family: Orthomyxoviridae, Genus: *Influenzavirus*) was developed.

Particular aspects, as described in more detail below, thus provide an effective dual-oxidation method involving Fenton-type chemistry (oxidative reactions) using redox-active transition metals (e.g., Cu, Fe, Cs, etc.) in combination with hydrogen peroxide ($H_2O_2$) to form oxidative byproducts, leading to microbial inactivation with surprisingly effective retention of immunogenicity.

In additional surprising aspects, the disclosed dual-oxidation methods involving Fenton-type chemistry further comprise, as described in more detail below, the use of methisazone, methisazone analogs, or methisazone functional group(s)/substructure(s), providing even more efficient microbial inactivation relative to dual-oxidation alone, and with even more effective retention of immunogenicity relative to dual-oxidation alone.

Further surprising aspects provide effective single-oxidation methods involving hydrogen peroxide ($H_2O_2$) further comprising, as described in more detail below, the use of methisazone, methisazone analogs, or methisazone functional group(s)/substructure(s), providing for more efficient microbial inactivation relative to $H_2O_2$ alone, and with effective retention of immunogenicity.

Provided, for example, are methods for producing an immunogenic vaccine composition comprising an inactivated pathogen, the method comprising: contacting a pathogen with a Fenton reagent, comprising hydrogen peroxide in combination with a transition metal, in an amount and for a time-period sufficient for the agent to render the pathogen noninfectious while retaining pathogen immunogenicity.

The methods may further comprise verifying immunogenicity of the noninfectious pathogen using pathogen-specific antibody, B cell or T cell immunoassays, agglutination assays, or other suitable assays. In the methods using a Fenton reagent, the Fenton reagent comprises hydrogen peroxide in combination with at least one transition metal ion selected from, e.g., Cu, Fe, Cs, etc., as recognized in the art. For the methods using a Fenton reagent, a single transition metal, or a mixture of transition metals may be used in combination with hydrogen peroxide. The methods are broadly applicable where the pathogen to be inactivated while retaining immunogenicity is a pathogen having a genome comprising RNA or DNA, including but not limited to viruses, and bacteria, as disclosed herein. In particular aspects of the methods using a Fenton reagent the pathogen is a virus (e.g., Family Togaviridae, Flaviviridae, or Orthomyxoviridae) or bacterium (e.g., *Campylobacter* is *C. coli* or *C. jejuni*). In more particular aspects, the pathogen is a virus (e.g., Togaviridae, Genus: *Alphavirus*), Family: Flaviviridae, Genus: *Flavivirus*) or Family: Orthomyxoviridae, Genus: *Influenzavirus*) or bacterium (e.g., *Campylobacter*). In particular aspects, the pathogen is a chikungunya virus (CHIKV, Family: Togaviridae, Genus: *Alphavirus*), dengue virus serotypes 1-4 and yellow fever virus (DENV 1-4, YFV, Family: Flaviviridae, Genus: *Flavivirus*) or influenza virus (Family: Orthomyxoviridae, Genus: *Influenzavirus*. In particular aspects, the pathogen is a bacterium such as, but not limited to *Campylobacter* (e.g., *C. coli* or *C. jejuni*), *Shigella* spp, *Listeria* (e.g., *Listeria monocytogene*), etc., as disclosed herein.

In the dual-oxidation or single-oxidation methods disclosed herein, the pathogen is preferably isolated or purified prior to contacting with the Fenton reagent.

Also disclosed are methods for inactivating a pathogen, the method comprising: contacting a pathogen with hydrogen peroxide, or with a Fenton reagent containing hydrogen peroxide in combination with a transition metal, and a methisazone reagent, in an amount and for a time-period sufficient to render the pathogen noninfectious.

The disclosed dual-oxidation methods disclosed herein for inactivating pathogens, and for vaccine production by inactivating pathogens while retaining immunogenicity, may comprise contacting the pathogen with the Fenton reagent and a "methisazone reagent" such as methisazone, a methisazone analog(s), or one or more methisazone functional group(s)/substructure(s), or combinations thereof. For example, the dual-oxidation methods described herein may comprise contacting the pathogen with the Fenton reagent and a compound having formula I:

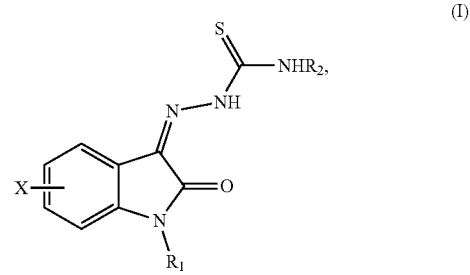

(I)

wherein $R_1$ is independently H or lower alkyl (e.g., C1-C4 alkyl) optionally substituted with —OH; wherein $R_2$ is independently H, lower alkyl (e.g., C1-C2 alkyl) optionally substituted with —OH or with aryl; and wherein X is independently H or halogen (e.g., Cl, Br, I, F, etc.); and salts, including pharmaceutically acceptable salts thereof. In particular aspects, X and $R_2$ are H; and $R_1$ is independently H (isatin β-thiosemicarbazone), —CH$_3$ (N-methyl-isatin β-thiosemicarbazone (methisazone)), or propyl (N-propyl-isatin β-thiosemicarbazone). Preferably, X and $R_2$ are H; and $R_1$ is —CH$_3$ (N-methyl-isatin β-thiosemicarbazone (methisazone)). Preferably, methisazone is used:

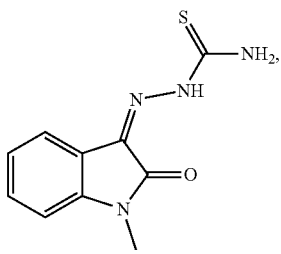

(VII)

Alternatively, or in addition, the dual-oxidation methods described herein may comprise contacting the pathogen with the Fenton reagent and one or more compounds each having one of formulas II-V:

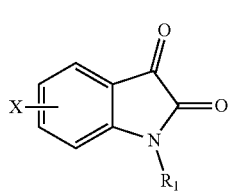

(II)

wherein $R_1$ is H or lower alkyl (e.g., C1-C4 alkyl) optionally substituted with —OH; and wherein X is independently H or halogen (e.g., Cl, Br, I, F, etc.); and salts, including pharmaceutically acceptable salts thereof;

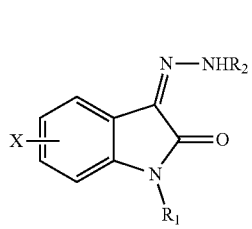

(III)

wherein $R_1$ is H or lower alkyl (e.g., C1-C4 alkyl) optionally substituted with —OH; wherein X is independently H or halogen (e.g., Cl, Br, I, F, etc.); and wherein $R_2$ is independently H, lower alkyl (e.g., C1-C2 alkyl) optionally substituted with —OH, or with aryl; and salts, including pharmaceutically acceptable salts thereof; and

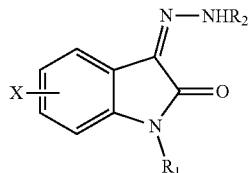

(IV)

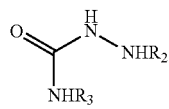

(V)

wherein $R_2$ and $R_3$ are independently H, lower alkyl (e.g., C1-C2 alkyl) optionally substituted with —OH, or with aryl; and salts, including pharmaceutically acceptable salts thereof; and combinations of such compounds each having one of the formulas II-V (or each having one of the formulas I-V). Preferably: X of formula II is H, and $R_1$ of formula (II) is H (isatin), —CH$_3$ (N-methyl-isatin), or propyl (N-propyl-isatin); X, $R_1$ and $R_2$ of formula (III) are H (indole, 2,3-dione, 3-hydrazone); $R_2$ and $R_3$ of formula (IV) are H (thiosemicarbazide); and $R_2$ and $R_3$ of formula (V) are H (semicarbazide). Preferably, contacting the pathogen comprises contacting the pathogen with the Fenton reagent, thiosemicarbazide and a compound having formula VI:

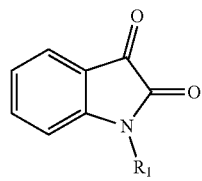

(VI)

wherein $R_1$ is H or lower alkyl (e.g., C1-C4 alkyl). Preferably, $R_1$ of formula VI is H (isatin), —CH$_3$ (N-methyl-isatin), or propyl (N-propyl-isatin). Preferably, $R_1$ of formula VI is H (isatin):

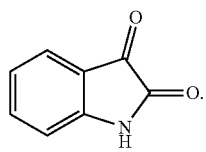

(VIII)

Also provided are immunogenic vaccine compositions having an oxidation-inactivated pathogen, produced by any of the methods disclosed herein. Preferably, the inactivated pathogen retains one or more predominant antigenic epitopes of the biologically active pathogen suitable to elicit a pathogen-specific antibody, B cell or T cell response, or to reduce infection by the pathogen, or decrease symptoms that result from infection by the pathogen. In the methods, the pathogen genome may comprise RNA or DNA.

Additionally provided are methods for eliciting an immune response against a pathogen, the methods comprising: obtaining an immunogenic vaccine composition having an oxidation-inactivated pathogen, produced by any of the methods disclosed herein; and administering the immunogenic vaccine composition to a subject, thereby eliciting in the subject an immune response against the pathogen. In the methods, the pathogen genome may comprise RNA or DNA.

Further provided are methods for producing an immunogenic vaccine composition comprising an inactivated pathogen, the method comprising: contacting a pathogen with hydrogen peroxide in combination with a methisazone-type reagent selected from the group consisting of methisazone, a methisazone analog(s) (e.g., as described herein), a methisazone functional group/substructure (e.g., as described herein), and combinations thereof (e.g., as described herein), in an amount and for a time-period sufficient to render the pathogen noninfectious while retaining pathogen immunogenicity. Preferably, the methods further comprise verifying immunogenicity of the noninfectious pathogen using pathogen-specific antibody, B cell or T cell immunoassays, agglutination assays, or other suitable assays. In the methods, the pathogen genome may comprise RNA or DNA.

Additionally provided are immunogenic vaccine compositions having an oxidation-inactivated pathogen, produced by the methods comprising contacting a pathogen with hydrogen peroxide in combination with a methisazone-type reagent.

Further provided are methods for eliciting an immune response against a pathogen, the method comprising: obtaining an immunogenic vaccine composition having an inactivated pathogen, produced by the methods comprising contacting a pathogen with hydrogen peroxide in combination with a methisazone-type reagent; and administering the immunogenic vaccine composition to a subject, thereby eliciting in the subject an immune response against the pathogen.

Further provided are methods for inactivating a pathogen, the method comprising: contacting a pathogen with a Fenton reagent, comprising hydrogen peroxide in combination with a transition metal, and a methisazone reagent, in an amount and for a time-period sufficient for the agent to render the pathogen noninfectious.

The methods are broadly applicable for producing highly immunogenic inactivated vaccines against pathogens having either RNA or DNA genomes, including but not limited to viral and bacterial pathogens.

The utility/efficacy/results are surprising and unexpected for at least six reasons.

First, prior to Applicants' U.S. Pat. Nos. 8,124,397 and 8,716,000 (hereinafter "'397" and "'000" patents having claims encompassing use of $H_2O_2$ alone in oxidative reactions for vaccine production), $H_2O_2$ was regarded as a strong oxidant and thus $H_2O_2$ reactions were known and used in the art only for the ability to destroy and kill pathogens effectively, and there was no use, suggestion or reasonable expectation to use $H_2O_2$ oxidative reactions for immunogenic vaccine production as surprisingly disclosed in Applicants' prior '397 and '000 patents. Likewise, prior to Applicants' present disclosure, and as discussed in more detail below, Fenton-type oxidative reactions ($H_2O_2$+transition metal ions) were known in the art only for the ability to destroy and kill pathogens effectively, and there was no use, suggestion or reasonable expectation to use Fenton-type oxidative reactions for immunogenic vaccine production as presently disclosed and claimed.

Second, during the initial course of investigating the presently disclosed dual-oxidation approach using Fenton-type chemistry ($H_2O_2$ and +transition metal ions), it was discovered that virus inactivation using Fenton-type chemistry was viral protein concentration-dependent, completely unlike the case for $H_2O_2$ alone, which is not protein dependent (compare FIGS. 1A and 1B herein), indicating that a fundamentally different mechanism was involved with Fenton-type chemistry-based pathogen inactivation (dual-oxidation system) compared to $H_2O_2$ alone-based pathogen inactivation (single-oxidation system). Moreover, in the dual-oxidation system, the inactivation rate decreased at higher viral protein concentrations, indicating that inclusion of the Fenton-type chemistry may be targeting the viral protein antigens, which contraindicated use of Fenton-type chemistry-based pathogen inactivation in methods seeking to retain viral protein integrity/immunogenicity. It was, therefore surprising and unexpected that Fenton-type chemistry-based pathogen inactivation actually substantially improved retention of viral protein integrity/immunogenicity, as disclosed herein.

Third, with respect to dual-oxidation methods further comprising the use of a methisazone reagent, there was no use or suggestion in the art to use a methisazone reagent (e.g., methisazone) in combination with a Fenton reagent (e.g., with $H_2O_2$ and Cu), and thus no knowledge in the art about the potential effects, if any, of methisazone on Fenton-type chemistry in any context, including not in any vaccine preparation context. Applicants are in fact the first to disclose use of a methisazone reagent in combination with a Fenton reagent, as disclosed and claimed herein.

Fourth, as discussed in more detail below, methisazone was known in the art to combine with both nucleic acid and protein, and thus would be contraindicated for use in methods such as those disclosed herein, which methods are aimed at maximally retaining the integrity and immunogenicity of pathogen protein epitopes, and particularly where the relevant pathogen protein epitopes are exposed on the pathogen surface, relative to the internally-sequestered nucleic acid of the pathogen. Moreover, the protein affinity of methisazone was particularly concerning given Applicants' initial finding, as discussed above, that Applicants' dual-oxidation reactions were viral protein concentration dependent (inactivation rate decreasing with increased viral protein concentration; FIG. 1B herein), thus contraindicating addition of yet another agent that combines with or targets protein.

Fifth, methisazone was known in the art to complex/sequester transition metal ions, which would indicate to one of ordinary skill in the chemical arts the methisazone might competitively interfere with the Fenton-type chemistry ($H_2O_2$+transition metal ions such as Cu), thus contraindicating its use in combination with Fenton-type chemistry. As discussed in more detail below, the metal ions are catalysts in the Fenton-type oxidation reactions, and thus sequestration of such catalysts by methisazone reagents would be of particular concern. Surprisingly, however, methisazone reagents substantially increased both the rate of Fenton-type chemistry-mediated pathogen inactivation, and the retention of protein integrity/immunogenicity of the inactivated pathogens.

Sixth, with respect to the disclosed methods for inactivating a pathogen, no one in the art has previously inactivated a pathogen using either hydrogen peroxide plus a methisazone reagent, or using Fenton chemistry plus a methisazone reagent, and regardless of immunogenicity retention considerations, no one could have predicted increased rates of pathogen inactivation relative to hydrogen peroxide alone, or Fenton chemistry alone.

For at least these six reasons, therefore, the results disclosed herein were surprising and unexpected, and could not have been predicted based on either the prior art, or Applicants' own prior work with simple chemical oxidizing agents (e.g., $H_2O_2$) (U.S. Pat. Nos. 8,124,397 and 8,716, 000).

The advanced dual-oxidation methods were successfully applied to eight exemplary viral vaccine targets representing four unrelated virus families (e.g., CHIKV, (Family: Togaviridae, Genus: *Alphavirus*), dengue virus serotypes 1-4 and yellow fever virus (DENV 1-4, YFV, Family: Flaviviridae, Genus: *Flavivirus*), vaccinia virus (VV), Family: Poxviridae, Genus: *Orthopoxvirus*) and influenza virus (Family: Orthomyxoviridae, Genus: *Influenzavirus* A)), and with respect to which simple oxidation (e.g., with $H_2O_2$ alone) was found to be suboptimal.

Additionally surprising, the advanced dual-oxidation methods were also successfully applied to bacterial vaccine targets (e.g., *Campylobacter, Listeria, Shigella*, etc.), in which simple oxidation (e.g., with $H_2O_2$ alone) was found to be too destructive for vaccine development (e.g., in the case of *Campylobacter*).

The disclosed dual-oxidation methods performed using Fenton-type chemistry (and optimally those methods described herein further comprising the use of a methisazone-type reagent selected from the group consisting of methisazone, methisazone analogs, methisazone functional group(s)/substructure(s), and combinations thereof) provide for robust pathogen inactivation with maintained antigenic properties to provide highly effective vaccines, leading to enhanced immunologic responses following vaccination.

BRIEF DESCRIPTION OF THE DRAWINGS

FIGS. 3A, 3B, and 3C show, according to particular aspects, that use of the disclosed dual oxidizing Fenton-type oxidation system provides efficient inactivation while improving the maintenance of CHIKV-specific neutralizing epitopes.

FIGS. 20A, 20B, and 20C show, according to particular aspects, that chemical analogs of methisazone, or methisazone functional groups/substructures, enhanced inactivation and maintenance of antigenicity during dual oxidation-based viral inactivation.

FIG. 21 shows, according to particular aspects, that increasing levels of methisazone relative to the transition metal component of the dual oxidation system improved the antigenicity and inactivation profile of the dual oxidation system.

DETAILED DESCRIPTION OF THE INVENTION

While inactivated vaccines represent a critical component of the health care system for both human and veterinary fields of medicine, the prior art processes of inactivation damage key antigenic epitopes of target pathogens (e.g., viral and bacterial), leading to suboptimal responses in vaccines and reductions in vaccine efficacy.

Particular aspects of the present invention circumvent this problem by providing a new dual-oxidation approach involving Fenton-type chemistry. Fenton-type oxidative reactions require the use of redox-active transition metals (e.g., Cu, Fe, Cs, etc.) in combination with hydrogen peroxide ($H_2O_2$) to form oxidative byproducts, leading to microbial inactivation.

The disclosed advanced Fenton-type dual-oxidation process was successfully applied to pathogens having either RNA or DNA genomes, including three exemplary bacteria (both Gram-positive and Gram negative examples, all with DNA genomes) including *Campylobacter* (e.g., *C. coli* or *C. jejuni*), *Shigella* spp, and *Listeria* (e.g., *Listeria monocytogenes*), and eight viruses (7 RNA genome viruses and 1 DNA genome virus) in four unrelated virus families as vaccine targets (e.g., chikungunya virus (CHIKV, Family: Togaviridae, Genus: *Alphavirus*), dengue virus serotypes 1-4 (DENV1, DENV2, DENV3, DENV4) and yellow fever virus (YFV), Family: Flaviviridae, Genus: *Flavivirus*), vaccinia virus (VV), Family: Poxviridae, Genus: *Orthopoxvirus*) and influenza virus (Family: Orthomyxoviridae, Genus: *Influenzavirus* A)) in which simple oxidation (e.g., hydrogen peroxide ($H_2O_2$) alone) was found to be suboptimal. For CHIKV, DENV and YFV, in vitro antigenicity was assessed through virus-specific ELISA tests based on monoclonal antibodies directed at sensitive neutralizing epitopes. Antigenicity for influenza was assessed through hemagglutination activity (HA), a direct measurement of viral protein function. In vivo enhancement of vaccine antigens was assessed through functional humoral immune assays, such as neutralizing antibody titers (CHIKV, DENV and YFV) or hemagglutination inhibition (HAI, influenza) responses following vaccination.

The disclosed dual oxidation-based inactivation conditions were successfully demonstrated to enhance maintenance of in vitro antigenicity when compared, for example, to $H_2O_2$ alone, and for CHIKV, DENV, YFV and influenza, the dual-oxidation based inactivation approach demonstrated high antigenicity as well as complete virus inactivation. When these vaccines were tested in vivo, they provided antiviral immune responses equivalent or superior to that achieved through standard $H_2O_2$-based inactivation conditions, and in some cases equivalent to that seen with live virus. The disclosed dual-oxidation performed using Fenton-type chemistry thus provides robust pathogen inactivation with maintained antigenic properties, and enhances immunologic responses following vaccination.

Fenton-Type Reactions

Fenton-type chemical reactions are generally described (e.g., by Barbusiński, K., *Fenton Reaction—Controversy concerning the chemistry*. Ecological Chemistry and Engineering, 2009. 16(3): p. 347-358; incorporated herein in its entirety for its teachings related to Fenton-type reactants and reactions) using the following chemical equation:

$$M^{n+}+H_2O_2 \rightarrow M^{(n+1)+}+HO^-+HO\bullet \quad \text{(eq. 1)}$$

In equation 1, M is a transition metal that can interact with $H_2O_2$. This reaction leads to the decomposition of $H_2O_2$, resulting in the production of a hydroxyl ion ($HO^-$) and the highly reactive hydroxyl radical ($HO\bullet$). Note that certain transition metals, such as Fe and Cu, are considered particularly redox active, and most efficient in promoting this reaction. In the complete reaction, the metal ion is returned to its original oxidation state through an additional reaction with $H_2O_2$, making the metal ion a true catalyst (Id). As an example, the overall reaction with $Cu^{2+}$ can be written as follows:

$$Cu^{2+}+H_2O_2 \rightarrow Cu^{+}+HO_2\bullet+H^{+} \quad \text{(eq. 2)}$$

$$Cu^{+}+H_2O_2 \rightarrow Cu^{2+}+HO^-+HO\bullet \quad \text{(eq. 3)}$$

In equation 2, $H_2O_2$ acts as a reducing agent, reducing $Cu^{2+}$ to $Cu^{+}$. In equation 3, the Cut in turn reduces $H_2O_2$ leading to the production of the reactive hydroxyl radical and return to the $Cu^{2+}$ oxidation state, allowing subsequent rounds of catalysis. As described, there may be additional side reactions that occur during Fenton-type reactions (Id).

Prior Art Use of Fenton-Type Oxidation was Only as a Broad-Based Sterilization and Pathogen Decontamination System As mentioned above, similar to case for the standalone disinfectant uses of $H_2O_2$ prior to Applicants' U.S. Pat. Nos. 8,124,397 and 8,716,000, prior to the present disclosure, Fenton-type reactions were known in the art only for inactivation/sterilization of microbial pathogens (e.g., see Sagripanti, J. L., L. B. Routson, and C. D. Lytle, *Virus inactivation by copper or iron ions alone and in the presence of peroxide*. Appl Environ Microbiol, 1993. 59(12): p. 4374-6; Nieto-Juarez, J. I., et al., *Inactivation of MS2 coliphage in Fenton and Fenton-like systems: role of transition metals, hydrogen peroxide and sunlight*. Environ Sci Technol, 2010. 44(9): p. 3351-6).

For example, Fenton-type oxidation has been recognized by multiple groups as a potent antimicrobial platform. FDA researchers first detailed the systematic study of Fenton-type reactions as an antimicrobial approach, specifically aimed towards use in the sterilization of medical devices (Sagripanti, J. L., *Metal-based formulations with high microbicidal activity*. Appl Environ Microbiol, 1992. 58(9): p. 3157-62). Using the Junin virus (ssRNA, Genus: *Arenavirus*) as a model pathogen, rapid inactivation was observed with both $Fe^{3+}$ and $Cu^{2+}$ as catalysts in the redox reaction (eq. 1), working as well as standard sterilization approaches (2% glutaraldehyde) following optimization. As noted by the author at the time, the use of either of these metals was particularly attractive for medical purposes, given that normal human serum contains relatively high amounts of both Fe and Cu. For instance, total serum Cu levels in normal subjects ranges from 700-1500 μg/L (11-24 μM) (McClatchey, K. D., *Clinical laboratory medicine*. 2nd ed. 2002, Philadelphia: Lippincott Wiliams & Wilkins. xiv, p. 452), while Fe levels range from 500-1700 μg/L (9-30 μM) (Lippincott Williams & Wilkins., *Nursing. Deciphering diagnostic tests*. Nursing. 2008, Philadelphia, PA: Wolters Kluwer/Lippincott Williams & Wilkins. vii, p. 13). This same research group continued to expand on the Cu-based Fenton reaction, demonstrating antimicrobial activity against multiple viral targets such as ϕX174 bacteriophage (ssDNA), T7 bacteriophage (dsDNA), herpes simplex virus (HSV, dsDNA) and ϕ6 bacteriophage (dsRNA) (Sagripanti, J. L., L. B. Routson, and C. D. Lytle, *Virus inactivation by copper or iron ions alone and in the presence of peroxide*. Appl Environ Microbiol, 1993. 59(12): p. 4374-6). Additional studies with HSV using the $H_2O_2/Cu^{2+}$ system (0.01% $H_2O_2$, 16 μM $Cu^{2+}$) confirmed rapid inactivation and suggested that direct oxidation of nucleic acid underpins the viral inactivation (Sagripanti, J. L., et al., *Mechanism of copper-mediated inactivation of herpes simplex virus. Antimicrob Agents Chemother,* 1997. 41(4): p. 812-7), with supporting studies demonstrating the high affinity of $Cu^{2+}$ for nucleic acids (Sagripanti, J. L., P. L. Goering, and A. Lamanna, *Interaction of copper with DNA and antagonism by other metals*. Toxicol Appl Pharmacol, 1991. 110(3): p. 477-85) and the ability of $H_2O_2/Cu^{2+}$ systems to induce strand breaks in nucleic acids (Toyokuni, S. and J. L. Sagripanti, *Association between 8-hydroxy-2'-deoxyguanosine formation and DNA strand breaks mediated by copper and iron*, in *Free Radic Biol Med.* 1996: United States. p. 859-64). Several other groups have also demonstrated the pathogen inactivation potential of $H_2O_2/Cu^{2+}$ systems. Nieto-Juarez, et. al., demonstrated rapid inactivation of MS2 bacteriophage (ssRNA) using 50 μM $H_2O_2$ (0.00017%) and 1 μM $Cu^{2+}$, with the authors suggesting its potential for wastewater decontamination (Nieto-Juarez, J. I., et al., *Inactivation of MS2 coliphage in Fenton and Fenton-like systems: role of transition metals, hydrogen peroxide and sunlight*. Environ Sci Technol, 2010. 44(9): p. 3351-6) (see also Nguyen, T. T., et al., *Microbial inactivation by cupric*

*ion in combination with $H_2O_2$: role of reactive oxidants.* Environ Sci Technol, 2013. 47(23): p. 13661-7).

In total, these prior art studies were strictly in the context of decontamination, and merely demonstrate that the $H_2O_2$/$Cu^{2+}$ system was known to be able to efficiently kill/sterilize model pathogens.

Simple Oxidation with $H_2O_2$ Limited Vaccine Immunogenicity with Certain Pathogen Targets Applicants have previously shown (e.g., U.S. Pat. Nos. 8,124,397 and 8,716,000) that sole use of $H_2O_2$ as a simple oxidation agent provides suitable inactivation agent for various vaccine candidates.

Figures 2A, 2B:
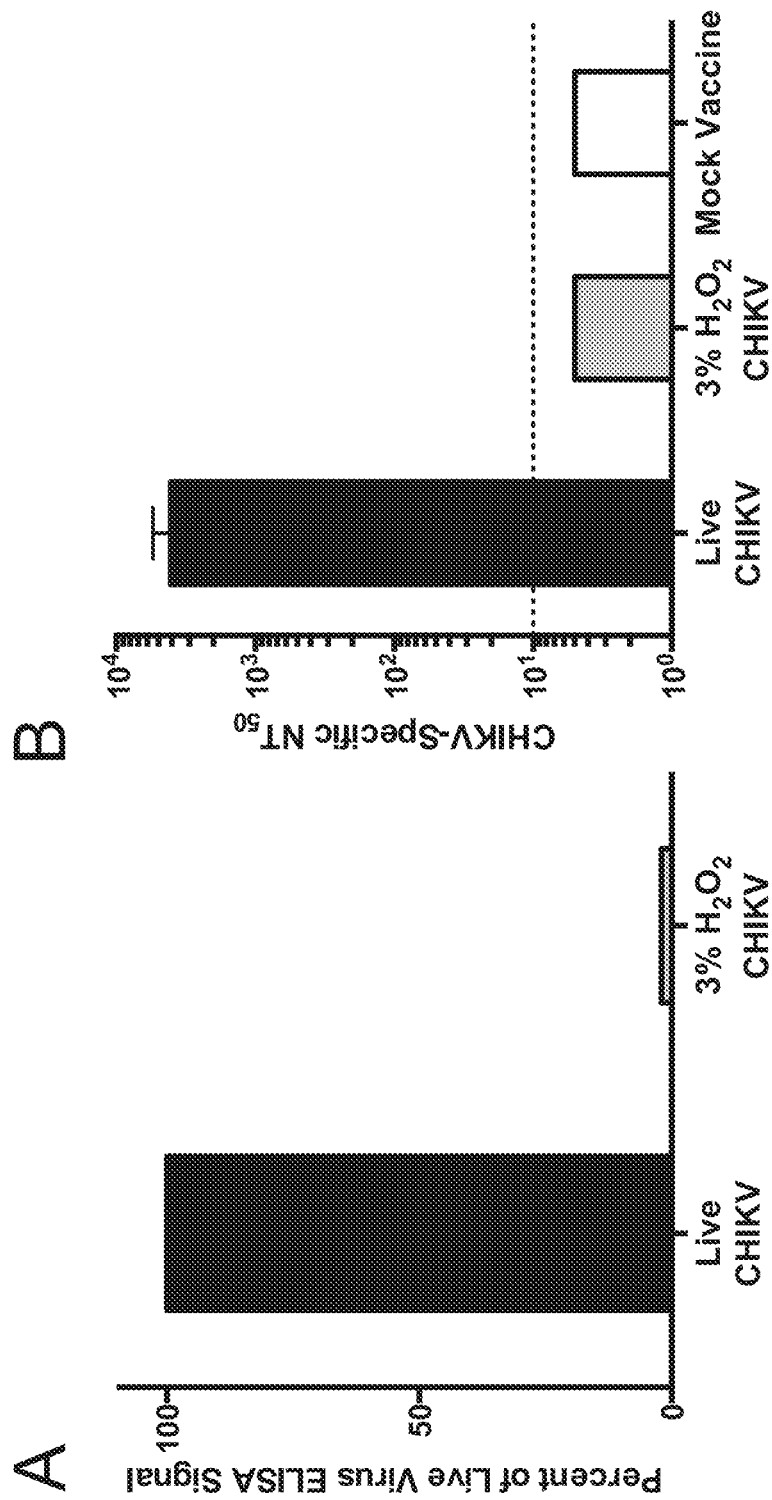
FIGS. 2A and 2B show, according to particular aspects, that standard $H_2O_2$-based inactivation damages CHIKV-specific neutralizing epitopes, and fails to induce neutralizing responses in vivo following vaccination.

However, during continued development of oxidizing with $H_2O_2$ alone, instances with certain pathogens in which antigenicity and immunogenicity were reduced during the inactivation process were encountered. For example, during recent early-stage development of a chikungunya virus (CHIKV) vaccine candidate, we found as presented herein under working Example 1, that treatment with 3% $H_2O_2$ under standard conditions destroyed neutralizing epitopes and led to a nearly complete loss of antigenicity, as judged through in vitro potency testing using envelope-specific MAbs (FIG. 2A). This loss of measured antigenicity had significant implications for in vivo immunogenicity since $H_2O_2$-inactivated CHIKV-immunized animals were unable to mount measurable neutralizing antiviral antibody responses (FIG. 2B).

Dual Oxidation-Based Microbial Inactivation was Found by Applicants to have a Fundamentally Different Mechanism Compared with Simple Oxidation with $H_2O_2$ Alone, Thereby Initially Discouraging the Potential Use of Dual Oxidation-Based Microbial Inactivation for the Development of Advanced Efficacious Vaccine Antigens.

Figures 1A, 1B:
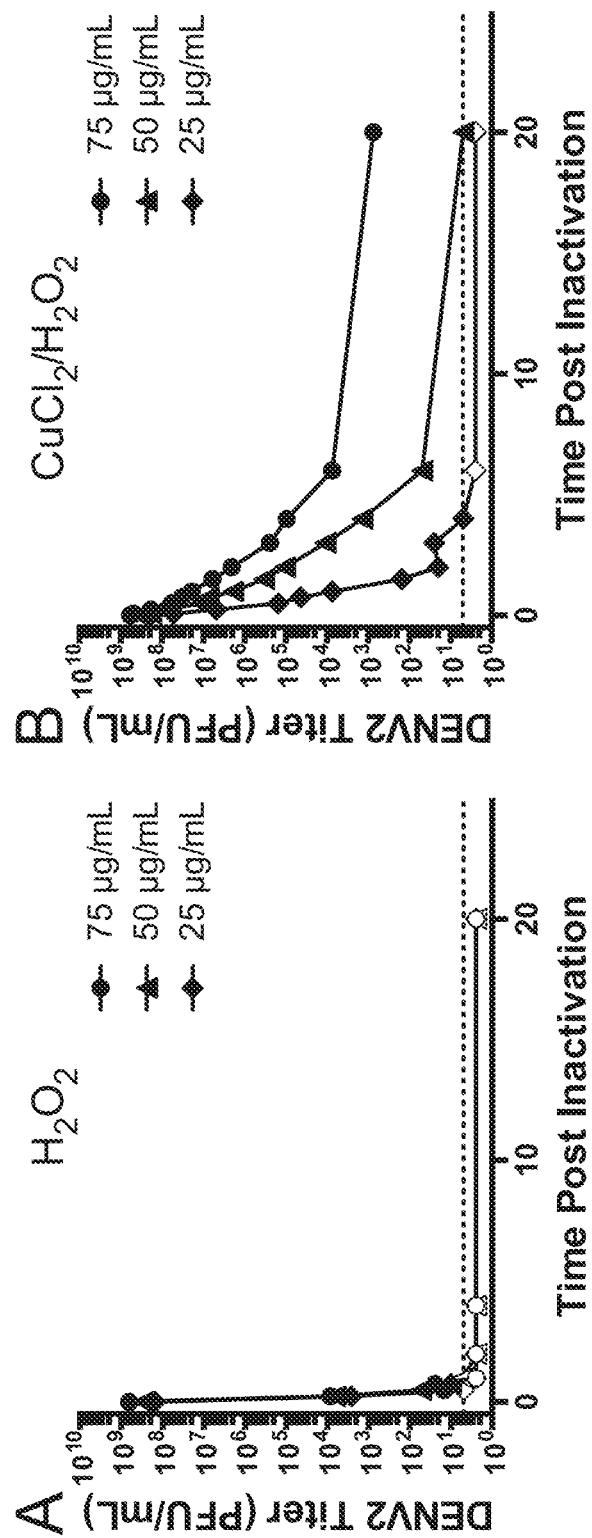
FIGS. 1A and 1B show, according to particular aspects, that the kinetics of virus inactivation using the $H_2O_2$/$CuCl_2$ dual oxidation system is protein concentration-dependent, whereas standard $H_2O_2$-based virus inactivation is protein concentration-independent.

While Fenton-type reactions have only been used in the prior art for killing pathogens, and have not been used or suggested for use in the development of vaccines, Applicants nonetheless tested, as shown herein under working Example 2, such reactions for the potential to inactivate microbial pathogens for purpose of vaccine production. The initial inactivation data was surprising and unexpected, because in contrast to $H_2O_2$, it was found that the total protein concentration of the solution during the inactivation procedure impacts $H_2O_2$/$CuCl_2$ dual-oxidation inactivation kinetics. Protein concentration had been previously shown to have no impact on viral inactivation using Applicants' standard $H_2O_2$ approach. As shown in FIGS. 1A and 1B for DENV2, using the dual oxidation approach, protein concentration had a substantial impact in viral inactivation kinetics, with higher protein levels leading to slower inactivation of the virus.

The unexpected dependence on total protein concentration of the solution during the dual inactivation indicated that a fundamentally different mechanism was involved compared to $H_2O_2$ alone as in Applicants' prior simple oxidation based methods (e.g., with $H_2O_2$ alone) (e.g., U.S. Pat. Nos. 8,124,397 and 8,716,000), and thus the efficacy/use of a dual oxidation-based inactivation procedure for effective vaccine production was entirely questionable and unpredictable.

Applicants, despite the discovery of a different, protein concentration-dependent mechanism, nonetheless performed additional experiments discussed herein and included in the working examples below, to show that Fenton-type dual oxidation reactions can surprisingly be used to effectively inactivate microbial pathogens, and provide for highly immunogenic and effective vaccines.

Dual Oxidation-Based Inactivation in the Development of Advanced Vaccine Antigens.

The Fenton-type oxidation (e.g., the $H_2O_2$/$Cu^{2+}$ system) has not been used or suggested for use in the art for the development of vaccines. Despite Applicants' discovery that a fundamentally different mechanism was involved (i.e., protein concentration dependence), Applicants nonetheless explored this system's utility in the development of a vaccine candidate against CHIKV, as this target had demonstrated poor immunogenicity with no induction of neutralizing antibodies using a standard $H_2O_2$ inactivation approach (FIGS. 2A and 2B).

Each component of the system alone ($H_2O_2$ or $CuCl_2$, a source of $Cu^{2+}$ ions) was first assessed in terms of their respective ability to fully inactivate virus while maintaining appropriate antigenicity. Antigenicity is defined by the ability to measure intact protein epitopes on the virus surface using monoclonal antibodies that bind specific virus neutralizing epitopes. Alternatively, structural antigenicity can also be defined by physiologic protein function/binding assays, such as those used to measure hemagglutination activity of influenza virus. The antigenicity results based on monoclonal antibody binding to CHIKV are shown herein under working Example 3.

Increasing concentrations of either decontamination reagent (FIGS. 3A and 3B) led to enhanced inactivation, but at the expense of significantly decreased antigenicity due to damage of neutralizing epitopes.

Figure 3C:
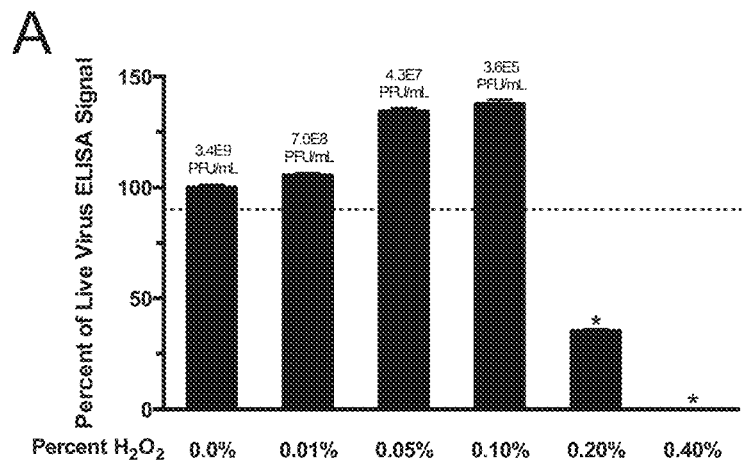

Surprisingly, by contrast, using the combined $H_2O_2$/$CuCl_2$ system, an optimal inactivation condition was identified that fully maintained antigenicity while leading to complete viral inactivation (FIG. 3C).

$CuCl_2$/$H_2O_2$-CHIKV Vaccination Generated Rapid and Robust Neutralizing Antibody Titers, and Demonstrated Full Protection Against Arthritic Disease To assess the immunogenicity of the $H_2O_2$/$CuCl_2$-treated CHIKV candidate, vaccine antigen was formulated with alum adjuvant and used to immunize mice at several dose levels (10 or 40 µg per animal). As shown herein under working Example 4, $CuCl_2$/$H_2O_2$-CHIKV vaccination generated rapid and robust neutralizing antibody titers (FIG. 4), and demonstrated full protection against arthritic disease (FIG. 5).

$H_2O_2$/$CuCl_2$-Based Oxidation was Successfully Used in the Development of an Inactivated YFV Vaccine Based on the encouraging results demonstrated with CHIKV, a model *alphavirus*, the utility of the system for flaviviruses such as YFV was explored.

Figures 6A, 6B:
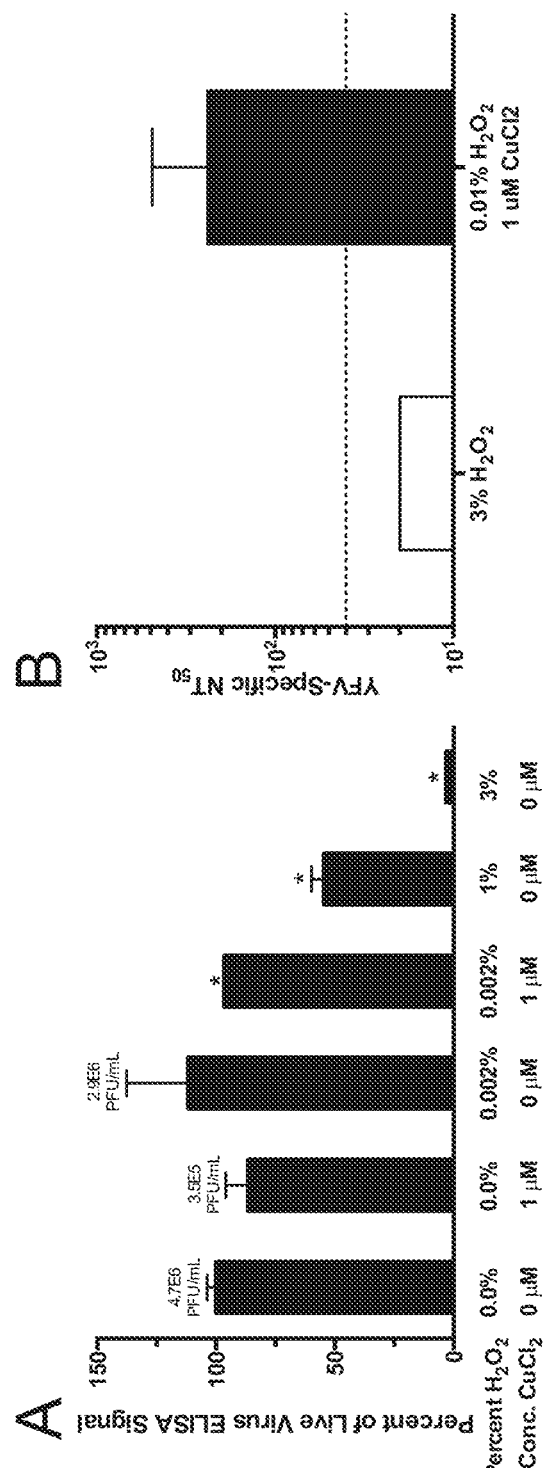
FIGS. 6A and 6B show, according to particular aspects, that use of the disclosed dual-oxidation approach with the yellow fever virus (YFV) demonstrates enhanced retention of antibody binding to neutralizing epitopes (antigenicity) and improved immunogenicity after vaccination.

As shown herein under working Example 5, preliminary analysis suggested that a concentration of 0.002% $H_2O_2$ and 1 µM $CuCl_2$ represented a functional balance between antigenicity and rapid virus inactivation (FIG. 6A). Using a further optimized condition of 0.10% $H_2O_2$ and 1 µM $CuCl_2$ (to ensure full inactivation) vaccine material was produced for YFV and used to immunize adult BALB/c mice. Following vaccination, all animals demonstrated measurable neutralizing titers with an average neutralizing titer of 240, compared to a neutralizing titer of less than 40 for animals immunized with YFV vaccine prepared using $H_2O_2$ alone (FIG. 6B). These differences in immunogenicity after vaccination could be anticipated based on the severe damage to neutralizing epitopes (i.e., antigenicity) observed when YFV was treated with 3% $H_2O_2$ for 20 hours. FIGS. 6A and 6B show that $H_2O_2$/$CuCl_2$-based oxidation was successfully used in the development of an inactivated YFV vaccine.

$H_2O_2/CuCl_2$-Based Oxidation was Successfully Used in the Development of an Inactivated DENV Vaccine Based on the encouraging results demonstrated with YFV, another model *flavivirus*, dengue 3 (DENV3) was tested in the $H_2O_2/CuCl_2$ system.

Figure 7:
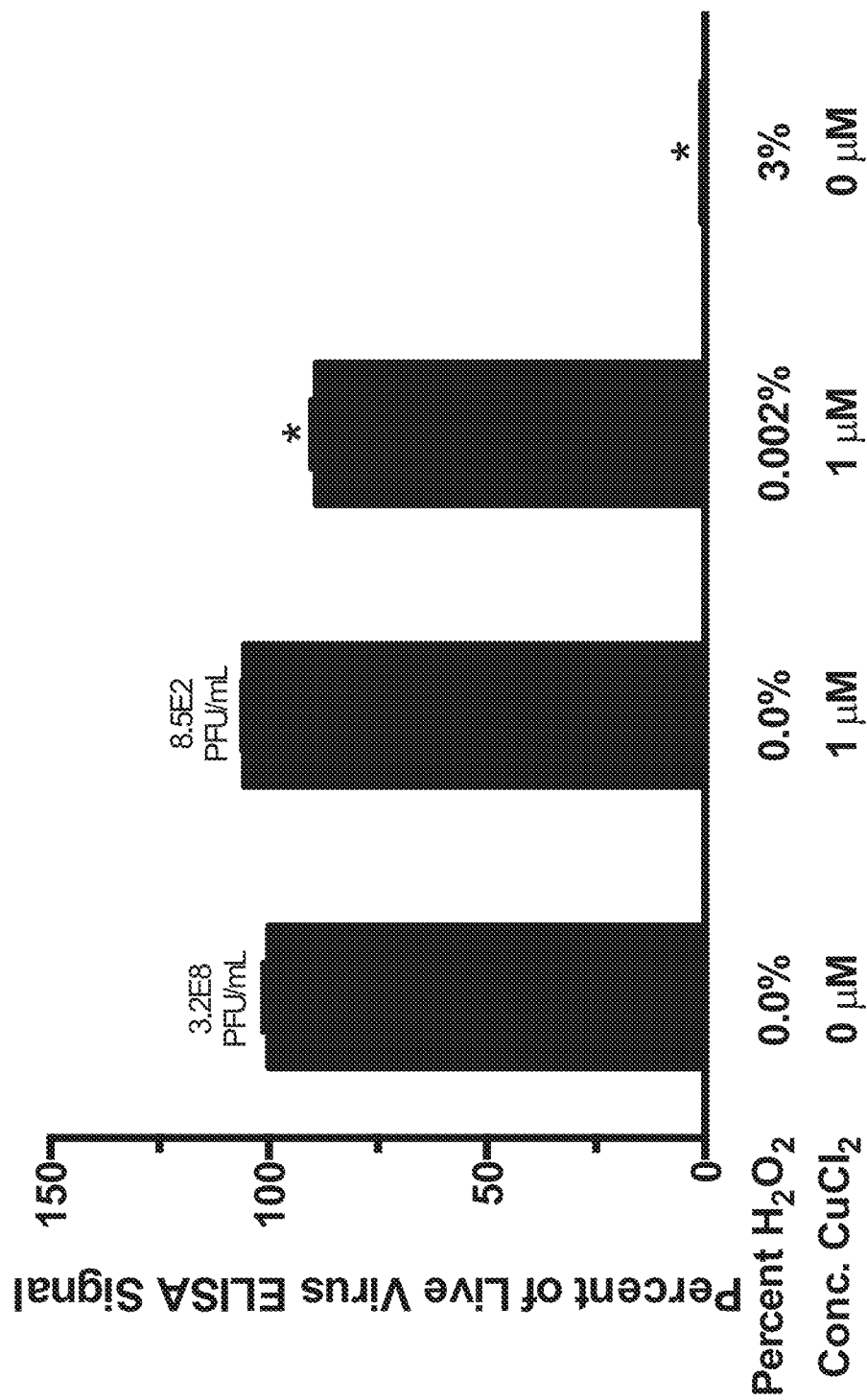
FIG. 7 shows, according to particular aspects, that use of the disclosed dual-oxidizing Fenton-type oxidation system demonstrates enhanced inactivation while maintaining dengue virus 3-specific neutralizing epitopes.
Figure 8:
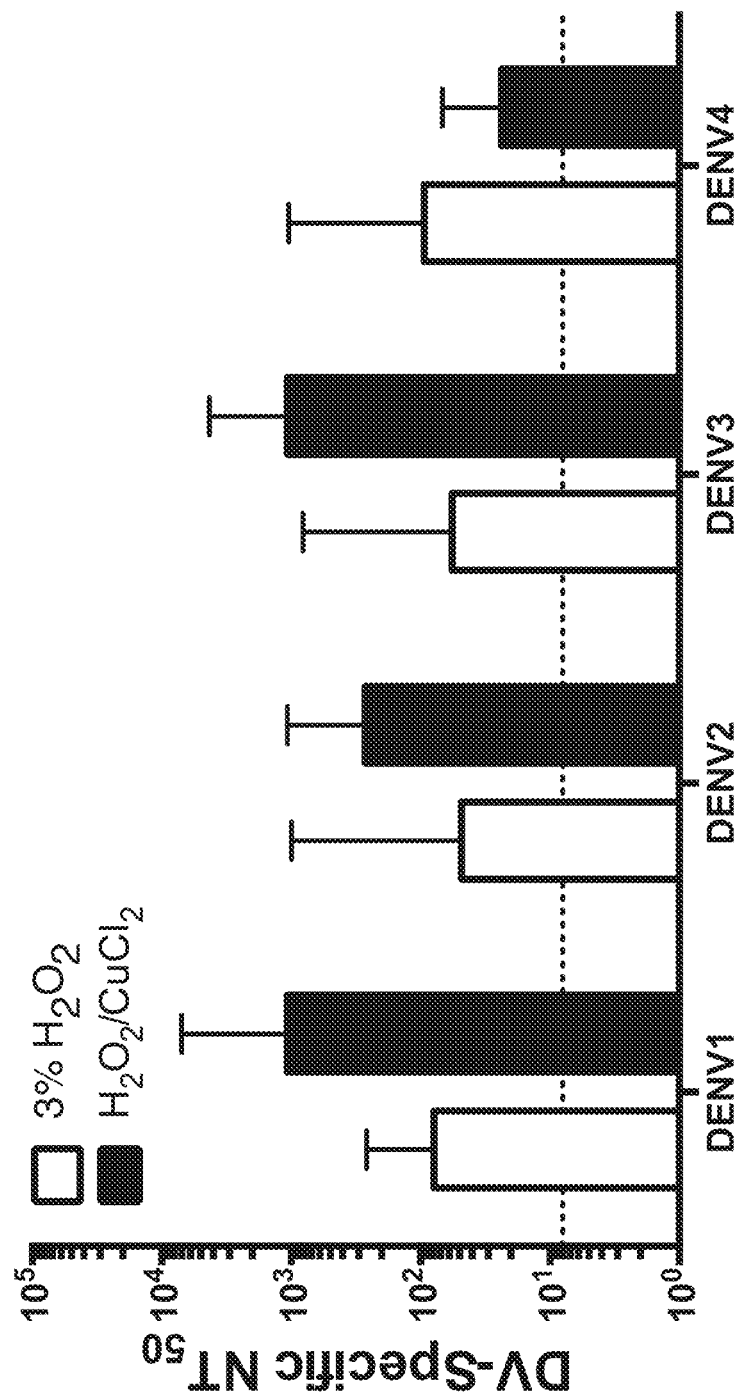
FIG. 8 shows, according to particular aspects, that use of the disclosed $H_2O_2$/$CuCl_2$ dual-oxidation system enhances in vivo immunogenicity to 3 out of 4 DENV serogroups following immunization with a tetravalent DENV vaccine in rhesus macaques (RM).
Figure 9:
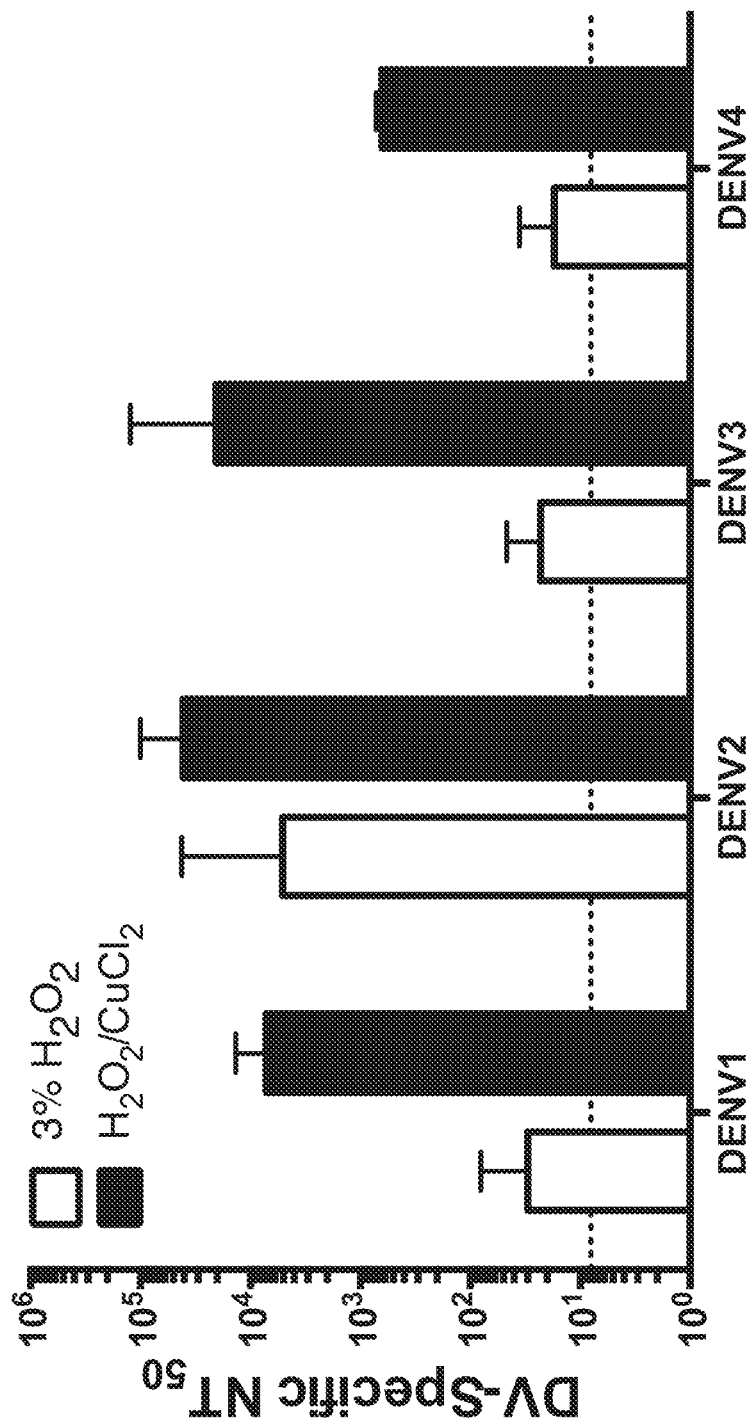
FIG. 9 shows, according to particular aspects, that use of the disclosed $H_2O_2$/$CuCl_2$ dual-oxidation system enhances in vivo immunogenicity to 4 out of 4 DENV serogroups following immunization with a tetravalent DENV vaccine in mice.

As shown herein under working Example 6, as with YFV, initial tests indicated that a concentration of 0.002% $H_2O_2$ and 1 µM $CuCl_2$ represented an optimal approach for maintaining high antigenicity while also providing complete virus inactivation (FIG. 7). Using these preliminary $H_2O_2$/ $CuCl_2$ inactivation conditions, vaccine lots of each DENV serotype were produced, formulated into a tetravalent dengue vaccine adjuvanted with 0.10% aluminum hydroxide, and used to immunize adult rhesus macaques. Following a single booster immunization, all monkeys seroconverted ($NT_{50} \geq 10$), with the $H_2O_2/CuCl_2$ inactivation approach demonstrating an improvement in neutralizing antibody responses for 3 out of 4 dengue virus serotypes and an average 8-fold increase in geometric mean titers when compared to inactivation with $H_2O_2$ alone (FIG. 8). There was a small difference in antigen dose (1 µg/serotype vs. 2 µg/serotype) in these studies and so the experiment was repeated in mice that were vaccinated with the same dose of tetravalent dengue vaccine antigen (FIG. 9).

In these experiments, the dual oxidation approach of $H_2O_2/CuCl_2$ inactivation was more immunogenic than 3% $H_2O_2$ for all 4 dengue virus serotypes and resulted in an 8-fold to >800-fold increase in neutralizing antibody titers.

$CuCl_2/H_2O_2$-Based Oxidation Demonstrated Improved Antigenicity with Influenza Virus Given the positive results observed across two virus families (Togaviridae and Flaviviridae), an additional virus family was chosen to test using this new inactivation platform.

Figure 10:
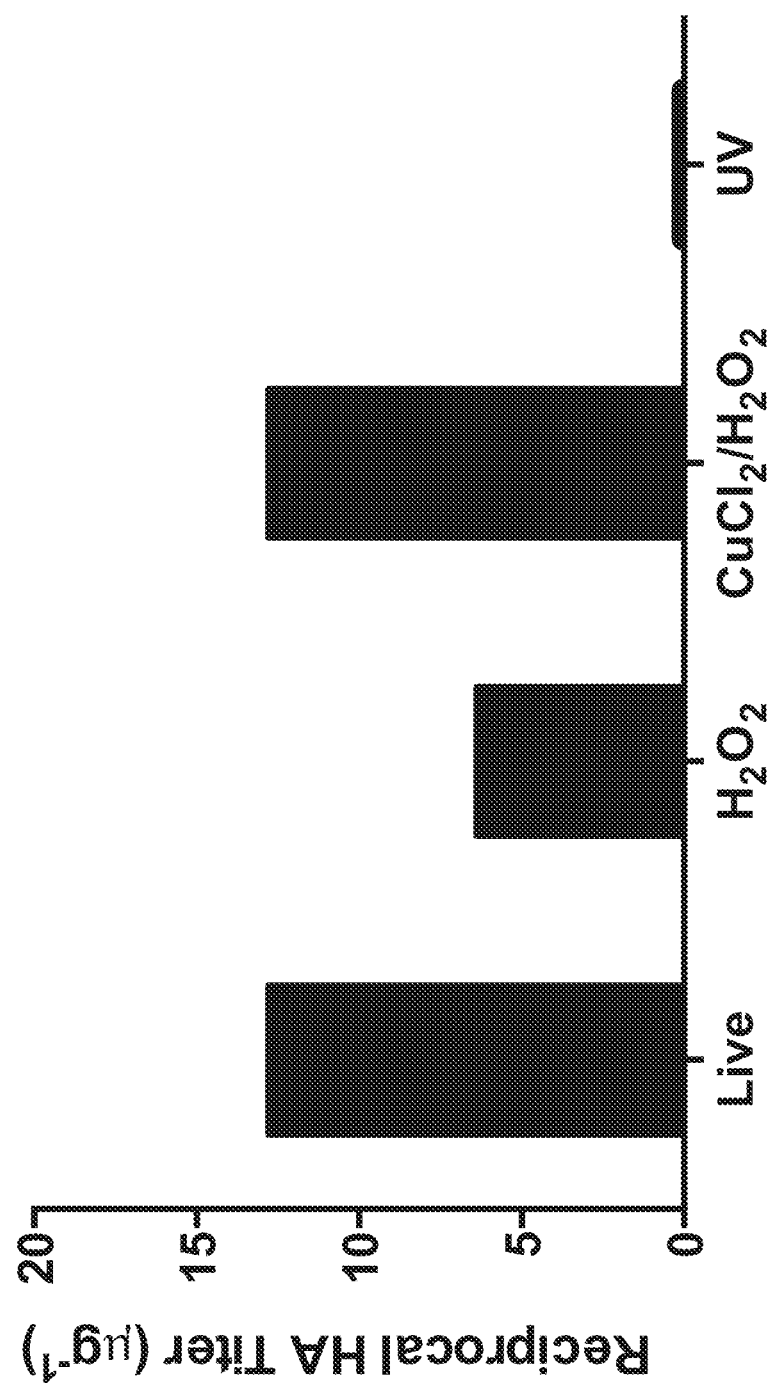
FIG. 10 shows, according to particular aspects, that the disclosed $CuCl_2$/$H_2O_2$-based virus inactivation maintains influenza hemagglutination activity significantly better than $H_2O_2$ alone.

As shown herein under working Example 7, inactivation of Influenza A virus (family Orthomyxoviridae) was tested using a standard 3% $H_2O_2$ approach, ultraviolet inactivation, or the optimized $CuCl_2/H_2O_2$ system (0.002% $H_2O_2$ and 1 µM $CuCl_2$). To assess antigenicity, a hemagglutination activity (HA) titration assay was used. Influenza viruses naturally agglutinate red blood cells, and maintenance of this activity throughout inactivation is considered key to the immunogenicity of the final vaccine product. As shown in FIG. 10, Applicants' $CuCl_2/H_2O_2$ system maintained HA titers similar to that observed for live, untreated antigen. By comparison, UV inactivation reduced HA activity to a negligible level. The in vivo consequence of this HA destruction can be seen in FIG. 11, with the $CuCl_2/H_2O_2$ inducing robust protective serum antibody hemagglutinin inhibition (HAI) titers, while UV-treated antigen induced no functional antibodies in mice and minimal protection against lethal challenge.

Multiple Transition Metals can be Used in the Dual-Oxidation Approach to Vaccine Antigen Development $Cu^{2+}$ (in the form of $CuCl_2$) was the initial metal tested in the dual-oxidation vaccine antigen development studies described for CHIKV, DENV, YFV and influenza virus. However, as described above, other metals also have the potential to function in a similar manner.

As shown herein under working Example 8, using DENV3 as a model virus, inactivation studies consisting of $CuCl_2$ ($Cu^{2+}$), $FeCl_3$ ($Fe^{3+}$) or $CsCl$ ($Cs^+$) and dilutions of $H_2O_2$ were tested for their potential in the development of vaccine antigen.

Figures 12A, 12B, 12C:
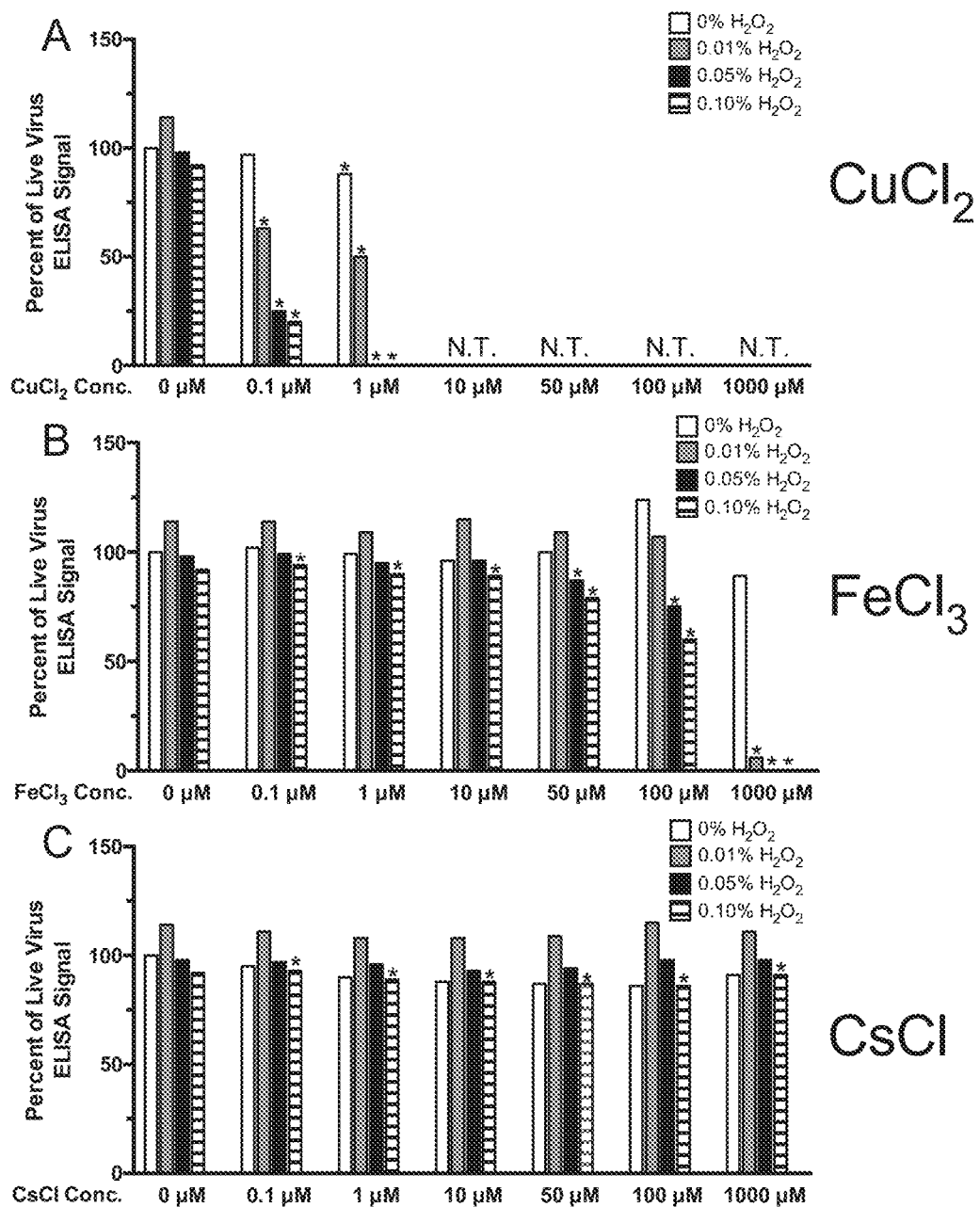
FIGS. 12A, 12B, and 12C show, according to particular aspects, a comparison of exemplary redox-active metals for the disclosed dual oxidation-based virus inactivation methods.

As shown in FIGS. 12A-12C, all three metals provided conditions that maintained high levels of antigenicity while demonstrating complete virus inactivation.

Combinations of Transition Metals Demonstrate Synergy in the Dual-Oxidation Vaccine System As shown above in FIG. 11 and working Example 8, different metals can be used in combination to enhance $H_2O_2$ inactivation of viruses.

Figure 13:
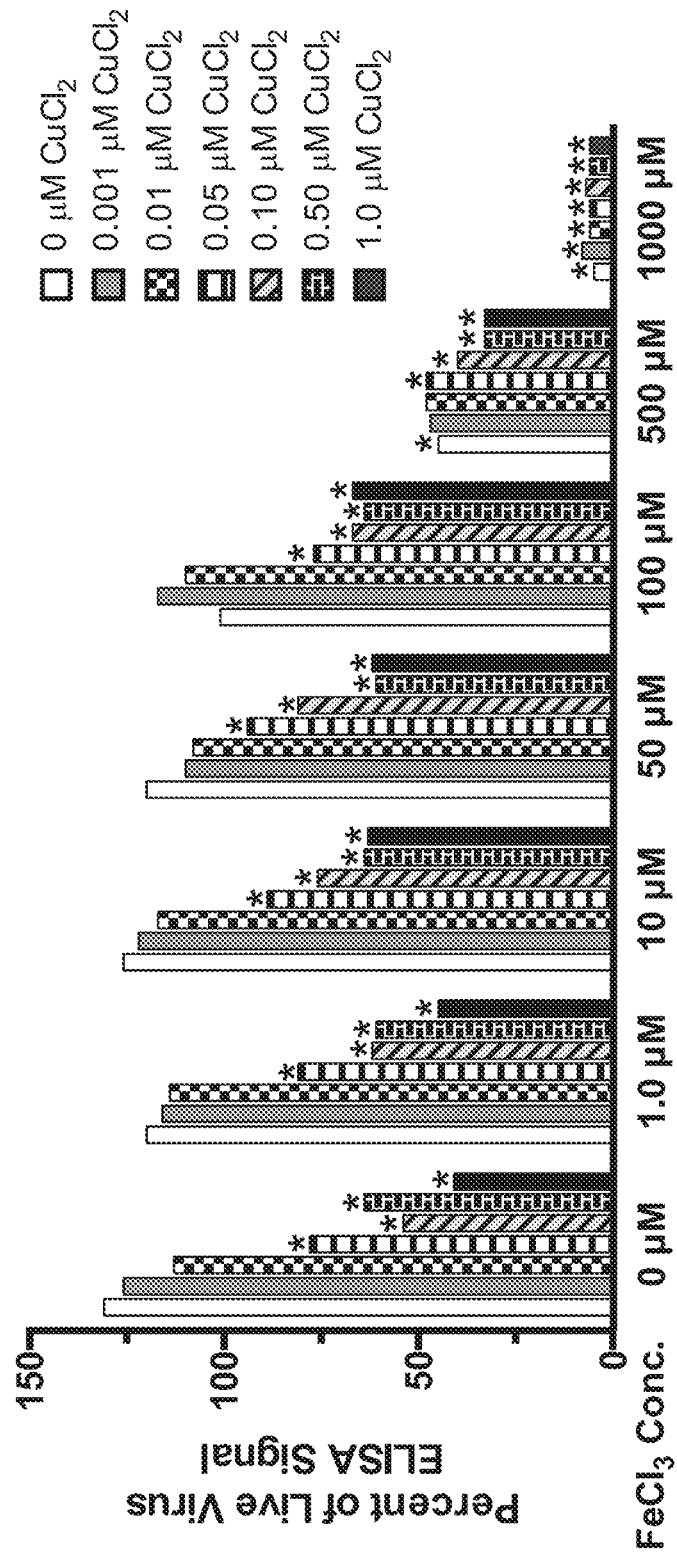
FIG. 13 shows, according to particular aspects, that combinations of metals can be used to achieve complete inactivation while maintaining good antigenicity.

As shown herein under working example 9, to investigate potential synergistic effects, DENV3 model virus was inactivated with combinations of $CuCl_2$ ($Cu^{2+}$) and $FeCl_3$ ($Fe^{3+}$) at a set amount of $H_2O_2$ (0.01%). A number of $CuCl_2/FeCl_3$ conditions provided full inactivation while maintaining good antigenicity, demonstrating that using multiple metals in the same inactivation condition is feasible (FIG. 13). Indeed, at $CuCl_2$ concentrations of 0.05 UM and 0.10 µM, increasing $FeCl_3$ concentrations enhanced antigenicity, indicating synergy with these two metals.

Figures 14A, 14B, 14C:
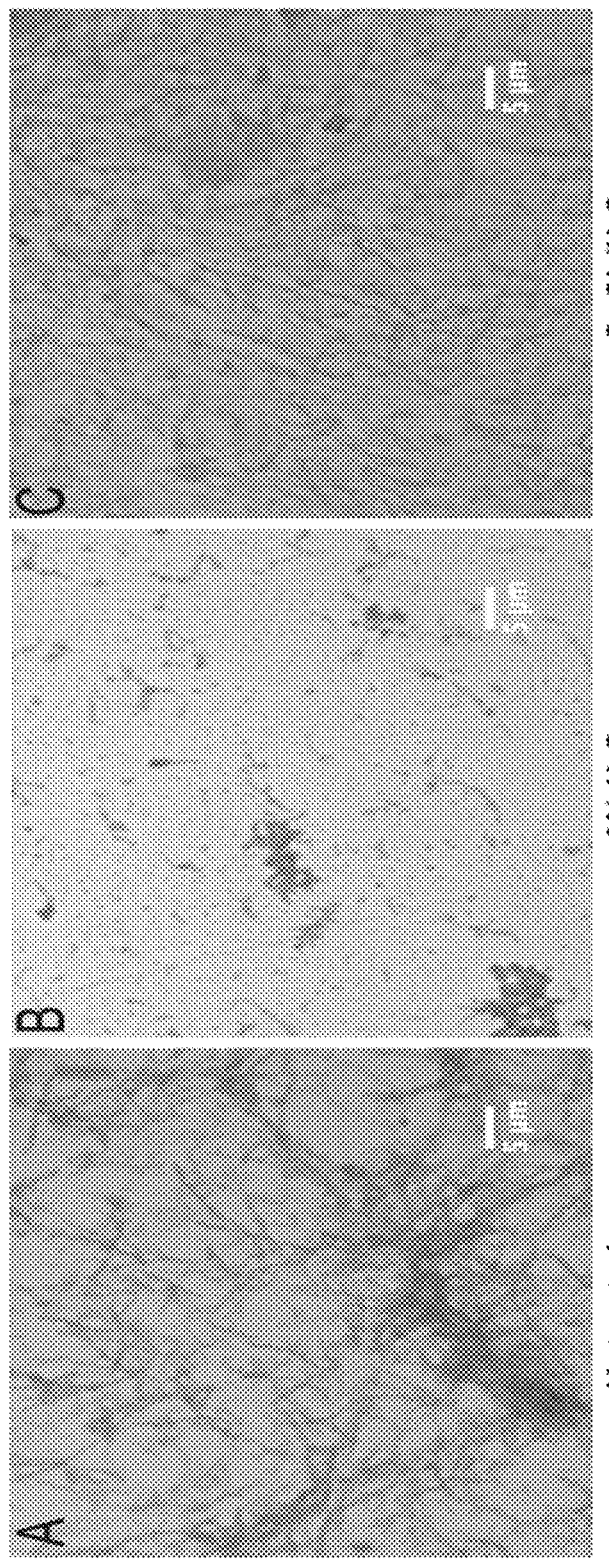
FIGS. 14A, 14B, and 14C show, according to particular aspects, use of the disclosed dual-oxidizing Fenton-type oxidation system for optimized inactivation of *Campylobacter* for improved maintenance of bacterial morphology.

Dual Oxidation was Used to Provide Optimized Inactivation of *Campylobacter* for Improved Maintenance of Bacterial Morphology As shown herein under working Example 10, *Campylobacter* are small corkscrew-shaped bacteria that are typically ~0.2 µm in diameter and ~2-8 µm in length (FIG. 14A).

Following inactivation with a standard 3% $H_2O_2$ solution for 5 hours at room temperature, the bacteria were substantially damaged with clear changes in morphology, including loss of gross cellular structure and substantial clumping (FIG. 14B).

However, upon optimization of a dual-oxidation approach using 0.01% $H_2O_2$ and 2 µM $CuCl_2$, Applicants surprisingly found that dual oxidation could completely inactivate *Campylobacter coli* (*C. coli*) while maintaining excellent bacterial morphology throughout the treatment period with microbes that remained indistinguishable from the untreated controls (FIG. 14C).

Figure 15:
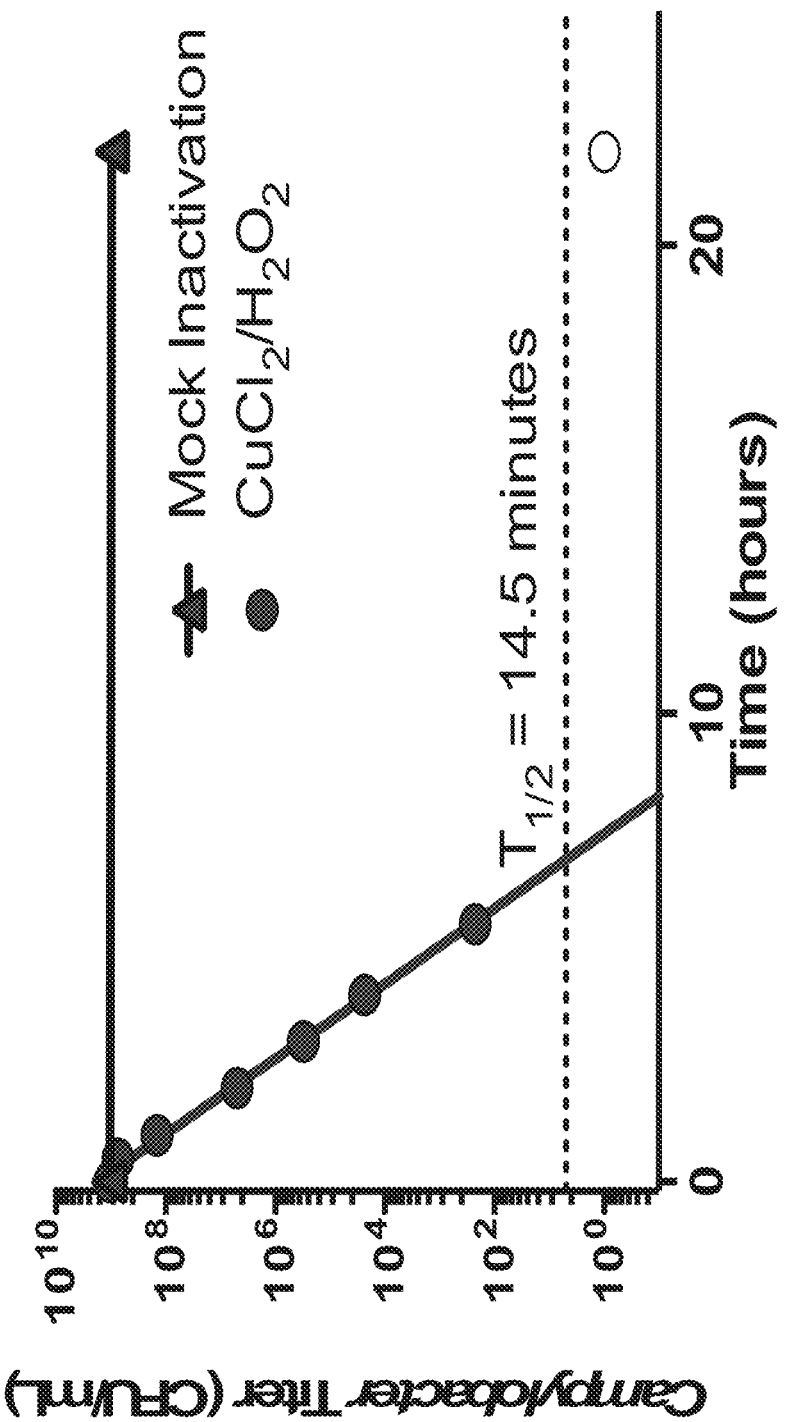
FIG. 15 shows, according to particular aspects, exposure to an optimized $CuCl_2$/$H_2O_2$ formula resulted in rapid inactivation of *Campylobacter*.

In addition to retained structure, a critical parameter for preparing an inactivated whole-cell vaccine is to ensure complete microbe inactivation. Using the optimal conditions described above, inactivation kinetic studies were performed. As shown in FIG. 15, *C. coli* demonstrated rapid inactivation, with a decay rate half-life of ($T_{1/2}$) of ~15 minutes. These kinetics indicate >20 logs of inactivation during the full 20-hr inactivation period. Based on the bacterial titers in the pilot manufacturing lots (~$10^9$ CFU/mL) this level of inactivation provides a high safety margin during the manufacturing process (up to 100 million-fold theoretical excess inactivation) while still maintaining overall bacterial structure (FIG. 14C).

$CuCl_2/H_2O_2$-*C. coli* Vaccination Provided Protective Immunity in Rhesus Macaques As shown herein under working Example 11, Applicants determined vaccine efficacy in 60 $CuCl_2/H_2O_2$-*C. coli*-immunized rhesus macaques from two outdoor sheltered housing groups, and then monitored the animals for *Campylobacter* culture-confirmed enteric disease.

For this study, animals were vaccinated intramuscularly with the $CuCl_2/H_2O_2$-*C. coli* vaccine candidate (inactivated using 0.01% $H_2O_2$ and 2 µM $CuCl_2$), with a booster dose administered 6-months later. Vaccinated groups were selected based on prior disease history, with preference given to groups that had historically high incidence rates of *Campylobacter* infection. This approach provided increased robustness in evaluating protective efficacy. All adults/juveniles (n=59) received a 40-µg alum-adjuvanted dose, with 2 small infants (<2 Kg body weight) receiving a half-dose (20-µg). According to protocol, any animal diagnosed with *Campylobacter*-associated diarrhea during the first 14 days after vaccination would be excluded since vaccine-mediated protection would be unlikely to occur during this early period. One adult animal was excluded from the study due to *Campylobacter*-associated diarrhea on the day after vaccination. Serum samples were collected from all remaining vaccinated animals (n=59) at day 0 and at 6 months after primary vaccination at which time the animals received a booster dose of vaccine.

Following primary vaccination, the Applicants observed a significant increase in *Campylobacter*-specific serum antibody titers (FIG. 16A, P<0.001) in addition to protection against *Campylobacter*-associated diarrheal disease in comparison with prior years within the same shelter group (FIG. 16B, P=0.038) or in comparison with other shelter groups during the 2015 *Campylobacter* season (FIG. 16C, P=0.020). The health of NHP are monitored daily and cases of diarrheal disease are documented in a searchable central database. Diarrhea incidence was monitored in the vaccinated cohort and compared to approximately 1,000 unvaccinated control animals in other similar shelter groups. Fecal samples were collected from any animal experiencing a diarrheal episode and tested for *C. coli, C. jejuni*, and *Shigella* spp. since these represent the main enteric pathogens associated with diarrhea among the animals.

Interim analysis at 6 months after primary vaccination demonstrated no cases of *C. coli* or *C. jejuni*-associated diarrhea in the vaccinated group versus 76 cases of *Campylobacter*-associated diarrhea among the unvaccinated animals, representing a statistically significant protective effect against *Campylobacter* culture-positive diarrheal disease (P=0.035) after a single vaccination.

Since nearly all human vaccines require at least two doses for optimal protective efficacy and the durability of immunological memory is often improved following booster vaccination, the Applicants followed the conservative approach of administering a booster vaccination at the 6 month time point and then continued to monitor the incidence of diarrheal disease among the NHP. At 250 days after primary vaccination, more cases of *Campylobacter*-associated enteric disease had continued to accrue among the unvaccinated population (reaching 8.7% or a total of 92 animals) whereas none of the animals (0/59) in the vaccinated cohort showed signs of disease and the statistical significance between the two groups increased to P=0.020.

Methisazone Reagents

As disclosed and discussed in detail above, oxidizing transition metals (e.g., $Cu^{2+}$, $Fe^{3+}$, etc.) can be used in conjunction with our peroxide-based vaccine development platform to enhance virus inactivation while limiting antigenic damage. However, for some pathogens it was noted that antigenic degradation can occur even when using this advanced dual-oxidation approach. To further improve vaccine development, additional compounds were searched/screened for the ability to interact synergistically with our disclosed dual-oxidation-based inactivation approach to increase the rate of inactivation while further reducing damage to immunogenic protein antigens. Through this search, methisazone (N-methylisatin β-thiosemicarbazone, CAS 1910-68-5; $C_{10}H_{10}N_4OS$; MWt 234.3 Da; Synonyms: metisazone; Marboran; Marborane; 33T57; M-IBT; 1-methylisatin 3-thiosemicarbazide; N-methylisatin β-thiosemicarbazone) was identified by Applicants. Methisazone is one of a series of antiviral drugs developed by the Wellcome Foundation in the 1950s (Thompson R L, et al., *J Immunol.* 1953; 70:229-34; Bauer D J., *Br J Exp Pathol.* 1955; 36:105-14). Based on small animal efficacy studies with orthopoxviruses, methisazone was developed into the commercial product, Marboran®, and tested in several clinical trials including both the treatment of vaccinia complications, as well as prophylaxis and treatment for smallpox (Bauer D J., *Ann N Y Acad Sci.* 1965; 130:110-7).

According to Bauer (Id), early case reports for the use of methisazone in the treatment of vaccinia complications (eczema vaccinatum and vaccinia gangrenosa) indicate it may have been effective, but the lack of controls and concomitant use of antivaccinial gamma globulin (in some cases) makes it challenging to confirm efficacy. Nevertheless, the lack of serious adverse events is encouraging. Mean initial doses were 152 mg/kg, with a total average dose of 809 mg/kg given over 3.75 days. For an estimated human subject weight of 70 kg, this would translate into ~10 gr per dose, and ~60 gr per treatment course. Bauer mentions that methisazone was used prophylactically prior to vaccinia vaccination, and was reported to reduce complications (Id).

Thus, historical in vivo data demonstrates that methisazone is safe and even trace amounts of this compound will not be an issue in new vaccine and drug products.

Some of the most impressive data for methisazone relates to smallpox prophylaxis as reported during an outbreak in Madras, India (Bauer D J et al., Lancet, 1963; 2:494-6). Of the close contacts receiving methisazone, only 3/1101 (0.27%) developed mild smallpox (no deaths), while 78/1126 (6.9%) developed smallpox, with 12 deaths. When focusing on only non-vaccinated subjects, 2/102 methisazone-treated subjects contracted smallpox (2%) while 28/100 (28%) of untreated controls contracted smallpox, with 11 deaths. Dosages were altered somewhat throughout the trial and consisted of either (1) 1.5 gr by mouth twice daily after meals for 4 days (12 gr total); (2) 3 gr by mouth twice daily after meals for 4 days (24 gr total); (3) two doses of 3 gr by mouth within a 12 hr period (6 gr total). Methisazone, in combination with $CuSO_4$, has been described for the decontamination of viruses (Fox M P, et al., *Ann N Y Acad Sci.* 1977; 284:533-43; Logan J C, et al., J Gen Virol. 1975; 28:271-83), but not for vaccine production, and has never been used in conjunction with $H_2O_2$.

Fenton-Type Chemistry Plus Methisazone Reagents

Surprisingly, Applicants discovered that methisazone reagents, as described herein, interact synergistically with the presently disclosed dual-oxidation-based inactivation approach to substantially increase the rate of inactivation while further reducing damage to immunogenic protein antigens.

In additional aspects, therefore, the disclosed dual-oxidation methods involving Fenton-type chemistry further comprise, as described in more detail below in the working Examples, the use of methisazone, methisazone analogs, or methisazone functional group(s)/substructure(s), providing even more efficient microbial inactivation relative to dual-oxidation alone, and with even more effective retention of immunogenicity relative to dual-oxidation alone.

The exact mode of action for methisazone in the disclosed methods is unclear, though studies have shown that methisazone can complex with copper, and this complex has the capacity to bind both nucleic acid (Mikelens P E, et al., *Biochem Pharmacol.* 1976; 25:821-7) and protein (Rohde W, et al., *J Inorg Biochem.* 1979; 10:183-94). To explain Applicants' results, without being bound by mechanism, Applicants hypothesized that the methisazone-copper complex might preferentially bind nucleic acid of the whole pathogen, and once bound, $H_2O_2$ may then interact with the $Cu^{2+}$ of the methisazone-copper complex in a classic Fenton-type reaction to release highly active hydroxyl radicals in the proximity of the bound nucleic acid (e.g., a nucleic acid-focused oxidation). This release of oxidative radicals may then lead to substantial, but localized, damage of the nucleic acid and inactivation of the pathogen. Applicants speculated, therefore, that lower amounts of $H_2O_2$ than would typically be needed to inactivate pathogens could be used, thus limiting off-site/collateral damage to protein epitopes. Additionally, or alternatively, isatin β-thiosemicarbazone compounds have also been shown to directly bind nucleic acid (Pakravan & Masoudian, *Iran J Pharm Res.* 2015; 14:111-23), suggesting that this class of compounds alone may be able to open up nucleic acid macromolecules (e.g., by intercalation, and/or minor groove binding). Applicant speculated that if this was true, it may allow for greater access of oxidizing agents to the nucleic acid target to enhance oxidation-based virus inactivation.

Figures 17A, 17B, 17C:
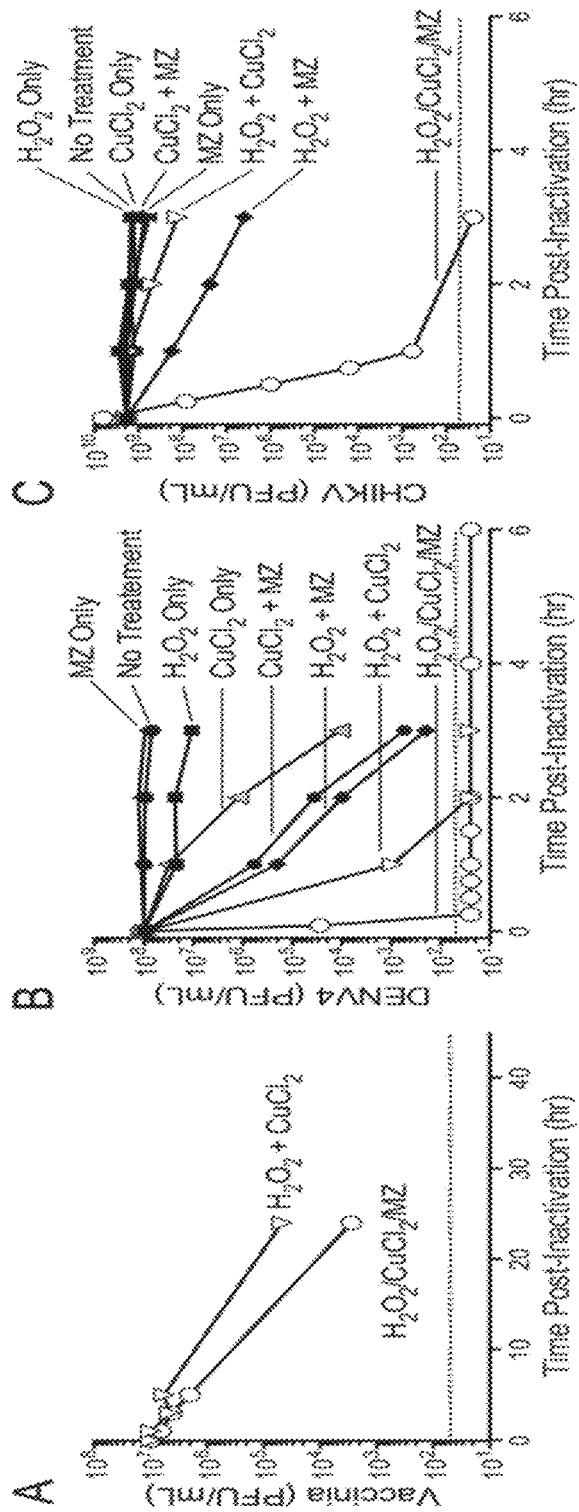
FIGS. 17A, 17B, and 17C show, according to particular aspects, that methisazone enhanced the rate of both single and dual oxidation-based virus inactivation.

Methisazone Enhanced the Rate of Both Single and Dual Oxidation-Based Virus Inactivation As shown herein under working Example 12, Applicants determined that methisazone enhanced the rate of both single and dual oxidation-based virus inactivation. As shown in FIGS. 17A-C, the addition of methisazone was able to substantially increase the rate of dual-oxidation-based inactivation for vaccinia virus (VV, DNA genome) as well as dengue virus serotype 4 (DENV4, RNA genome) and chikungunya virus (CHIKV, RNA genome).

Further, while methisazone alone had a minimal impact on virus inactivation (FIGS. 17B & 17C), methisazone and $H_2O_2$ together (even in the absence of copper) demonstrated a synergistic enhancement for virus inactivation. Further surprising aspects, therefore, provide effective single-oxidation methods involving hydrogen peroxide ($H_2O_2$) further comprising, as described in more detail below, the use of methisazone, methisazone analogs, or methisazone functional group(s)/substructure(s), providing for more efficient microbial inactivation relative to $H_2O_2$ alone, and with effective retention of immunogenicity.

Methisazone Enhanced the Rate of Dual Oxidation-Based Bacterial Inactivation

As shown herein under working Example 13, Applicants determined that methisazone enhanced the rate of dual oxidation-based bacterial inactivation.

The results of working Example 12 were extended to DNA-encoded bacteria (FIGS. 18A-C) where again the addition of methisazone to the dual-oxidation approach (e.g., $H_2O_2$/$CuCl_2$) substantially enhanced inactivation rates for *Campylobacter coli* (an exemplary gram-negative bacteria), *Listeria monocytogenes* (an exemplary gram-positive bacteria) and *Shigella dysenteriae* (an exemplary gram-negative bacteria).

Methisazone Enhanced Inactivation Rates while Maintaining Antigenicity During Dual Oxidation-Based Virus Inactivation As shown herein under working Example 14, Applicants determined that methisazone enhanced inactivation rates while maintaining antigenicity during dual oxidation-based virus inactivation. To assess the impact of methisazone on antigenicity during inactivation, the exemplary model viruses CHIKV and DENV4 were treated with multiple inactivation approaches: high concentration $H_2O_2$ (single oxidation system), dual-oxidation (as described herein), or dual-oxidation with methisazone. As shown by the ELISA data in FIG. 19A (Chikungunya virus (CHIKV)) and 19B (dengue virus serotype 4 (DENV4)), the addition of methisazone to the dual-oxidation approach maintained or significantly improved antigenicity by reducing damage to neutralizing epitopes, while increasing the rate of inactivation by approximately 10- to 20-fold.

Chemical Analogs of Methisazone, or Methisazone Functional Groups/Substructures or Combinations Thereof, Enhanced Inactivation and Maintenance of Antigenicity During Dual Oxidation-Based Viral Inactivation As shown herein under working Example 15, Applicants determined that chemical analogs of methisazone, or methisazone functional groups/substructures or combinations thereof, enhanced inactivation and maintenance of antigenicity during dual oxidation-based viral inactivation.

We tested several related compounds to determine if they provided similar enhancements to pathogen inactivation for vaccine development (FIGS. 20A-C). As shown with the exemplary model virus DENV4, several of these compounds, such as isatin β-thiosemicarbazone and N-propyl-isatin β-thiosemicarbazone, demonstrated results similar to methisazone including enhanced rates of inactivation while maintaining superior antigenicity in the dual-oxidation system. Interestingly, when using just the thiosemicarbazide moiety, we still observed enhancement of inactivation and superior antigenicity, whereas isatin or semicarbazide do not appear to increase the rate of inactivation, but still demonstrate protection of protein antigens from oxidative damage during inactivation. To explore if the separate major components (functional groups/substructures) of methisazone-related compounds could be combined in order recapitulate optimal inactivation, we tested mixtures of isatin+thiosemicarbazide or isatin+semicarbazide. While isatin+semicarbazide still demonstrated antigen protection, there was no enhancement of virus inactivation. By contrast, isatin+thiosemicarbazide resulted in both rapid inactivation (more rapid than either component alone) as well as greatly increased antigenicity.

Increasing Levels of Methisazone Relative to the Transition Metal Component of the Dual Oxidation System Improved the Antigenicity and Inactivation Profile of the Dual Oxidation System As shown herein under working Example 16, Applicants determined that increasing levels of methisazone relative to the transition metal component of the dual oxidation system improved the antigenicity and inactivation profile of the dual oxidation system.

The impact of relative concentrations of methisazone and the transition metal in the dual-oxidation system (FIG. 21) was examined. We found that increasing methisazone concentrations relative to the transition metal demonstrated concomitant improvements in both retained antigenicity and increased virus inactivation rates, with a preferred molar ratio of 10:1 (methisazone:transition metal).

the Dual Oxidation-Based Inactivation Methods, and Including Those Further Comprising Use of a Methisazone Reagent, have Broad Utility in the Development of Advanced Vaccines Against Pathogens Having Either RNA or DNA Genomes, Including but not Limited to Viral and Bacterial Pathogens As discussed above, and shown in the working examples herein, the dual oxidation-based inactivation methods, and including those further comprising use of a methisazone reagent, were shown to have utility across not only eight viruses in four different viral Families, but also for three exemplary bacterial species (e.g., *Campylobacter*, a Gram-negative bacteria, at least a dozen species of which have been implicated in human disease, with *C. jejuni* and *C. coli* being the most common), *Listeria monocytogenes* (an exemplary gram-positive bacteria) and *Shigella dysenteriae* (an exemplary gram-negative bacteria).

According to further aspects, the dual oxidation-based inactivation methods, and including those further comprising use of a methisazone reagent, have utility for producing highly immunogenic vaccines using, but not limited to the following exemplary microbes:

Viruses. Non-limiting examples of viruses that can be inactivated using dual oxidation include the following families: Adenoviridae, Alloherpesviridae, Alphaflexiviridae, Alphaherpesvirinae, Alphatetraviridae, Alvernaviridae, Amalgaviridae, Ampullaviridae, Anelloviridae, Arenaviridae, Arteriviridae, Ascoviridae, Asfarviridae, Astroviridae, Autographivirinae, Avsunviroidae, Baculoviridae, Barnaviridae, Benyviridae, Betaflexiviridae, Betaherpesvirinae, Bicaudaviridae, Bidnaviridae, Birnaviridae, Bornaviridae, Bromoviridae, Bunyaviridae, Caliciviridae, Carmotetraviridae, Caulimoviridae, Chordopoxvirinae, Chrysoviridae, Circoviridae, Clavaviridae, Closteroviridae, Comovirinae, Coronaviridae, Coronavirinae, Corticoviridae, Cystoviridae, Densovirinae, Dicistroviridae, Endornaviridae, Entomopoxvirinae, Eucampyvirinae, Filoviridae, Flaviviridae, Fuselloviridae, Gammaflexiviridae, Gammaherpesvirinae, Geminiviridae, Globuloviridae, Gokushovirinae, Guttaviridae, Hepadnaviridae, Hepeviridae, Herpesviridae, Hypoviridae, Hytrosaviridae, Iflaviridae, Inoviridae, Iridoviridae, Leviviridae, Lipothrixviridae, Luteoviridae, Malacoherpesviridae, Marnaviridae, Marseilleviridae, Megabirnaviridae, Mesoniviridae, Metaviridae, Microviridae, Mimiviridae, Myoviridae, Nanoviridae, Narnaviridae, Nimaviridae, Nodaviridae, Nudiviridae, Nyamiviridae, Ophioviridae, Orthomyxoviridae, Orthoretrovirinae, Papillomaviridae, Paramyxoviridae, Paramyxovirinae, Partitiviridae, Parvoviridae, Parvovirinae, Peduovirinae, Permutotetraviridae, Phycodnaviridae, Picobirnaviridae, Picornaviridae, Picornavirinae, Plasmaviridae, Pneumovirinae, Podoviridae, Polydnaviridae, Polyomaviridae, Pospiviroidae, Potyviridae, Poxviridae, Pseudoviridae, Quadriviridae, Reoviridae, Retroviridae, Rhabdoviridae, Roniviridae, Rudiviridae, Secoviridae, Sedoreovirinae, Siphoviridae, Sphaerolipoviridae, Spinareoviridae, Spiraviridae, Spounavirinae, Spumaretrovirinae, Tectiviridae, Tevenvirinae, Togaviridae, Tombusviridae, Torovirinae, Totiviridae, Turriviridae, Tymoviridae, and Virgaviridae.

Exemplary viral species include poliovirus, measles virus, mumps virus, parainfluenza virus, Newcastle disease virus, rubella virus, Eastern, Western and Venezuelan Equine Encephalitis Viruses, Lassa virus, lymphocytic choriomeningitis virus, West Nile virus, Dengue virus, Yellow fever virus, Tick-borne encephalitis virus, St. Louis encephalitis virus, Japanese Encephalitis virus, Zika virus, varicella zoster virus, cytomegalovirus, herpes simplex viruses, retroviruses including HIV (human immunodeficiency virus), hepatitis A virus, hepatitis B virus, hepatitis C virus, influenza viruses, rabies virus, molluscum contagiosum, smallpox virus, vaccinia virus, Sindbis virus, swine influenza virus, porcine parvovirus, porcine circovirus, chikungunya virus, porcine reproductive and respiratory syndrome virus, canine distemper virus, canine parvovirus, canine adenovirus Type-2, canine parainfluenzavirus, and canine coronavirus.

Bacteria. Bacterial pathogens can also be inactivated using dual oxidation, and including dual oxidation further comprising use of a methisazone reagent, for use in producing highly immunogenic vaccine compositions. Non-limiting examples of bacteria that can be inactivated using dual oxidation include the following families: Acanthopleuribacteraceae, Acetobacteraceae, Acholeplasmataceae, Acholeplasmataceae, Acidaminococcaceae, Acidilobaceae, Acidimicrobiaceae, Acidimicrobiaceae, Acidithiobacillaceae, Acidobacteriaceae, Acidothermaceae, Actinomycetaceae, Actinopolysporaceae, Actinospicaceae, Actinosynnemataceae, Aerococcaceae, Aeromonadaceae, Akkermansiaceae, Alcaligenaceae, Alcaligenaceae, Alcanivoracaceae, Algiphilaceae, Alicyclobacillaceae, Alteromonadaceae, Anaerolineaceae, Anaeroplasmataceae, Anaeroplasmataceae, Anaplasmataceae, Aquificaceae, Aquificaceae, Archaeoglobaceae, Armatimonadaceae, Aurantimonadaceae, Bacillaceae, Bacteriovoracaceae, Bacteroidaceae, Bacteroidaceae, Bartonellaceae, Bartonellaceae, Bdellovibrionaceae, Beijerinckiaceae, Beijerinckiaceae, Beutenbergiaceae, Bifidobacteriaceae, Blattabacteriaceae, Bogoriellaceae, Brachyspiraceae, Bradyrhizobiaceae, Bradyrhizobiaceae, Brevibacteriaceae, Brevinemataceae, Brucellaceae, Brucellaceae, Burkholderiaceae, Burkholderiaceae, Caldicoprobacteraceae, Caldilineaceae, Caldisericaceae, Caldisphaeraceae, Campylobacteraceae, Cardiobacteriaceae, Carnobacteriaceae, Caryophanaceae, Catalimonadaceae, Catenulisporaceae, Caulobacteraceae, Caulobacteraceae, Celerinatantimonadaceae, Cellulomonadaceae, Chitinophagaceae, Chlamydiaceae, Chlamydiaceae, Chlorobiaceae, Chlorobiaceae, Chloroflexaceae, Christensenellaceae, Chromatiaceae, Chrysiogenaceae, Chrysiogenaceae, Chthonomonadaceae, Clostridiaceae, Cohaesibacteraceae, Colwelliaceae, Comamonadaceae, Comamonadaceae, Conexibacteraceae, Coriobacteriaceae, Coriobacteriaceae, Corynebacteriaceae, Coxiellaceae, Crenotrichaceae, Cryomorphaceae, Cryptosporangiaceae, Cyclobacteriaceae, Cystobacteraceae, Cytophagaceae, Deferribacteraceae, Deferribacteraceae, Defluviitaleaceae, Dehalococcoidaceae, Deinococcaceae, Demequinaceae, Dermabacteraceae, Dermacoccaceae, Dermatophilaceae, Desulfarculaceae, Desulfobacteraceae, Desulfobulbaceae, Desulfohalobiaceae, Desulfomicrobiaceae, Desulfonatronaceae, Desulfovibrionaceae, Desulfurellaceae, Desulfurobacteriaceae, Desulfurococcaceae, Desulfuromonadaceae, Dictyoglomaceae, Dictyoglomaceae, Dietziaceae, Ectothiorhodospiraceae, Ehrlichiaceae, Elusimicrobiaceae, Enterobacteriaceae, Enterococcaceae, Entomoplasmataceae, Entomoplasmataceae, Erysipelotrichaceae, Erysipelotrichaceae, Erythrobacteraceae, Eubacteriaceae, Euzebyaceae, Ferrimonadaceae, Ferroplasmaceae, Fervidicoccaceae, Fibrobacteraceae, Fimbriimonadaceae, Flammeovirgaceae, Flavobacteriaceae, Flexibacteraceae, Francisellaceae, Frankiaceae, Fusobacteriaceae, Fusobacteriaceae, Gaiellaceae, Gallionellaceae, Gemmatimonadaceae, Geobacteraceae, Geodermatophilaceae, Glycomycetaceae, Gordoniaceae, Gracilibacteraceae, Granulosicoccaceae, Hahellaceae, Halanaerobiaceae, Halobacteriaceae, Halobacteroidaceae, Halomonadaceae, Haloplasmataceae, Halothiobacillaceae, Helicobacteraceae, Heliobacteriaceae, Herpetosiphonaceae, Holophagaceae, Holosporaceae, Holosporaceae, Hydrogenophilaceae, Hydrogenophilales, Hydrogenothermaceae, Hydrogenothermaceae, Hyphomicrobiaceae, Hyphomicrobiaceae, Hyphomonadaceae, lamiaceae, Idiomarinaceae, Ignavibacteriaceae, Intrasporangiaceae, Jiangellaceae, Jonesiaceae, Kiloniellaceae, Kineosporiaceae, Kofleriaceae, Kordiimonadaceae, Ktedonobacteraceae, Lachnospiraceae, Lactobacilluseae, Legionellaceae, Lentisphaeraceae, Leptospiraceae, Leptospiraceae, Leptotrichiaceae, Leuconostocaceae, Listeriaceae, Litoricolaceae, Magnetococcaceae, Marinilabiliaceae, Methanobacteriaceae, Methanocaldococcaceae, Methanocellaceae, Methanococcaceae, Methanocorpusculaceae, Methanomicrobiaceae, Methanopyraceae, Methanoregulaceae, Methanosaetaceae (illegitimate), Methanosarcinaceae, Methanospirillaceae, Methanothermaceae, Methermicoccaceae, Methylobacteriaceae, Methylobacteriaceae, Methylococcaceae, Methylocystaceae, Methylocystaceae, Methylophilaceae, Methylophilaceae, Microbacteriaceae, Micrococcaceae, Micromonosporaceae, Microsphaeraceae, Mooreiaceae, Moraxellaceae, Moritellaceae, Mycobacteriaceae, Mycoplasmataceae, Mycoplasmataceae, Myroidaceae, Myxococcaceae, Nakamurellaceae, Nannocystaceae, Natranaerobiaceae, Nautiliaceae, Neisseriaceae, Nevskiaceae, Nitriliruptoraceae, Nitrosomonadaceae, Nitrospinaceae, Nocardiaceae, Nocardioidaceae, Nocardioidaceae, Nocardiopsaceae, Oceanospirillaceae, Oleiphilaceae, Oligosphaeraceae, Opitutaceae, Orbaceae, Oscillochloridaceae, Oscillospiraceae, Oxalobacteraceae, Oxalobacteraceae, Paenibacillaceae, Parachlamydiaceae, Parachlamydiaceae, Parvularculaceae, Pasteurellaceae, Pasteuriaceae, Patulibacteraceae, Peptococcaceae, Peptostreptococcaceae, Peredibacteraceae, Phaselicystidaceae, Phycisphaeraceae, Phyllobacteriaceae, Phyllobacteriaceae, Picrophilaceae, Piscirickettsiaceae, Planctomycetacea, Planctomycetaceae, Planococcaceae, Polyangiaceae, Porphyromonadaceae, Porphyromonadaceae, Prevotellaceae, Prevotellaceae, Promicromonosporaceae, Propionibacteriaceae, Pseudoalteromonadaceae, Pseudomonadaceae, Pseudonocardiaceae, Psychromonadaceae, Puniceicoccaceae, Pyrodictiaceae, Rarobacteraceae, Rhabdochlamydiaceae, Rhizobiaceae, Rhizobiaceae, Rhodobacteraceae, Rhodobacteraceae, Rhodobiaceae, Rhodobiaceae, Rhodocyclaceae, Rhodospirillaceae, Rhodospirillaceae, Rhodothermaceae, Rickettsiaceae, Rickettsiaceae, Rikenellaceae, Rikenellaceae, Roseiflexaceae, Ruaniaceae, Rubritaleaceae, Rubrobacteraceae, Rubrobacteraceae, Ruminococcaceae, Sandaracinaceae, Sanguibacteraceae, Saprospiraceae, Schleiferiaceae, Segniliparaceae, Serpulinaceae, Shewanellaceae, Simkaniaceae, Simkaniaceae, Sinobacteraceae, Sneathiellaceae, Solimonadaceae, Solirubrobacteraceae, Sphaerobacteraceae, Sphaerobacteraceae, Sphingobacteriaceae, Sphingomonadaceae, Sphingomonadaceae, Spirillaceae, Spirochaetaceae, Spirochetaceae, Spiroplasmataceae, Spiroplasmataceae, Sporichthyaceae, Sporolactobacilloceae, Staphylococcaceae, Streptococcaceae, Streptomycetaceae, Streptosporangiaceae, Succinivibrionaceae, Sulfolobaceae, Sutterellaceae, Synergistaceae, Syntrophaceae, Syntrophobacteraceae, Syntrophomonadaceae, Syntrophorhabdaceae, Thermaceae, Thermithiobacillaceae, Thermoactinomycetaceae, Thermoanaerobacteraceae, Thermoanaerobacteriaceae, Thermococcaceae, Thermodesulfobacteriaceae, Thermodesulfobacteriaceae, Thermodesulfobiaceae, Thermofilaceae, Thermogemmatisporaceae, Thermoleophilaceae, Thermolithobacteraceae, Thermomicrobiaceae, Thermomonosporaceae, Thermoplasmataceae, Thermoproteaceae, Thermosporotrichaceae, Thermotogaceae, Thioalkalispiraceae, Thiotrichaceae, Trueperaceae, Tsukamurellaceae, Turicibacteraceae, Veillonellaceae, Verrucomicrobiaceae, Verrucomicrobiaceae, Vibrionaceae, Victivallaceae, Waddliaceae, Waddliaceae, Williamsiaceae, Xanthobacteraceae, Xanthomonadaceae, Yaniellaceae, Aurantimonadaceae, Cenarchaeaceae, Haliangiaceae, Hydrogenimonaceae, Kordiimonadaceae, Mariprofundaceae, Nitrospiraceae, Parvularculaceae, Procabacteriaceae, Saccharospirillaceae, and Salinisphaeraceae.

Exemplary bacterial species include *Campylobacter* species (spp.), *Shigella* spp., *Mycobacterium* spp., *Neisseria* spp., *Brucella* spp., *Borrelia* spp., *Chlamydia* spp., *Listeria monocytogenes, Bordatella pertussis, Clostridium* spp., *Enterococcus* spp., *Escherichia* spp., *Francisella tularensis, Haemophilus influenzae, Helicobacter pylori, Legionella pneumophila, Leptospira interrogans, Streptococcus pneumoniae, Pseudomonas aeruginosa, Rickettsia rickettsii, Salmonella* spp., *Staphylococcus aureus*, and *Bacillum anthracis*. Gram-positive and Gram-negative bacteria, for example, are generally encompassed.

Fungi. Highly immunogenic vaccine compositions can also be produced from fungal pathogens inactivated using dual oxidation. Exemplary fungal pathogens include: *Aspergillus* spp., *Candida* spp, *Blastomyces* spp., *Coccidioides* spp., *Cryptococcus* spp., *Fusarium* spp., *Histoplasma* spp., Mucorales spp., *Pneumocystis* spp., *Trichophyton* spp., *Epidermophyton* spp., *Microsporum* spp, *Sporothrix* spp., *Exserohilum* spp., and *Cladosporium* spp.

Parasites. The methods disclosed herein can also be used to inactivate parasites (e.g., intracellular parasites) for highly immunogenic vaccines, and especially protozoan parasites, such as *Plasmodium falciparum* and other *Plasmodium* spp., *Leishmania* spp., *Cryptosporidium parvum, Entamoeba histolytica*, and *Giardia lamblia, Trypanosoma* spp., as well as *Toxoplasma, Eimeria, Theileria*, and *Babesia* species.

Immunogenic Compositions

Using the disclosed methods, immunogenic compositions, such as vaccines containing an inactivated pathogen as also provided. For example, the composition (or medicament) can be a lyophilized immunogenic composition (for example, vaccine preparation) containing a pathogen that retains one or more predominant antigenic epitopes of the biologically active pathogen from which it was prepared. The lyophilized composition may be prepared preservative-free and devoid of any inactivating agent (e.g., devoid of $H_2O_2$, etc.). The composition can also be a liquid prepared by reconstituting a lyophilized composition in a pharmaceutically acceptable diluent. Optionally, the composition can include a suitable adjuvant that increases the antigenic efficacy of the antigen.

Inactivation with the presently disclosed dual oxidation approach, and including those further comprising use of a methisazone reagent, not only provides improved methods for vaccine production, including for pathogens for which effective vaccines cannot be produced by other methods (including by peroxide alone), but also provides several additional significant benefits as compared to UV inactivation, heat inactivation or inactivation with formaldehyde or betapropiolactone.

First, dual oxidation with hydrogen peroxide plus transition metals ions (Fenton type reaction), and including dual oxidation further comprising use of a methisazone reagent, is significantly better than any of the other methods at maintaining immunogenic epitopes. Thus, dual oxidation inactivation, and including dual oxidation further comprising use of a methisazone reagent, produces highly effective immunogenic compositions, such as vaccines, which can be used to produce an immune response that is far more likely to be protective against subsequent infection by the live pathogen than are vaccines produced using methods that denature or destroy immunologically important epitopes.

Second, unlike other chemical inactivating agents, such as formaldehyde or betapropiolactone, the Cu and Fe ions used in the presently disclosed dual oxidation methods are not only naturally occurring in subjects, but are present in the reactions in non-toxic amounts. Moreover, residual transition metals, and/or methisazone reagents, can be removed by downstream purification using, for example, anion exchange chromatography, flow filtration (e.g., tangential flow filtration), size exclusion chromatography, desalting columns, diafiltration, dialysis, ultracentrifugation, sucrose gradient purification, high pressure liquid chromatography (HPLC), etc.

Likewise, any residual hydrogen peroxide can be substantially or completely removed from the vaccine composition by either using subsequent purification steps as described above for optional transition metal removal, or by using lyophilization. For example, a solution containing a pathogen and hydrogen peroxide and transition metal ions can be dispensed into sterile vials and lyophilized. During the lyophilization process, hydrogen peroxide is removed in vapor form, leaving behind a stable and sterile vaccine composition, which can easily be stored until it is needed. Lyophilization removes some, most or even all detectable hydrogen peroxide from the vaccine composition, and where desired produces a vaccine composition that is substantially free of hydrogen peroxide. Lyophilization can be performed by essentially any methods known in the art so long as the temperature is maintained below that at which heat denaturation of immunogenic epitopes occurs. Thus, the lyophilization can be performed following pre-freezing of the hydrogen peroxide/pathogen solution) or without pre-freezing (for example, at ambient temperatures above freezing, e.g., using a SPEED-VAC® concentrator under conditions that maintain the ambient temperature between about 0-4° C. and about 42° C.). For the purpose of manufacturing immunogenic compositions, such as vaccines, for administration to human or animal subjects, lyophilization is typically carried out according to current good manufacturing procedures (cGMP) for the production of vaccines. The inactivation and lyophilization can be accomplished without any intervening processing step, such as dilution, dialization, centrifugation, or purification. So long as the pathogen/hydrogen peroxide solution is dispensed (or aliquoted) into clean, sterile containers (e.g., vial, ampules, tubes, etc.) prior to lyophilization, the resulting vaccine composition is sterile, and no additional preservative need be added prior to administration. For example, if the vaccine composition is to be administered in a single dose, the lyophilized vaccine composition is simply suspended (or dissolved) in a pharmaceutically acceptable diluent to produce a preservative-free liquid vaccine composition. In the event that the lyophilized vaccine composition is intended for multiple administrations (for example, multiple sequential administration to a single subject, or one or more administrations to multiple subjects) the diluent can include a pharmaceutically acceptable preservative.

If desired, transition metal ions and/or hydrogen peroxide can be removed by purification steps as described above. For example, residual $H_2O_2$ and transition metals (e.g., either Cu or Fe) can be removed by use of one or more purification approaches such as tangential flow filtration, dialysis, desalting columns, ion-exchange chromatography (under conditions that bind the virus but not the residual inactivation components), affinity chromatography, size exclusion chromatography, etc.

Alternatively, sodium bisulfite ($NaHSO_3$) and/or sodium metabisulfite ($Na_2S_2O_5$) can both be used to neutralize $H_2O_2$ (1 mol of metabisulfite breaks down to two mols of bisulfite, which then reacts directly with $H_2O_2$).

$$Na_2S_2O_5 + 2H_2O \rightarrow 2NaHSO_3 + H_2O \quad (1)$$

$$2NaHSO_3 + 2H_2O_2 \rightarrow 2NaHSO_4 + 2H_2O \quad (2)$$

Prior to use, the vaccine can be reconstituted using a pharmaceutically acceptable diluent to facilitate delivery by conventional administration means. This enables the production of a sterile vaccine composition that does not contain harmful amounts of toxic and carcinogenic compounds, thereby increasing the safety of the vaccine.

Additionally, following dual oxidation inactivation, or dual oxidation further comprising use of a methisazone reagent, there is no need to add a preservative (such as thimerosal) to the resulting vaccine composition. The sterile composition can be maintained for long periods of time (e.g., in the lyophilized state), making addition of potentially toxic preservatives unnecessary. Thus, the compositions can be made to be substantially or completely free of preservatives. Optionally, preservatives can be provided in the composition.

The dual oxidation methods, and including those further comprising use of a methisazone reagent, provide immunogenic compositions, such as a vaccine, and thus provide methods for preparing a medicament that includes an inactivated pathogen. The methods provide compositions that contain an immunologically active noninfectious pathogen that retains predominant immunological epitopes of the infectious pathogen from which it is produced. Typically, the inactivated pathogen retains one, or more than one, immunologically dominant epitopes that elicit a protective immune response against the pathogen. This method is suitable for producing an immunogenic composition (for example, a vaccine) containing inactivated pathogens, including viruses, bacteria, fungi and parasites, such as intracellular parasites (for example, protozoan parasites). Optionally, the compositions contain more than one species or strain of pathogen, for example, combination vaccines can be produced using the methods. The compositions can include a plurality of viruses, e.g., mumps virus, measles virus and rubella virus, and/or other viruses as disclosed herein. Similarly, the composition can include a plurality of bacteria, e.g., *Campylobacter* species (spp.), *Corynebacterium diphtheriae, Bordetella pertussis* and *Clostridium tetani*, the causative agents of diarrhea, diphtheria, whooping cough and tetanus, respectively, and/or other bacterial as disclosed herein. The composition can also include a plurality of pathogens selected from different classifications (families) of organisms.

The dual oxidation methods involve contacting the pathogen with a solution containing an effective amount of the dual oxidizing agent (e.g., Fenton reagents; hydrogen peroxide ($H_2O_2$) plus transition metal ions), or with the dual oxidizing agent and a methisazone reagent, for a period sufficient to render the pathogen noninfectious. Optionally, the pathogen is purified or isolated prior to contacting with the dual oxidizing agent.

Typically, the solution includes at least about 0.001% or 0.002% hydrogen peroxide (wt/vol), and may contain up to about 0.10% hydrogen peroxide. Typically, the solution includes at least 1 μM or 2 μM transition metal (e.g., $CuCl_2$). Most typically, at least 0.001% or 0.002% hydrogen peroxide (wt/vol) is used in combination with at least 1 μM or 2 μM transition metal (e.g., $CuCl_2$). For example, the solution can include about 0.002% hydrogen peroxide (wt/vol), and about 1 μM or 2 μM $CuCl_2$. In further embodiments, the hydrogen peroxide concentration can be as low as 0.0001%, or as high 1.0%, in combination with above-described levels of transition metal. The concentration range of transition metals can be as low as 0.001 μM, or as high as 1000 μM, again with any of the disclosed levels of hydrogen peroxide. In reactions comprising a methisazone reagent, the preferred amount of methisazone reagent, methisazone analogs, or chemicals representing methisazone functional groups or methisazone functional substructures can be as low as 0.01 μM, or as high as 10,000 μM with any of the disclosed levels of hydrogen peroxide or transition metals.

While the mechanism of the dual-oxidation inactivation was found to be surprisingly different (i.e., found to be protein concentration-dependent) than that of simple hydrogen peroxide mediated oxidation, present Applicants have nonetheless found that the absolute and/or relative amounts of hydrogen peroxide (wt/vol) and transition metal ions (e.g., $CuCl_2$) can be varied and adjusted to optimize inactivation while retaining immunogenicity for a broad array of pathogens. Applicants have found that having two variables (hydrogen peroxide concentration; and transition metal concentration) to vary, and even three variables in reaction using a methisazone reagent, provides an enhanced fine tuning ability over prior art methods using a single agent. Moreover, Applicants have surprisingly found (as shown herein under the working examples), that the two Fenton components (hydrogen peroxide concentration; and transition metal concentration), as well as the methisazone reagents in reactions including them, act in synergy to provide results not achievable using single agents alone. Additionally, combinations of transition metals (e.g., $CuCl_2$ ($Cu^{2+}$), $FeCl_3$ ($Fe^{3+}$) or CsCl ($Cs^+$)), and methisazone reagents can be employed to exploit synergistic effects. For example, at $CuCl_2$ concentrations of 0.05 µM and 0.10 µM, increasing $FeCl_3$ concentrations enhanced antigenicity, indicating synergy with these two metals. These fine-tuning and synergistic aspects support a broad utility for the presently disclosed dual oxidation approach.

The length of time sufficient to completely inactivate a pathogen can vary between several minutes and several hours. For example, the pathogen can be contacted with the dual oxidation solution, or the dual oxidation solution further comprising a methisazone reagent, for a time within a range of about 1 hour to 24 hours, or shorter periods. Typically, for dual oxidation reactions, about 20 hours (plus or minus 2 hours) is used when using at least 0.001% or 0.002% hydrogen peroxide (wt/vol) is used in combination with at least 1 μM or 2 μM transition metal (e.g., $CuCl_2$). Generally, the length of time sufficient to inactivate the pathogen is dependent on the particular pathogen, and the concentration of reagents, and one of ordinary skill in the art will be able to empirically determine the concentration of reagents, the length of reaction time required, and the reaction temperature, based on the present disclosed teachings. In further embodiments, the hydrogen peroxide concentration can be as low as 0.0001%, or as high as 1.0%, in combination with above-described levels of transition metal. The concentration range of transition metals can be as low as 0.001 μM, or as high as 1000 μM, again with any of the disclosed levels of hydrogen peroxide. The preferred concentration of the methisazone reagent, methisazone analogs, or chemicals representing methisazone functional groups or methisazone functional substructures can be as low as 0.01 μM, or as high as 10,000 μM with any of the disclosed levels of hydrogen peroxide or transition metals.

The pathogen inactivation can be carried out at any temperature between freezing and the temperature at which immunologically relevant epitopes are denatured. Most commonly, the inactivation process is carried out at or above 4° C. and below about 42° C. For example, it is often convenient to perform the inactivation at room temperature or about 25° C.

Generally speaking, the dual oxidation conditions, including those further comprising a methisazone reagent, are determined to provide a high safety margin during the manufacturing process (e.g., up to 100 million-fold theoretical excess inactivation) while still maintaining overall antigenic structure.

The inactivated pathogen can then be stored for prolonged periods (for example, for more than several months or more than 1 year). The solution containing the inactivated pathogen can then be administered directly to a subject for the purpose of eliciting an immune response against the pathogen, for example, as a vaccine. More commonly, the solution including the inactivated pathogen is further processed or lyophilized, as described above, to produce an immunogenic composition.

The disclosure, therefore, provides immunogenic (e.g., vaccine) compositions produced according to the methods disclosed herein. For example, the composition (e.g., a medicament) is a lyophilized and/or purified composition including an inactivated pathogen that retains one or more predominant antigenic epitope of the biologically active pathogen. Typically, the composition is substantially or completely free of any preservative or inactivating agent, such as hydrogen peroxide, formaldehyde or betapropiolactone. In another embodiment, the composition is a liquid produced by suspending or dissolving (solubilizing) the lyophilized, or purified composition in a pharmaceutically acceptable diluent. Optionally, the diluent contains a preservative. Optionally, the vaccine composition includes an adjuvant. In lyophilized form, the adjuvant can be, for example, an aluminum (e.g., alum or an aluminum salt) adjuvant. Upon preparation of a liquid formulation from the lyophilized vaccine composition, the adjuvant can be a lipid formulation (e.g., an oil capable of forming an emulsion). The inactivated pathogen genome may comprise RNA or DNA.

Methods for Eliciting an Immune Response in a Subject by Administering the Compositions Containing Inactivated Pathogen are Also Provided According to additional aspects, methods of eliciting an immune response against a pathogen by administering the immunogenic compositions are provided. Typically, the immune response is a protective immune response that prevents or reduces infection by one or more pathogens. For example, an immune response can be elicited in a subject by preparing a composition by contacting a pathogen with a solution containing the dual oxidation reagent(s) for a period sufficient to render the pathogen noninfectious (while retaining immunogenicity); and administering the composition to a subject, thereby eliciting in the subject an immune response (e.g., a protective immune response) against the pathogen. In some applications the solution is administered to a subject without removing dual oxidation agent(s) from the solution. In other applications, the composition is lyophilized and/or otherwise purified as described herein, removing some or all (or substantially all) of the dual oxidation reagent(s). The processed composition can be administered in powder form (for example, as a dispersed powder or as a pellet, e.g., using the POWDERJECT® transdermal powder injection device). Alternatively, the lyophilized composition is reconstituted in a pharmaceutically acceptable diluent for administration using any method suitable for delivering a vaccine to a subject, e.g., intramuscular, intradermal, transdermal, subcutaneous or intravenous injection, oral delivery, or intranasal or other mucosal delivery of the immunogenic composition (e.g., vaccine).

Terms

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew, et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratis, and is used herein to indicate a non-limiting example. Thus, the abbreviation "e.g." is synonymous with the term "for example.

In order to facilitate review of the various embodiments of this disclosure, the following explanations of specific terms are provided:

"An immunogenic composition" or "vaccine composition" or "vaccine" is a composition of matter suitable for administration to a human or animal subject that is capable of eliciting a specific immune response, e.g., against a pathogen. As such, an immunogenic composition or vaccine includes one or more antigens or antigenic epitopes. The antigen can be in the context of an isolated protein or peptide fragment of a protein, or can be a partially purified preparation derived from a pathogen. Alternatively, the antigen can be in the context of a whole live or inactivated pathogen. Typically, when an immunogenic composition or vaccine includes a live pathogen, the pathogen is attenuated, that is, incapable of causing disease in an immunologically competent subject. In other cases, an immunogenic composition or vaccine includes a whole inactivated (or killed) pathogen. The inactivated pathogen can be either a wild-type pathogenic organism that would otherwise (if not inactivated) cause disease in at least a portion of immunologically competent subjects, or an attenuated or mutant strain or isolate of the pathogen. In the context of this disclosure, the immunogenic and/or vaccine compositions contain a whole (wild-type, attenuated or mutant) pathogen.

An "immune response" is a response of a cell of the immune system, such as a B cell, T cell, or monocyte, to a stimulus. In some cases, an immune response is a T cell response, such as a CD4+ response or a CD8+ response. Alternatively, the response is a B cell response, and results in the production of specific antibodies. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to viral challenge in vivo.

An "immunologically effective amount" is a quantity of a composition used to elicit an immune response in a subject. In the context of a vaccine administration, the desired result is typically a protective pathogen-specific immune response. However, to obtain protective immunity against a pathogen in an immunocompetent subject, multiple administrations of the vaccine composition are commonly required. Thus, in the context of this disclosure, the term immunologically effective amount encompasses a fractional dose that contributes in combination with previous or subsequent administrations to attaining a protective immune response.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond.

The "predominant antigenic epitopes" are those epitopes to which a functionally significant host immune response, e.g., an antibody response or a T-cell response, is made. Thus, with respect to a protective immune response against a pathogen, the predominant antigenic epitopes are those antigenic moieties that when recognized by the host immune system result in protection from disease caused by the pathogen.

The term "antigenicity" refers to the relative maintenance of immunogenic epitope structure(s) as determined, for example, by various in vitro measurements, such as binding of specific monoclonal antibodies or hemagglutination assays. "Antigenicity" in the in vivo context is typically referred to herein as "immunogenicity".

An "adjuvant" is an agent that enhances the production of an immune response in a non-specific manner. Common adjuvants include suspensions of minerals (e.g., alum, aluminum hydroxide, aluminum phosphate) onto which antigen is adsorbed; or water-in-oil emulsions in which an antigen solution is emulsified in oil (MF-59, Freund's incomplete adjuvant). Additional details regarding various adjuvants can be found in Derek O'Hagan Vaccine Adjuvants: Preparation Methods and Research Protocols (Methods in Molecular Medicine) Humana Press, 2000.

The term "pathogen" as used herein refers to an organism having either an RNA or DNA genome, and encompasses viruses (both RNA and DNA genome-based), bacteria (DNA genome-based, both Gram-positive and Gram-negative), fungi, and parasites. In particular preferred aspects, "pathogen" refers to an organism having either an RNA or DNA genome, and encompasses viruses (both RNA and DNA genome-based), and bacteria (DNA-genome based, both Gram-positive and Gram-negative).

The term "whole pathogen" refers to a pathogenic organism, such as a virus, a bacterium, a fungus or a parasite, that includes all or substantially all of the constituents of the infectious form of the organism. Typically, a whole pathogen is capable of replication. The term "whole pathogen" is nonetheless distinct from the term "wild-type" pathogen, and the term "whole pathogen" encompasses wild-type as well as attenuated and other mutant forms of the pathogenic organism. Thus, a whole pathogen can be an attenuated pathogen incapable of causing disease in an immunocompetent host, but nonetheless including all or substantially all of the constituents of an infectious pathogen. Similarly, a whole pathogen can be a mutant form of the pathogen, lacking one or more intact (wild-type) genes, and/or proteins. The pathogen genome may comprise RNA or DNA.

An "inactivated pathogen" is a whole pathogen that has been rendered incapable of causing disease (e.g., rendered noninfectious) by artificial means. Typically, an inactivated pathogen is a "killed pathogen" that is incapable of replication. A pathogen is noninfectious when it is incapable of replicating or incapable of replicating to sufficient levels to cause disease.

An "immunogenically active vaccine", as used herein in connection with Applicants' methods, is a pathogen inactivated by the disclosed methods that is capable of eliciting an immune response when introduced into an immunologically competent subject. The immune response produced in response to exposure to an immunogenically active vaccine comprising the inactivated pathogen as disclosed herein is preferably identical, substantially identical, or superior with respect to that produced by the predominant antigenic epitopes of the respective infectious pathogen.

"Hydrogen peroxide" ($H_2O_2$) is an exemplary preferred oxidizing agent with a standard electrode potential of 1.78 volts. For the purpose of consistency, the proportion of hydrogen peroxide in a solution, as in the working Examples disclosed herein, is given as weight per volume (wt/vol). For example 0.01% $H_2O_2$ refers to $H_2O_2$ being present at 0.01% wt/vol.

A "dual oxidizing agent" as used herein refers to a Fenton-type dual oxidation reagent comprising hydrogen peroxide and at least one transition metal (e.g., $CuCl_2$ ($Cu^{2+}$), $FeCl_3$ ($Fe^{3+}$) or CsCl ($Cs^+$)).

A "solution comprising the dual oxidizing agent(s)" includes the combination of any mixture of a solvent and dual oxidizing agent(s). Most commonly, in the context of the methods disclosed herein the solvent is water, e.g., deionized water, or an aqueous buffered salt solution. Typically, the term solution includes liquid phase solutions. For the purpose of consistency, the proportion of hydrogen peroxide in a solution is given as weight per volume (wt/vol).

The phrase "substantially free of hydrogen peroxide" indicates that no more than trace amounts (amounts empirically detectable as background) are present in the composition.

The verb "lyophilize" means to freeze-dry under vacuum. The process is termed "lyophilization." In some cases, the sample to be dried (e.g., dehydrated) is frozen prior to drying. In other cases, the material to be dried is subjected to the drying process without prior phase change. During the process of lyophilization, evaporation of the solvent results in cooling of the sample to temperatures below the melting temperature of the solvent/solute mixture resulting in freezing of the sample. Solvent is removed from the frozen sample by sublimation. A product that has undergone lyophilization is "lyophilized." As used in this disclosure the term lyophilization also encompasses functionally equivalent procedures that accelerate the drying process without exposing the sample to excessive heat, specifically including: spray drying and spray freeze-drying.

The term "methisazone" and "methisazone analog" as used herein in particular aspects refers to compounds having the following formula:

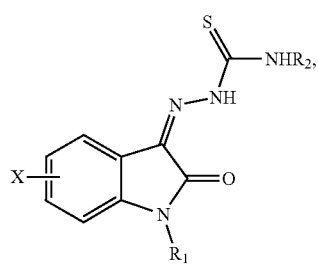

(I)

wherein $R_1$ is independently H or lower alkyl (e.g., C1-C4 alkyl) optionally substituted with —OH, for example, wherein $R_1$ is H, —$CH_3$, or propyl, etc.; wherein $R_2$ is independently H, lower alkyl (e.g., C1-C2 alkyl) optionally substituted with —OH, or aryl; wherein X is independently H or halogen (e.g., I, Br, Cl, F); and salts, including pharmaceutically acceptable salts, thereof. Preferably, wherein X and $R_2$ are H; and wherein $R_1$ is H (isatin β-thiosemicarbazone), —$CH_3$ (N-methyl-isatin β-thiosemicarbazone (methisazone)), or propyl (N-propyl-isatin β-thiosemicarbazone). Preferably, methisazone is used:

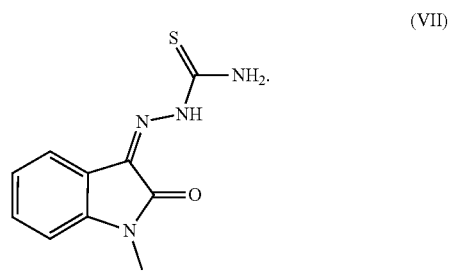 [SMILES: CN1C(=O)/C(=N\NC(N)=S)c2ccccc21]

(VII)

The term "methisazone functional group" or "methisazone functional substructure" as used herein in particular aspects refers to compounds having the following formulae:

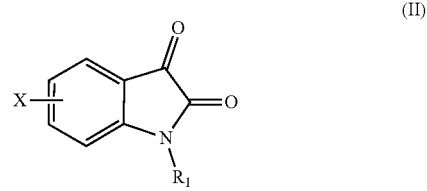

(II)

wherein $R_1$ is H or lower alkyl (e.g., C1-C4 alkyl) optionally substituted with —OH, for example, wherein X is H and wherein $R_1$ is H (isatin) or —$CH_3$ (N-methyl-isatin), or propyl (N-propyl-isatin), etc.; wherein X is independently H or halogen (e.g., I, Br, Cl, F); and salts, including pharmaceutically acceptable salts, thereof;

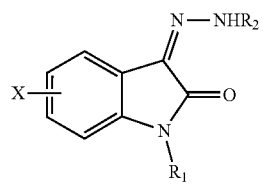

(III)

wherein $R_1$ is H or lower alkyl (e.g., C1-C4 alkyl) optionally substituted with —OH, for example, wherein X is H and wherein $R_1$ is H (indole, 2,3-dione, 3-hydrazone) etc.; wherein X is independently H or halogen (e.g., I, Br, Cl, F); wherein $R_2$ is independently H, lower alkyl (e.g., C1-C2 alkyl) optionally substituted with —OH, or aryl; and salts, including pharmaceutically acceptable salts, thereof, and

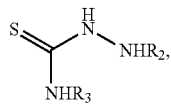
(IV)

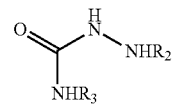
(V)

wherein $R_2$ and $R_3$ are independently H, lower alkyl (e.g., C1-C2 alkyl) optionally substituted with —OH, or aryl; and salts, including pharmaceutically acceptable salts, thereof; and combinations thereof.

In particular aspects, the following combinations of "methisazone functional group" or "methisazone functional substructure" are used:

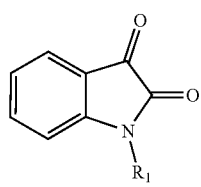
(VI)

plus

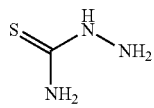

thiosemicarbazide wherein $R_1$ is H or lower alkyl (e.g., C1-C4 alkyl), for example, wherein $R_1$ is H (isatin) or —CH$_3$ (N-methyl-isatin), or propyl (N-propyl-isatin), etc., and salts, including pharmaceutically acceptable salts, thereof.

In particular aspects, the following combination of "methisazone functional groups" or "methisazone functional substructures" is used:

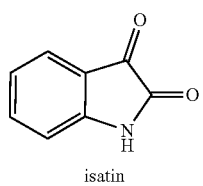

isatin plus

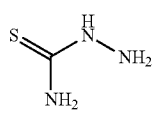

thiosemicarbazide

In the context of this disclosure "room temperature" refers to any temperature within a range of temperatures between about 16° C. (approximately 61° F.) and about 25° C. (approximately 77° F.). Commonly, room temperature is between about 20° C. and 22° C. (68° F.-72° F.). Generally, the term room temperature is used to indicate that no additional energy is expended cooling (e.g., refrigerating) or heating the sample or ambient temperature.

A "preservative" is an agent that is added to a composition to prevent decomposition due to chemical change or microbial action. In the context of vaccine production, a preservative is typically added to prevent microbial (e.g., bacterial and fungal) growth. The most common preservative used in vaccine production is thimerosal, a mercury containing organic compound. Thus, the term "preservative-free" indicates that no preservative is added to (or present in) the composition.

The term "purification" (e.g., with respect to a pathogen or a composition containing a pathogen) refers to the process of removing components from a composition, the presence of which is not desired. Purification is a relative term, and does not require that all traces of the undesirable component be removed from the composition. In the context of vaccine production, purification includes such processes as centrifugation, dialization, ion-exchange chromatography, and size-exclusion chromatography, affinity-purification, precipitation and other methods disclosed herein (e.g., lyophilization, etc). Such purification processes can be used to separate the inactiavated pathogen components from the reagents used to inactivate the respective pathogen as disclosed herein. For example hydrogen peroxide, metal reagents, "methisazone", "methisazone analogs" "methisazone functional groups" or "methisazone functional substructures" can be separated from the inactivated pathogen components to provide purified vaccine compositions. For example, residual methisazone, methisazone analogs, or chemicals representing methisazone functional groups or methisazone functional substructures may range from 0.0001 to 10 mM when used for vaccine antigen preparation. A range of standard purification techniques may be used to remove or separate these residual components from vaccine antigen prior to final formulation, including, but not limited to, affinity chromatography, ion-exchange chromatography, mixed-mode/multimodal chromatography, gel filtration/size-exclusion chromatography, desalting chromatography, tangential flow filtration/diafiltration, density-gradient centrifugation, centrifugal filtration, dialysis, vaccine antigen precipitation or vaccine antigen adsorption.

The adjective "pharmaceutically acceptable" indicates that the subject is physiologically acceptable for administration to a subject (e.g., a human or animal subject). Remington's Pharmaceutical Sciences, by E. W. Martin, Mack Publishing Co., Easton, PA, 15th Edition (1975), describes compositions and formulations (including diluents) suitable for pharmaceutical delivery of therapeutic and/or prophylactic compositions, including vaccines.

In general, the nature of the diluent will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In certain formulations (for example, solid compositions, such as powder, pill, tablet, or capsule forms), a liquid diluent is not employed. In such formulations, non-toxic solid carriers can be used, including for example, pharmaceutical grades of mannitol, lactose, starch or magnesium stearate.

The phrase "Good Manufacturing Practice" or "GMP" with respect to methods and procedures employed in vaccine production refer specifically to the set of methods, protocols and procedures established by the United States Food and Drug Administration (FDA). Similar recommendations and guidelines are promulgated by the World Health Organization. The abbreviation "cGMP" specifically designates those protocols and procedures that are currently approved by the FDA (e.g., under 21 Code of Federal Regulations, parts 210 and 211, available on the world wide web at fda.gov/cder/dmpq). With time cGMP compliant procedures may change. Any methods disclosed herein can be adapted in accordance with new cGMP requirements as mandated by the FDA.

Inactivation of Pathogens

To inactivate a pathogen using dual oxidizing agent(s), including those further comprising a methisazone reagent, the live pathogen is grown to a desired density (e.g., saturation density in culture), according to any procedures acceptable in the art for growing (e.g., culturing the specific organism). Typically, for cellular pathogens, it is desirable to culture the pathogen to stationary phase; as such organisms are generally more resistant to stresses in subsequent processing than those harvested at logarithmic phase. Growth in culture can be monitored using methods known in the art, such as measuring optical density of the culture using spectrophotometry. When the pathogen is a virus, growth can monitored by titering the virus using standard methods established for the selected virus. For example, methods for growing animal viruses can be found, for example, in DNA Viruses: A Practical Approach, Alan J. Cann (ed.) Oxford University Press, 2000; Robinson and Cranage (eds.) Vaccine Protocols (Methods in Molecular Medicine) Humana Press, 2003, and references cited therein. Methods for culturing pathogenic bacteria are also known in the art, and can be found in Molecular Cloning: A Laboratory Manual, 2nd ed., vol. 1-3, ed. Sambrook, et al., Cold Spring Harbor Laboratory Press, Cold Spring Harbor, N Y, 1989. Methods for culturing parasites, such as malaria, are also known in the art, e.g., Denise Doolan (ed.) Malaria Methods and Protocols (Methods in Molecular Medicine) Humana Press, 2002, and references cited therein.

Typically, the pathogenic organisms can have RNA or DNA genomes (e.g., viruses, bacteria, fungus, or parasites) and are purified from the medium in which they are grown or cultured, and in the case of pathogens that replicate inside a cell are purified from the other cellular components. For example, the relative concentration of non-pathogen components of a suspension including pathogens can be decreased by at least 50%, such as about 70%, or by as much as 80%, or even by 90%, 95% or more, relative to a crude preparation of pathogen. Intracellular pathogens, such as viruses, can be isolated or purified from the various components of the cells they infect by various methods known in the art.

For example, viruses for vaccine production are typically grown under controlled conditions in a certified cell line using biologically and chemically defined culture medium according to cGMP procedures. Cells are usually infected with virus at an appropriate multiplicity of infection (MOI), and the cells are maintained in culture under conditions and for a period of time sufficient to permit replication of the virus to high titer. The cells are then harvested by centrifugation (following release from the culture surface in the case of adherent cells), and resuspended in an appropriately buffered solution. To facilitate recovery, the buffered solution is typically hypotonic with respect to the cells, causing the cells to swell. Optionally, the cell suspension is agitated periodically to ensure a more uniform exposure of the cells to the hypotonic solution. The cells are then lysed, for example, by homogenization, to release the virus. The lysate is centrifuged to remove large particulate matter, such as cell nuclei, and the supernatant is filtered to remove additional cellular debris. The virus can then be further purified by layering the filtered supernatant onto a suitable separation medium, such as a sucrose density gradient. Optionally, the nuclear pellet can be further processed to increase viral yield. The nuclear pellet is resuspended again in hypotonic buffer and homogenized. The nuclear lysate is centrifuged and the resulting supernatant is filtered prior to layering onto separation medium. Optionally, the two viral suspensions are combined to achieve an approximately equal volume separation gradient. The separation medium/virus suspension is then processed by ultracentrifugation (e.g., at 55,000×g for 1-1.5 hours at 4° C. Virus is collected into a pellet by this process whereas membranous cellular debris remains at the interface. The supernatant is removed (typically by aspiration) and the pellet is resuspended in buffer. The purified virus can then be evaluated for recovery and viability (for example by determining protein concentration and by plaque assays, respectively). If desired the recovered virus can be frozen and stored until use.

Similar procedures are known in the art for purifying non-viral pathogens, such as intracellular parasites (for example, protozoan parasites, including *Plasmodium falciparum* and other *Plasmodium* species, *Leishmania* (sp.), *Cryptosporidium parvum, Entamoeba histolytica*, and *Giardia lamblia*, as well as *Toxoplasma, Eimeria, Theileria*, and *Babesia* species).

Reconstitution and Administration

Immunogenic compositions, such as vaccines, that are produced as powders (e.g., lyophilized powders) are typically mixed with a liquid for administration. This process is known as "reconstitution," and the liquid used is commonly referred to as a "diluent." For purposes of administration, especially to human subjects, it is important that the diluent be a pharmaceutically acceptable formulation. Reconstitution of the lyophilized composition is typically carried out using a sterile syringe and needle for each vial of diluent. The correct diluent for each type and batch is used to ensure adequate potency, safety and sterility of the resulting mixture. Diluents are specifically designed to optimize delivery and efficacy of the selected composition. Common diluents include such additives as: stabilizers to improve heat stability of the vaccine; agents, such as surfactants, to assist in dissolving the powder into a liquid; and buffers to ensure the correct acidic balance of the reconstituted composition. Optionally, the diluent can contain a preservative (e.g., a bactericide and/or a fungicide) to maintain sterility after reconstitution. Preservatives are typically required (e.g., by the FDA) when the composition is reconstituted in a multidose formulation.

Administration of Immunogenic Compositions Such as Vaccines (Therapeutic Methods)

The immunogenic compositions (such as vaccine or other medicaments) disclosed herein can be administered to a subject to elicit an immune response against a pathogen. Most commonly, the compositions are administered to elicit a prophylactic immune response against a pathogenic organism to which the subject has not yet been exposed. For example, vaccine compositions including dual oxidation-inactivated pathogens can be administered as part of a localized or wide-spread vaccination effort. An immune response elicited by administration of such vaccine compositions typically includes a neutralizing antibody response, and can in addition include a T cell response, e.g., a cytotoxic T cell response that targets cellular pathogens. Accordingly, methods for making a medicament or pharmaceutical composition containing dual oxidation-inactivated pathogens are included herein. The pharmaceutical compositions (medicaments) include at least one pathogen inactivated by contact with a solution containing the dual oxidizing agent(s), or by contact with the dual oxidizing agents further comprising a methisazone reagent, in a pharmaceutically acceptable carrier or excipient.

In some cases, the immunogenic composition can include a combination of pathogens, such as a combination of viruses (for example mumps virus, measles virus, rubella virus), or a combination of bacteria (for example, *Campylobacter* species (spp.), *Corynebacterium diptheriae*, *Bordatella pertussis*, and *Clostridium tetani*), or a combination of pathogens selected from different classes of organisms, e.g., one or more viruses and one or more bacteria, one or more bacteria and one or more parasites, and the like.

The quantity of pathogen included in the composition is sufficient to elicit an immune response when administered to a subject. For example, when administered to a subject in one or more doses, a vaccine composition containing an inactivated pathogen favorably elicits a protective immune response against the pathogen. A dose of the vaccine composition can include at least about 0.1% wt/wt inactivated pathogen to about 99% wt/wt inactivated pathogen, with the balance of the vaccine composition is made up of pharmaceutically acceptable constituents, such as a pharmaceutically acceptable carrier and/or pharmaceutically acceptable diluent. Guidelines regarding vaccine formulation can be found, e.g., in U.S. Pat. Nos. 6,890,542, and 6,651,655. In one specific, non-limiting example the vaccine composition (medicament) includes at least about 1%, such as about 5%, about 10%, about 20%, about 30%, or about 50% wt/wt inactivated pathogen. As will be apparent to one of ordinary skill in the art, the quantity of pathogen present in the vaccine formulation depends on whether the composition is a liquid or a solid. The amount of inactivated pathogen in a solid composition can exceed that tolerable in a liquid composition. The amount of inactivated pathogen can alternatively be calculated with respect to the comparable amount of a live or inactivated pathogen required to give an immune response. For example, a dosage equivalent in viral particles to from about $10^6$ to about $10^{12}$ plaque forming units (PFU) of live or attenuated virus can be included in a dose of the vaccine composition. Similarly, a vaccine composition can include a quantity of inactivated pathogen (e.g., with RNA or DNA genome), such as virus, bacteria, fungus or parasite equivalent to between about $10^3$ to about $10^{10}$ live organisms. Alternatively, the dosage can be provided in terms of protein content or concentration. For example, a dose can include from approximately 0.1 μg, such as at least about 0.5 μg protein. For example, a dose can include about 1 μg of an isolated or purified virus or other pathogen up to about 100 μg, or more of a selected pathogen. Although the equivalent doses in infectious units (e.g., PFU) can vary from pathogen to pathogen, the appropriate protein dose can be extrapolated (for example, from PFU) or determined empirically. For example, in a typical preparation, 1 μg of purified vaccinia virus is equivalent to approximately $2 \times 10^6$ PFU. Similar conversions can be determined for any pathogen of interest.

Typically, preparation of a vaccine composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for appropriate processing and presentation of the vaccine antigen by antigen presenting cells. Such components can be supplied in lyophilized form, or can be included in a diluent used for reconstitution of a lyophilized form into a liquid form suitable for administration. Alternatively, where the inactivated pathogen is prepared for administration in a solid state (e.g., as a powder or pellet), a suitable solid carrier is included in the formulation.

Aqueous compositions typically include an effective amount of the inactivated pathogen dispersed (for example, dissolved or suspended) in a pharmaceutically acceptable diluent or aqueous medium. The phrase "pharmaceutically acceptable" refers to molecular entities and compositions that do not produce an adverse, allergic or other undesirable reaction when administered to a human or animal subject. As used herein, "pharmaceutically acceptable carrier" includes any and all solvents, dispersion media, coatings, isotonic and absorption delaying agents and the like. Optionally, a pharmaceutically acceptable carrier or diluent can include an antibacterial, antifungal or other preservative. The use of such media and agents for pharmaceutically active substances is well known in the art. Except insofar as any conventional media or agent is incompatible with production of an immune response by an inactivated pathogen, its use in the immunogenic compositions is contemplated. Supplementary active ingredients also can be incorporated into the compositions. For example, certain pharmaceutical compositions can include the inactivated pathogen in an aqueous diluent, mixed with a suitable surfactant, such as hydroxypropylcellulose. Dispersions also can be prepared in glycerol, liquid polyethylene glycols, and mixtures thereof and in oils. In some cases (for example, when liquid formulations are deemed desirable, or when the lyophilized vaccine composition is reconstituted for multiple doses in a single receptacle), these preparations contain a preservative to prevent the growth of microorganisms.

Pharmaceutically acceptable carriers, excipients and diluents are known to those of ordinary skill in the described, e.g., in Remington's Pharmaceutical Sciences, by E. W. Martin, Mack Publishing Co., Easton, PA, 15th Edition (1975), describes compositions and formulations suitable for pharmaceutical delivery of inactivated pathogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

For example, the pharmaceutical compositions (medicaments) can include one or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770. A stabilizing detergent is any detergent that allows the components of the emulsion to remain as a stable emulsion. Such detergents include polysorbate, 80 (TWEEN80) (Sorbitan-mono-9-octadecenoate-poly(oxy-1,2-ethanediyl; manufactured by ICI Americas, Wilmington, DE), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by, e.g., Schmolka, J. Am. Oil. Chem. Soc. 54:110, 1977, and Hunter et al., J. Immunol 129:1244, 1981, and such agents as PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167, 1984. The agent can be provided in an effective amount, for example between 0.5 and 10%, or in an amount between 1.25 and 5%.

The oil included in the composition is chosen to promote the retention of the pathogen in oil-in-water emulsion, and preferably has a melting temperature of less than 65° C., such that emulsion is formed either at room temperature, or once the temperature of the emulsion is adjusted to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects are evident upon use of the oil.

Optionally, the pharmaceutical compositions or medicaments can include a suitable adjuvant to increase the immune response against the pathogen. As used herein, an "adjuvant" is any potentiator or enhancer of an immune response. The term "suitable" is meant to include any substance which can be used in combination with the selected pathogen to augment the immune response, without producing adverse reactions in the vaccinated subject. Effective amounts of a specific adjuvant may be readily determined so as to optimize the potentiation effect of the adjuvant on the immune response of a vaccinated subject. For example, suitable adjuvants in the context of vaccine formulations include 03%-5% (e.g., 2%) aluminum hydroxide (or aluminum phosphate) and MF-59 oil emulsion (0.5% polysorbate 80 and 0.5% sorbitan trioleate. Squalene (5.0%) aqueous emulsion) is another adjuvant which has been favorably utilized in the context of vaccines. For example, the adjuvant can be a mixture of stabilizing detergents, micelle-forming agent, and oil available under the name Provax® (DEC Pharmaceuticals, San Diego, CA). An adjuvant can also be an immunostimulatory nucleic acid, such as a nucleic acid including a CpG motif. Other adjuvants include mineral, vegetable or fish oil with water emulsions, incomplete Freund's adjuvant, *E. coli* J5, dextran sulfate, iron sulfate, iron oxide, sodium alginate, Bacto-Adjuvant, certain synthetic polymers such as Carbopol (BF Goodrich Company, Cleveland, Ohio), poly-amino acids and co-polymers of amino acids, saponin, carrageenan, REGRESSIN (Vetrepharm, Athens, Ga.), AVRIDINE (N, N-dioctadecyl-N', N'-bis(2-hydroxyethyl)-propanediamine), long chain polydispersed.beta. (1,4) linked mannan polymers interspersed with O-acetylated groups (e.g. ACEMANNAN), deproteinized highly purified cell wall extracts derived from non-pathogenic strain of *Mycobacterium* species (e.g., EQUIMUNE, Vetrepharm Research Inc., Athens Ga.), Mannite monooleate, paraffin oil and muramyl dipeptide. A suitable adjuvant can be selected by one of ordinary skill in the art.

The pharmaceutical compositions (medicaments) can be prepared for use in therapeutic or prophylactic regimens (e.g., vaccines) and administered to human or non-human subjects to elicit an immune response against one or more pathogens. For example, the compositions described herein can be administered to a human (or non-human) subject to elicit a protective immune response against one or more pathogens. To elicit an immune response, a therapeutically effective (e.g., immunologically effective) amount of the inactivated pathogen is administered to a subject, such as a human (or non-human) subject.

A "therapeutically effective amount" is a quantity of a composition used to achieve a desired effect in a subject being treated. For instance, this can be the amount necessary to stimulate an immune response, to prevent infection, to reduce symptoms, or inhibit transmission of a pathogen. When administered to a subject, a dosage will generally be used that will achieve target tissue concentrations (for example, in antigen presenting cells) that is empirically determined to achieve an in vitro effect. Such dosages can be determined without undue experimentation by those of ordinary skill in the art.

An immunogenic composition, such as a vaccine composition containing an inactivated pathogen, can be administered by any means known to one of skill in the art, such as by intramuscular, subcutaneous, or intravenous injection, but even oral, nasal, and transdermal mutes are contemplated. In one embodiment, administration is by subcutaneous or intramuscular injection. To extend the time during which the inactivated pathogen is available to stimulate a response, the peptide can be provided as an oily injection, as a particulate system, or as an implant. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release.

As an alternative to liquid formulations, the composition can be administered in solid form, e.g., as a powder, pellet or tablet. For example, the vaccine composition can be administered as a powder using a transdermal needleless injection device, such as the helium-powered POWDERJECT® injection device. This apparatus uses pressurized helium gas to propel a powder formulation of a vaccine composition, e.g., containing an inactivated pathogen, at high speed so that the vaccine particles perforated the stratum corneum and land in the epidermis.

Polymers can be also used for controlled release. Various degradable and nondegradable polymeric matrices for use in controlled drug delivery are known in the art (Langer, Accounts Chem. Res. 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425, 1992; and Pec, J. Parent. Sci. Tech. 44(2):58, 1990). Alternatively, hydroxyapatite has been used as a microcarrier for controlled release of proteins (Ijntema, et al., Int. J. Pharm. 112:215, 1994). In yet another aspect, liposomes are used for controlled release as well as drug targeting of the lipid-capsulated drug (Betageri, et al., Liposome Drug Delivery Systems, Technomic Publishing Co., Inc., Lancaster, P A, 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In specific, non-limiting examples, the inactivated pathogen (e.g., a parasite, such as a protozoan parasite, or a bacterial pathogen) is administered to elicit a cellular immune response (e.g., a cytotoxic T lymphocyte (CTL) response). A number of means for inducing cellular responses, both in vitro and in vivo, are known. Lipids have been identified as agents capable of assisting in priming CTL responses in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide or protein. The lipidated peptide can then be injected directly in a micellar form, incorporated in a liposome, or emulsified in an adjuvant. As another example, *E coli* lipoproteins, such as tripalmitoyl-S-glycerylcysteinlyseryl-serine can be used to prime tumor specific CTL when covalently attached to an appropriate peptide (see, Deres et al., Nature 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

Dosages of inactivated pathogen are administered that are sufficient to elicit an immune response, e.g., a protective immune response, in a subject. With respect to viral pathogens, the dosage is typically calculated based on the amount of biological matter equivalent to a specified titer of infectious (e.g., virulent or attenuated) virus. For example, a dose equivalent to about $10^6$, or about $10^7$, or about $10^8$, or about $10^9$, or about $10^{10}$, or about $10^{11}$ or about $10^{12}$, or even more live virus per dose can be administered to elicit an immune response in a subject. In some cases, the dose includes an amount in excess of the amount of a live virus utilized to elicit an immune response, because the inactivated vaccine is incapable of increasing in number after administration into the subject. When calculating the amount of a cellular pathogen, e.g., a bacteria, a fungus or a parasite, the amount can be calculated by comparison to a dose of live bacteria, e.g., from about $10^3$ cells or organisms to about $10^{10}$ live organisms, depending on the formulation. For example, the dose can include at least about 100 nanograms (or 200 nanograms, or 500 nanograms, or 1 microgram) of protein antigen per dose to about 25 mg (e.g., about 10 mg, or about 15 mg, or about 20 mg), or even more of an inactivated pathogen. Typically the vaccine composition includes additional pharmaceutically acceptable constituents or components. Accordingly, the vaccine composition can include at least about 0.1% wt/wt inactivated pathogen to about 99% wt/wt inactivated pathogen, with the balance of the vaccine composition is made up of pharmaceutically acceptable constituents, such as a one or more pharmaceutically acceptable carrier, pharmaceutically acceptable stabilizer and/or pharmaceutically acceptable diluent. Guidelines regarding vaccine formulation can be found, e.g., in U.S. Pat. Nos. 6,890,542, and 6,651,655. Doses can be calculated based on protein concentration (or infectious units, such as PRJ, of infectious unit equivalents). The optimal dosage can be determined empirically, for example, in preclinical studies in mice and non-human primates, followed by testing in humans in a Phase I clinical trial. Actual methods for preparing administrable compositions will be known or apparent to those skilled in the art and are described in more detail in such publications as Remington's Pharmaceutical Sciences, 19th Ed., Mack Publishing Company, Easton, Pennsylvania, 1995.

Typically, but not always, the vaccine compositions are administered prior to exposure of a subject to a pathogen, e.g., as a vaccine. Vaccine compositions can be prepared by inactivating a wide range of pathogens using dual oxidizing conditions, or using dual oxidizing conditions further comprising a methisazone reagent(s), according to the methods described herein. For example, vaccine compositions can be prepared by inactivating a pathogenic virus with a solution containing dual oxidizing reagent(s), or with a solution containing dual oxidizing reagent(s) further comprising a methisazone reagent(s). Non-limiting examples of viruses that can be inactivated by the dual oxidation methods for vaccine production are disclosed herein.

Bacterial pathogens can also be inactivated using dual oxidizing reagent(s), or using dual oxidizing conditions further comprising a methisazone reagent(s), for use in vaccine compositions. Non-limiting examples of bacteria that can be inactivated by the dual oxidation methods for vaccine production are disclosed herein.

Vaccine compositions can also be produced from fungal pathogens inactivated using dual oxidizing reagent(s), or using dual oxidizing conditions further comprising a methisazone reagent(s). Non-limiting examples of fungal pathogens that can be inactivated by the dual oxidation methods for vaccine production are disclosed herein.

Vaccine compositions can also be produced from parasitic pathogens inactivated using dual oxidizing reagent(s), or using dual oxidizing conditions further comprising a methisazone reagent(s). Non-limiting examples of parasitic pathogens that can be inactivated by the dual oxidation methods for vaccine production are disclosed herein.

It will be apparent that the precise details of the methods or compositions described can be varied or modified without departing from the spirit of the described invention. The following examples are provided to illustrate certain particular features and/or embodiments. These examples should not be construed to limit the invention to the particular features or embodiments described. Each of the references cited below is incorporated by reference for all purposes.

Example 1

(Standard $H_2O_2$-Based Inactivation was Shown to Inactivate CHIKV, but Also Damaged CHIKV-Specific Neutralizing Epitopes and Failed to Induce Neutralizing Responses In Vivo Following Vaccination)

FIG. 2 shows that standard $H_2O_2$-based inactivation disrupts CHIKV-specific neutralizing epitopes and fails to induce neutralizing responses in vivo following vaccination.

In FIG. 2A, Chikungunya virus (CHIKV) samples received no treatment (Live CHIKV) or were treated with a standard concentration of $H_2O_2$ (3% $H_2O_2$ CHIKV) for 7 hours at room temperature. Following treatment, antigen was tested with a CHIKV-specific sandwich ELISA comprised of two neutralizing monoclonal antibodies specific for the E1 and E2 structural proteins. ELISA values are expressed as a percentage of live virus controls.

In FIG. 2B, $H_2O_2$-treated CHIKV (3% $H_2O_2$ CHIKV) was tested and found negative for residual live virus, formulated with 0.1% alum, and used to immunize adult BALB/c mice (n=8) on days 0 and 28. Control mice (Mock, n=3) were immunized on the same schedule with alum in diluent. Two weeks following the final immunization peripheral blood was collected, processed for serum and pooled for each group. Pooled serum was tested using a standard CHIKV 50% plaque reduction neutralization assay ($PRNT_{50}$). Samples from the 3% $H_2O_2$-CHIKV and mock vaccinated groups were seronegative, with a $PRNT_{50}$ titer of less than 10, as indicated by the dashed line. For comparison, a group of C57BL/6 mice (n=5) immunized with live CHIKV by the intradermal footpad route (1,000 PFU of CHIKV-SL15649) are shown (left-most bar graph of FIG. 2B), with neutralizing titers tested 36 days following infection. The limit of detection (LOD) is indicated by the dashed line.

Example 2

(Dual Oxidation-Based Microbial Inactivation was Found by Applicants to have a Fundamentally Different Mechanism Compared with Simple Oxidation with $H_2O_2$ Alone, Thereby Discouraging the Potential Use of Dual Oxidation-Based Microbial Inactivation for the Development of Advanced Efficacious Vaccine Antigens)

While Fenton-type reactions have only been used for killing pathogens, and have not been used or suggested for using in the development of vaccines, such reactions were nonetheless tested for the potential to inactivate microbial pathogens for purpose of vaccine production. The initial inactivation data was surprising and unexpected, because in contrast to $H_2O_2$, it was found that the total protein concentration of the solution during the inactivation procedure impacts $H_2O_2/CuCl_2$ dual-oxidation inactivation kinetics. This $H_2O_2/CuCl_2$ system result was unexpected because protein concentration had been previously shown to have no impact on viral inactivation using Applicants' standard $H_2O_2$ approach. However, as shown in FIGS. 1A and 1B for DENV2, protein concentration had a substantial impact in viral inactivation kinetics, with higher protein levels leading to slower inactivation of the virus.

Specifically, FIGS. 1A and 1B show that the kinetics of virus inactivation using the $H_2O_2/CuCl_2$ dual oxidation system is protein concentration-dependent, whereas standard $H_2O_2$-based virus inactivation is protein concentration-independent. In FIG. 1A, purified DENV2 was treated with either 3% $H_2O_2$, or in FIG. 1B with 0.01% $H_2O_2$ and 1 µM $CuCl_2$ at room temperature, with increasing concentrations of total viral protein as indicated. Samples were removed at pre-specified time points and assessed for viral titers using a standard plaque forming unit (PFU) assay. The limit of detection (LOD) is indicated by the dashed line.

The dependence on total protein concentration of the solution during the dual inactivation procedure was unexpected, indicating that a fundamentally different mechanism was involved compared to $H_2O_2$ alone, and thus the efficacy/use of a dual oxidation-based inactivation procedure for effective vaccine production was questionable and unpredictable in view of Applicants' prior simple oxidation based methods (e.g., with $H_2O_2$ alone) (e.g., U.S. Pat. Nos. 8,124, 397 and 8,716,000).

Example 3

(A Dual Oxidizing Fenton-Type Oxidation System was Used to Provide Efficient Inactivation while Improving the Maintenance of CHIKV-Specific Neutralizing Epitopes)

Figure 3C:
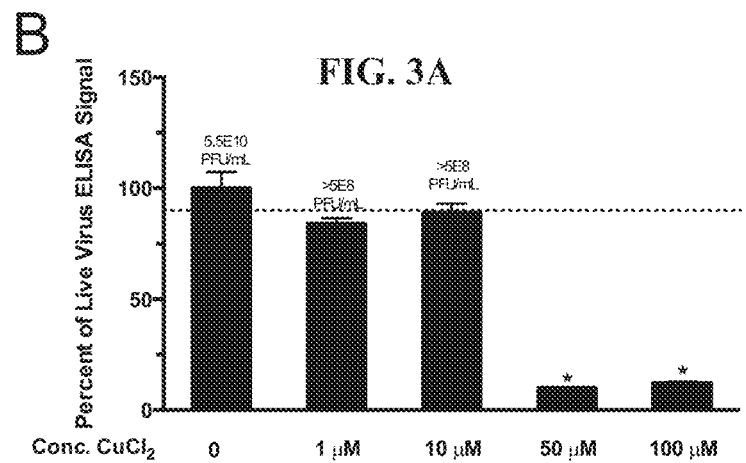
Figure 3C:
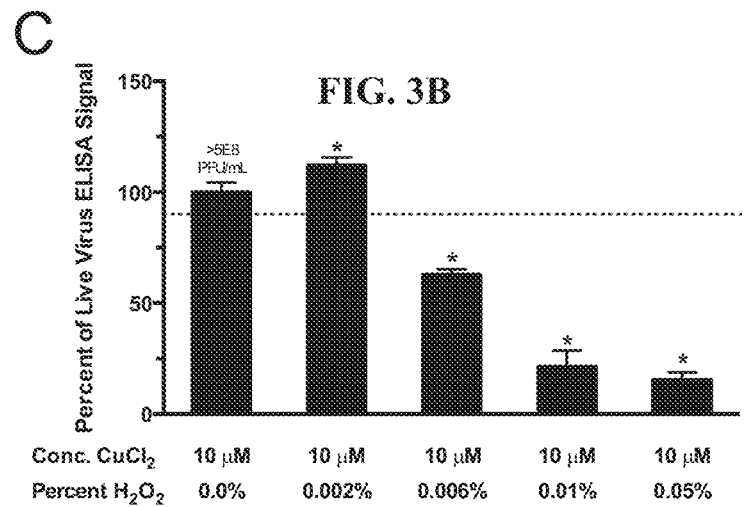

FIG. 3 shows that the use of a dual oxidizing Fenton-type oxidation system provides efficient inactivation while improving the maintenance of CHIKV-specific neutralizing epitopes.

In FIG. 3A, purified CHIKV was treated with increasing concentrations of $H_2O_2$ alone.

In FIG. 3B, purified CHIKV was treated with $CuCl_2$ alone.

In FIG. 3C, purified CHIKV was treated with $CuCl_2$ (10 µM) with increasing concentrations of $H_2O_2$ to achieve a dual oxidizing Fenton-type system. Antigen treatments were allowed to proceed for 20 hours at room temperature.

Following treatments, antigen was tested with a CHIKV-specific sandwich ELISA comprised of two neutralizing monoclonal antibodies specific for the E1 and E2 structural proteins. ELISA values are expressed as a percentage of live virus controls. Following treatment, material was also tested for live virus using a standard plaque forming unit (PFU) assay. Resulting virus titers (PFU/mL) are indicated for each condition. Increasing concentrations of either decontamination reagent (FIGS. 3A and 3B) led to enhanced inactivation, but at the expense of significantly decreased antigenicity. Surprisingly, by contrast, using the combined $H_2O_2/CuCl_2$ system, an optimal inactivation condition was identified that fully maintained antigenicity while leading to complete viral inactivation (FIG. 3C). Successful conditions that demonstrated no detectable live virus (<50 PFU/mL) are indicated by an asterisk. Note that only the optimal conditions of 10 µM $CuCl_2$ and 0.002% $H_2O_2$ achieved ≥90% retained antigenicity (indicated by the dashed line) while also demonstrating no detectable live virus.

Example 4

($CuCl_2/H_2O_2$-CHIKV Vaccination Induced Rapid Neutralizing Antibody Responses, and Protected Against (HIKV-Associated Pathology)

Figure 4:
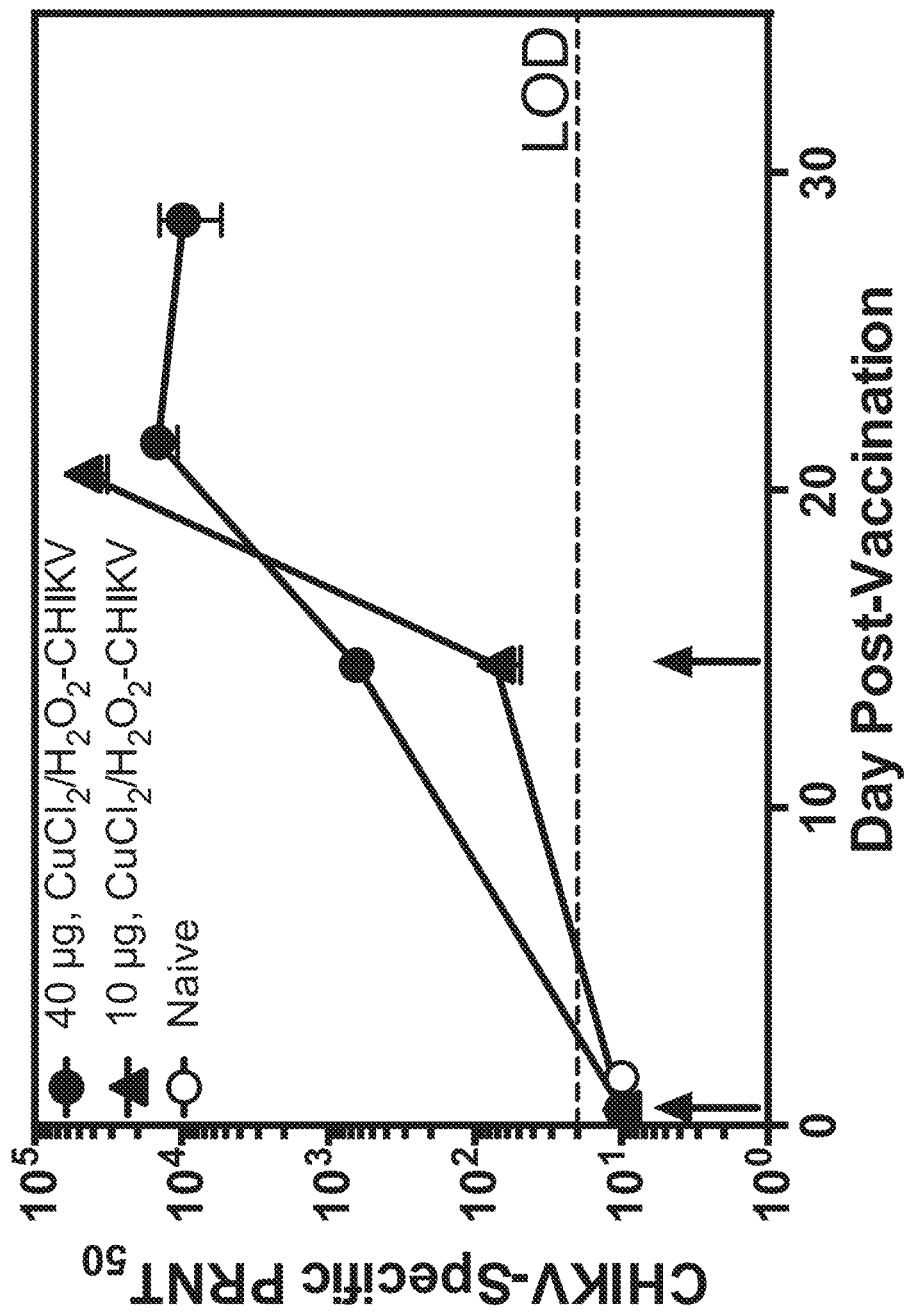
FIG. 4 shows, according to particular aspects, that $CuCl_2$/$H_2O_2$-CHIKV vaccination induces rapid neutralizing antibody responses.

To assess the immunogenicity of the $H_2O_2/CuCl_2$-treated CHIKV candidate, vaccine antigen was formulated with alum adjuvant and used to immunize mice at several dose levels (10 or 40 µg per animal). As shown in FIG. 4, vaccination generated rapid and robust neutralizing antibody titers, in stark contrast to the conventional $H_2O_2$ approach (FIG. 2). As a final test of vaccine efficacy, immunized mice were challenged with wild-type CHIKV, and demonstrated full protection against arthritic disease (FIG. 5).

FIG. 4 shows that $CuCl_2/H_2O_2$-CHIKV vaccination induced rapid neutralizing antibody responses. Specifically, an optimized $CuCl_2/H_2O_2$-CHIKV vaccine was formulated with 0.1% alum at a 10 µg or 40 µg dose with a primary dose given at day 0 and a booster dose at day 14 (shown by arrows). Serum samples were collected at the indicated time points and assayed for CHIKV-specific neutralizing activity using a standard plaque reduction neutralization titer assay ($PRNT_{50}$). Neutralizing titers for the 10 µg group end on day 20 post-primary vaccination because this is the last time point before the animals were challenged with CHIKV on day 21. Group averages (+SEM) are shown for each time point. The limit of detection (LOD) for this study is indicated by the dashed line. Naive, unvaccinated controls were also tested and found to be below the LOD.

Figures 5A, 5B:
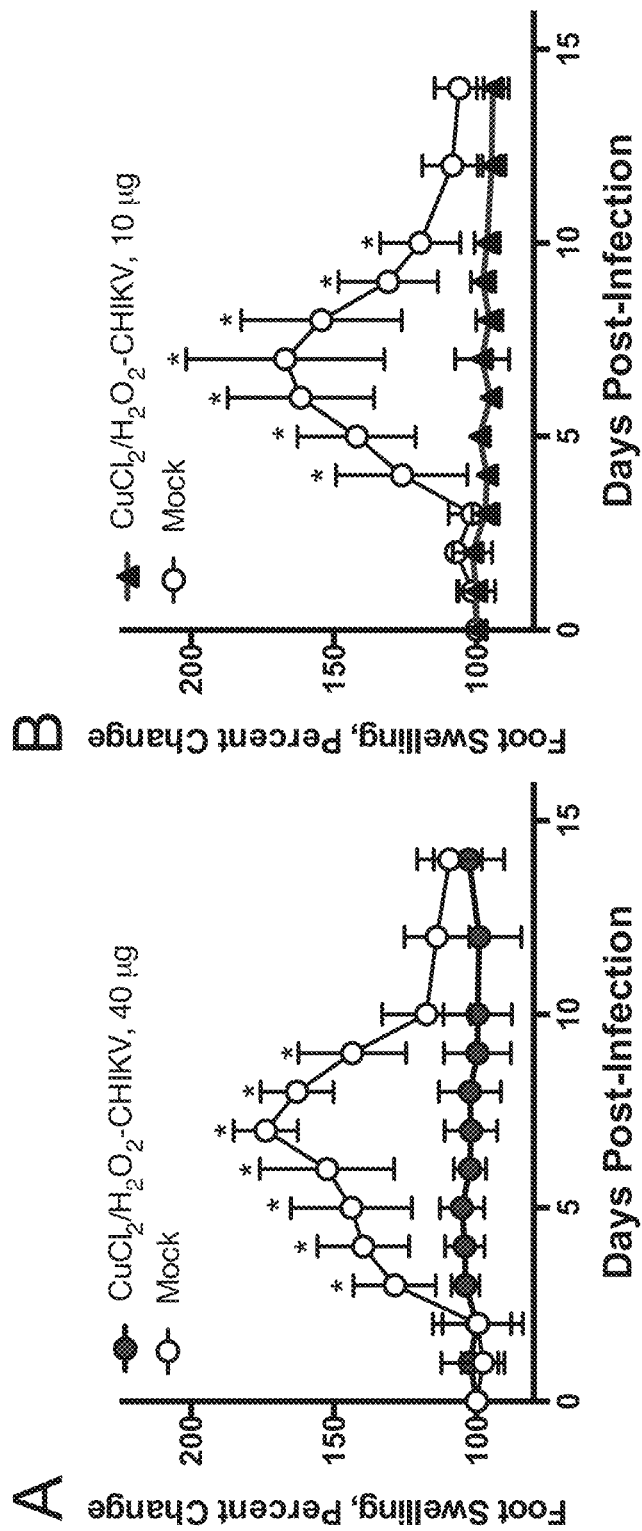
FIGS. 5A and 5B show, according to particular aspects, that $CuCl_2$/$H_2O_2$-CHIKV vaccination protects against CHIKV-associated pathology.

FIGS. 5A and 5B show that CuCl$_2$/H$_2$O$_2$-CHIKV vaccination induced rapid neutralizing antibody responses, and protected against CHIKV-associated pathology. Specifically, the CuCl$_2$/H$_2$O$_2$-CHIKV vaccine was formulated with alum at a 10 μg or 40 μg dose with a primary immunization given at day 0 and a booster dose administered at day 14 in adult C57BL/6 mice (n=5 per group) or mock vaccinated controls (alum only). Mice were challenged in the right footpad with 1,000 PFU of CHIKV-SL15649, a virulent strain of CHIKV, at either 32 days (40 μg group) or 21 days (10 μg group) after primary vaccination. CHIKV-associated foot swelling was measured with calipers for 14 days in mice vaccinated with (FIG. 5A) a 40 μg dose or (FIG. 5B) a 10 μg dose. Significant differences are indicated by asterisks (Student's t-test, P<0.05).

CuCl$_2$/H$_2$O$_2$-CHIKV vaccination generated rapid and robust neutralizing antibody titers (FIG. 4), and demonstrated full protection against arthritic disease (FIG. 5).

Example 5

(H$_2$O$_2$/CuCl$_2$-Based Oxidation was Used to Develop an Effective Inactivated YFV Vaccine)

Based on the encouraging results demonstrated with CHIKV, a model *alphavirus*, the utility of the system for flaviviruses such as YFV was explored. Preliminary analysis suggested that a concentration of 0.002% H$_2$O$_2$ and 1 μM CuCl$_2$ represented a functional balance between antigenicity and rapid virus inactivation (FIG. 6A).

Using a further optimized condition of 0.010% H$_2$O$_2$ and 1 μM CuCl$_2$ (to ensure full inactivation) vaccine material was produced for YFV and used to immunize adult BALB/c mice. Following vaccination, all animals demonstrated measurable neutralizing titers with an average neutralizing titer of 240, compared to a neutralizing titer of less than 40 for animals immunized with YFV vaccine prepared using H$_2$O$_2$ alone (FIG. 6B). These differences in immunogenicity after vaccination could be anticipated based on the severe damage to neutralizing epitopes (i.e., antigenicity) observed when YFV was treated with 3% H$_2$O$_2$ for 20 hours.

FIGS. 6A and 6B show that H$_2$O$_2$/CuCl$_2$-based oxidation was successfully used in the development of an inactivated YFV vaccine, and demonstrating enhanced retention of antibody binding to neutralizing epitopes (antigenicity) and improved immunogenicity after vaccination.

Specifically, as shown in FIG. 6A, purified YFV was treated with the indicated conditions for 20 hours at room temperature. Following treatment, antigen was tested using a YFV-specific sandwich ELISA comprised of a neutralizing monoclonal antibody specific for the envelope structural protein. ELISA values are expressed as a percentage of the live virus control. Following treatment, material was also tested for live YFV using a standard plaque forming unit (PFU) assay. Resulting virus titers (PFU/mL) are indicated for each condition. Successful conditions that demonstrated no detectable live virus are indicated by an asterisk.

Specifically, as shown in FIG. 6B, immunization of mice with the standard H$_2$O$_2$-based inactivated YFV (3% H$_2$O$_2$ for 7 hours) was compared to an optimized H$_2$O$_2$/CuCl$_2$ condition (0.01% H$_2$O$_2$, 1 uM CuCl$_2$, 20 hours at room temperature). Following inactivation, vaccine preparations were tested and found negative for live virus. Each vaccine was formulated with alum at a 5 μg (3% H$_2$O$_2$) or 10 μg (0.01% H$_2$O$_2$, 1 μM CuCl$_2$) dose with a primary immunization given at day 0 and booster doses administered at days 14 and 25 in adult BALB/c mice (n=5 per group). Animals were tested for neutralizing antibody titers on day 42. The limit of detection (LOD) is indicated by the dashed line.

H$_2$O$_2$/CuCl$_2$-based oxidation, therefore, was successfully used in the development of an inactivated YFV vaccine, and demonstrating enhanced retention of antibody binding to neutralizing epitopes (antigenicity) and improved immunogenicity after vaccination.

Example 6

(H$_2$O$_2$/CuCl$_2$-Based Oxidation was Successfully Used in the Development of an Inactivated DENV Vaccine)

Based on the encouraging results demonstrated with YFV, another model *flavivirus*, dengue 3 (DENV3) was tested in the H$_2$O$_2$/CuCl$_2$ system.

As with YFV, initial tests indicated that a concentration of 0.002% H$_2$O$_2$ and 1 μM CuCl$_2$ represented an optimal approach for maintaining high antigenicity while also providing complete virus inactivation (FIG. 7).

Specifically, FIG. 7 shows that use of a dual oxidizing Fenton-type oxidation system demonstrated enhanced inactivation while maintaining dengue virus 3-specific neutralizing epitopes. Purified dengue virus 3 (DENV3) was treated with the indicated conditions for 20 hours at room temperature. Following treatment, antigen was tested with a DENV-specific sandwich ELISA comprised of two neutralizing monoclonal antibodies specific for the envelope structural protein. ELISA values are expressed as a percentage of the live virus control. Following treatment, material was also tested for live DENV3 using a standard plaque forming unit (PFU) assay. Resulting virus titers (PFU/mL) are indicated for each condition. Successful conditions that demonstrated no detectable live virus (<50 PFU/mL) are indicated by an asterisk. Note that only the optimal conditions of 1 μM CuCl$_2$ and 0.002% H$_2$O$_2$ retained high antigenicity while also demonstrating no detectable live virus Using these preliminary H$_2$O$_2$/CuCl$_2$ inactivation conditions, vaccine lots of each DENV serotype were produced, formulated into a tetravalent dengue vaccine adjuvanted with 0.10% aluminum hydroxide, and used to immunize adult rhesus macaques. Following a single booster immunization, all monkeys seroconverted (NT$_{50}$≥10), with the H$_2$O$_2$/CuCl$_2$ inactivation approach demonstrating an improvement in neutralizing antibody responses for 3 out of 4 dengue virus serotypes and an average 8-fold increase in geometric mean titers when compared to inactivation with H$_2$O$_2$ alone (FIG. 8).

Specifically, FIG. 8 shows that The H$_2$O$_2$/CuCl$_2$ dual-oxidation system enhanced in vivo immunogenicity to a tetravalent DENV vaccine in rhesus macaques. Purified DENV was treated with either 3% H$_2$O$_2$ (7 hours, room temperature) or H$_2$O$_2$/CuCl$_2$ (0.002% H$_2$O$_2$ and 1 μM CuCl$_2$ for 20 hours, room temperature). Full inactivation was confirmed through standard plaque assay and co-culture. Vaccine antigens were blended at equal concentrations (1 μg per serotype for 3% H$_2$O$_2$, or 2 μg per serotype for H$_2$O$_2$/CuCl$_2$) and formulated with 0.1% alum. Adult rhesus macaques (n=4 per group) were immunized intramuscularly at day 0 and day 28, with neutralization titers (NT$_{50}$) measured at 1-month following booster immunization. The limit of detection (LOD) is indicated by the dashed line.

There was a small difference in antigen dose (1 μg/serotype vs. 2 μg/serotype) in these studies and so the experiment was repeated in mice that were vaccinated with the same dose of tetravalent dengue vaccine antigen (FIG. 9).

Specifically, FIG. 9 shows that The H$_2$O$_2$/CuCl$_2$ dual-oxidation system enhances in vivo immunogenicity to a tetravalent DENV vaccine in mice. Purified DENV was treated with either 3% $H_2O_2$ (7 hours, room temperature) or $H_2O_2/CuCl_2$ (0.002% $H_2O_2$ and 1 µM $CuCl_2$ for 20 hours, room temperature). Full inactivation was confirmed through standard plaque assay and co-culture. Vaccine antigens were blended at equal concentrations (2 µg per serotype) and formulated with 0.1% alum. Adult BALB/c mice (n=4-5 per group) were immunized subcutaneously at days 0, 14 and day 28, with neutralization titers ($NT_{50}$) measured at two-weeks following the final immunization. The limit of detection (LOD) is indicated by the dashed line.

In these experiments, the dual oxidation approach of $H_2O_2/CuCl_2$ inactivation was more immunogenic than 3% $H_2O_2$ for all 4 dengue virus serotypes and resulted in an 8-fold to >800-fold improvement in neutralizing antibody titers.

Example 7

($CuCl_2/H_2O_2$-Based Oxidation Demonstrated Improved Antigenicity with Influenza Virus Given the positive results observed across two virus families (Togaviridae and Flaviviridae), an additional virus family was chosen to test using this new inactivation platform.

As shown in this working example, inactivation of Influenza A virus (family Orthomyxoviridae) was tested using a standard 3% $H_2O_2$ approach, ultraviolet inactivation, or the optimized $CuCl_2/H_2O_2$ system (0.002% $H_2O_2$ and 1 µM $CuCl_2$). To assess antigenicity, a hemagglutination activity (HA) titration assay was used. Influenza viruses naturally agglutinate red blood cells, and maintenance of this activity throughout inactivation is considered key to the immunogenicity of the final vaccine product. As shown in FIG. 10, Applicants' $CuCl_2/H_2O_2$ system maintained HA titers similar to that observed for live, untreated antigen.

Specifically, FIG. 10 shows that $CuCl_2/H_2O_2$-based virus inactivation maintained influenza hemagglutination activity better than $H_2O_2$ alone. Purified influenza A/PR/8/34 (H1N1) was inactivated with $H_2O_2$ (3% for 2 hours, room temperature) $CuCl_2/H_2O_2$ (1 µM $CuCl_2$, 0.002% $H_2O_2$ for 20 hours, room temperature), ultraviolet light (UV, 10 joules) or left untreated (Live). Following inactivation, antigen preparations were directly tested for hemagglutination (HA) activity. Antigen preparations were scored by the lowest antigen concentration that still demonstrated full HA activity, and the reciprocal of this concentration was graphed. $CuCl_2/H_2O_2$ maintained protein function (i.e., hemagglutination activity) at levels that were indistinguishable from live influenza.

By comparison, UV inactivation reduced HA activity to a negligible level. The in vivo consequence of this HA destruction can be seen in FIG. 11, with the $CuCl_2/H_2O_2$ inducing robust protective serum antibody hemagglutinin inhibition (HAI) titers, while UV-treated antigen induced no functional antibodies in mice and minimal protection against lethal challenge.

Specifically, FIG. 11 shows that $CuCl_2/H_2O_2$ inactivated influenza induced robust hemagglutination inhibition titers and protected against lethal challenge. Purified influenza A/PR/8/34 (H1N1) was inactivated with $H_2O_2$ (3% for 2 hours, room temperature), $CuCl_2/H_2O_2$ (1 µM $CuCl_2$, 0.002% $H_2O_2$ for 20 hours, room temperature) or ultraviolet light (UV, 10 joules), with complete inactivation confirmed through focus forming assay viability testing. Following inactivation, antigen preparations were normalized by protein content and formulated with 0.10% aluminum hydroxide. Adult female BALB/c mice were immunized subcutaneously with 5 µg of vaccine.

Figures 11A, 11B:
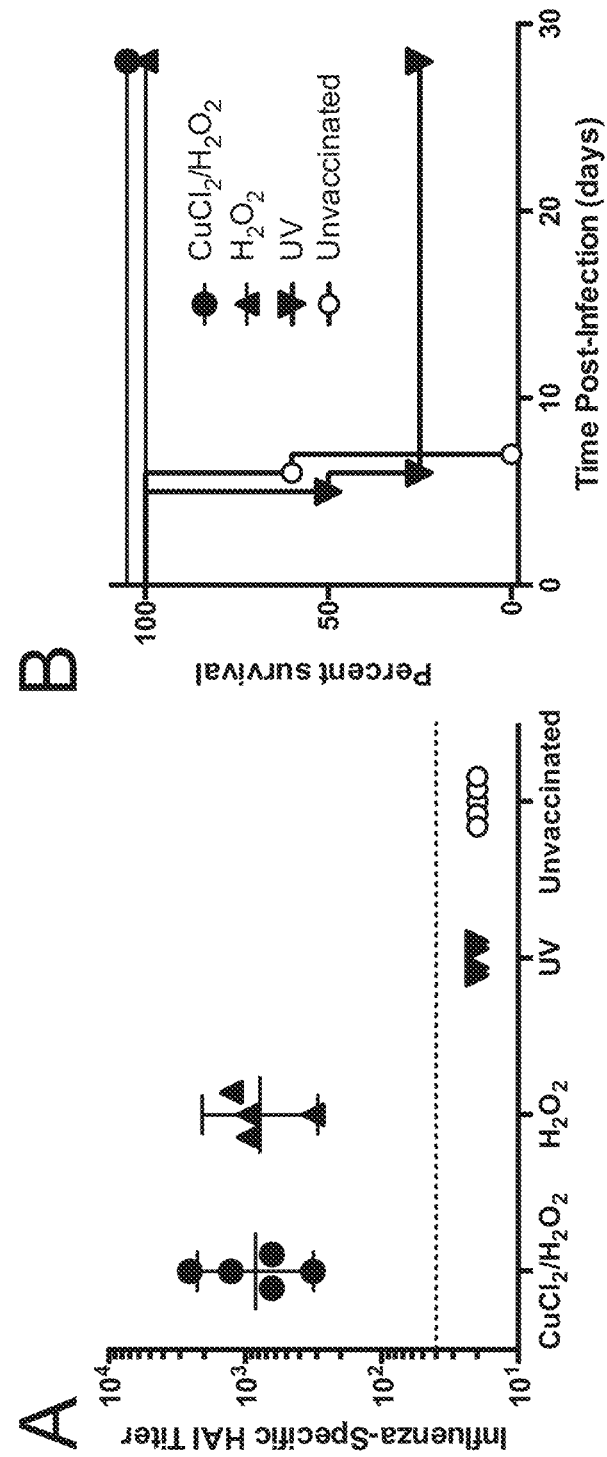
FIGS. 11A and 11B show, according to particular aspects, that $CuCl_2$/$H_2O_2$ inactivated influenza induces robust hemagglutination inhibition titers and protects against lethal challenge.

FIG. 11A shows that serum influenza-specific hemagglutinin inhibition (HAI) titers were determined for animals at two months post-vaccination. Results from unvaccinated control mice are shown for comparison. The limit of detection (LOD) for the assay is indicated by the dashed line.

FIG. 11B shows that at two months post-immunization, mice were challenged intranasally with $6 \times 10^4$ $EID_{50}$ of live influenza (A/PR/8/34 ($H_1N_1$), 20 $LD_{50}$) and followed daily for changes in body weight. Any animals reaching ≤75% of initial starting weight were humanely euthanized.

Mice vaccinated with $CuCl_2/H_2O_2$-inactivated virus or $H_2O_2$-inactivated virus showed highly significant protection following *influenzae* challenge (P=0.0031 and P=0.015, respectively). Whereas mice vaccinated with UV-inactivated virus demonstrated no significant protection (P=0.25).

Example 8

(Multiple Transition Metals were Successfully Used in the Dual-Oxidation Approach to Vaccine Antigen Development)

$Cu^{2+}$ (in the form of $CuCl_2$) was the initial metal tested in the dual-oxidation vaccine antigen development studies described for CHIKV, DENV, YFV and influenza virus. However, as described above, Applicants determined that other metals also have the potential to function in a similar manner.

As shown in this example using DENV3 as a model virus, inactivation studies consisting of $CuCl_2$ ($Cu^{2+}$), $FeCl_3$ ($Fe^{3+}$) or CsCl ($Cs^+$) and dilutions of $H_2O_2$ were tested for their potential in the development of vaccine antigen.

As shown in FIGS. 12A-C, all three metals provided conditions that maintained high levels of antigenicity while demonstrating complete virus inactivation.

Specifically, FIGS. 12A-C show a comparison of redox-active metals for dual oxidation-based virus inactivation. Purified DENV3 was treated with a range of $H_2O_2$ concentrations as indicated (20 hours, room temperature) in the presence of increasing concentrations of $CuCl_2$ (FIG. 12A), $FeCl_3$ (FIG. 12 B) and CsCl (FIG. 12C). Following treatment, the maintenance of neutralizing antibody binding sites (i.e., antigenicity) was measured using a DENV-specific sandwich ELISA comprised of two neutralizing monoclonal antibodies specific for the DENV envelope protein. ELISA values are expressed as a percentage of the live virus control. Following treatment, material was also tested for live DENV3 using a standard plaque forming unit (PFU) assay. Successful conditions that demonstrated no detectable live virus (<50 PFU/mL) are indicated by an asterisk (and where "N.T." is not tested).

All three metals provided conditions that maintained high levels of antigenicity while demonstrating complete virus inactivation.

Example 9

(Combinations of Transition Metals Demonstrated Synergy in the Dual-Oxidation Vaccine System)

As shown above in FIG. 12 and working example 8, different metals can be used in combination to enhance $H_2O_2$ inactivation of viruses.

As shown in this working example, to investigate potential synergistic effects, DENV3 model virus was inactivated with combinations of $CuCl_2$ ($Cu^{2+}$) and $FeCl_3$ ($Fe^{3+}$) at a set amount of $H_2O_2$ (0.01%). A number of $CuCl_2/FeCl_3$ conditions provided full inactivation while maintaining good antigenicity, demonstrating that using multiple metals in the same inactivation condition is feasible (FIG. 13). Indeed, at $CuCl_2$ concentrations of 0.05 µM and 0.10 µM, increasing $FeCl_3$ concentrations enhanced antigenicity, indicating synergy with these two metals.

Specifically, FIG. 13 shows that combinations of metals can achieve complete inactivation while maintaining good antigenicity. Purified DENV3 was treated with $H_2O_2$ (0.01%) and the indicated range of $CuCl_2$ and $FeCl_3$ concentrations. Following treatment, antigen was tested with a DENV-specific sandwich ELISA comprised of two neutralizing monoclonal antibodies specific for the envelope structural protein. ELISA values are expressed as a percentage of the live virus control. Following treatment, material was also tested for live DENV3 using a standard plaque forming unit (PFU) assay. Successful conditions that demonstrated no detectable live virus (<50 PFU/mL) are indicated by an asterisk. At $CuCl_2$ concentrations of 0.05 UM and 0.10 µM, increasing $FeCl_3$ concentrations enhanced antigenicity, indicating synergy with these two metals.

Example 10

(Dual Oxidation was Used to Provide Optimized Inactivation of *Campylobacter* for Improved Maintenance of Bacterial Morphology)

As shown in this working example, *Campylobacter* are small corkscrew-shaped bacteria that are typically ~0.2 µm in diameter and ~2-8 µm in length (FIG. 14A).

Following inactivation with a standard 3% $H_2O_2$ solution for 5 hours at room temperature, the bacteria were substantially damaged with clear changes in morphology, including loss of gross cellular structure and substantial clumping (FIG. 14B). However, upon optimization of a dual-oxidation approach using 0.01% $H_2O_2$ and 2 µM $CuCl_2$, Applicants surprisingly found that dual oxidation could completely inactivate the bacteria while maintaining excellent bacterial morphology throughout the treatment period with microbes that remained indistinguishable from the untreated controls (FIG. 14C).

Specifically, FIGS. 14A-14C show optimized inactivation of *Campylobacter* for improved maintenance of bacterial morphology.

In FIG. 14A, *C. coli* was grown, purified and left untreated.

In FIG. 14B, *C. coli* was grown, purified and inactivated with a high but destructive concentration of $H_2O_2$ (3% $H_2O_2$ for 5 hrs).

In FIG. 14C, *C. coli* was grown, purified and inactivated with 2 µM $CuCl_2$ and 0.01% $H_2O_2$. Data shows samples from each condition that were applied to slides and stained with Gram safranin.

In addition to retained structure, a critical parameter for preparing an inactivated whole-cell vaccine is to ensure complete microbe inactivation. Using the optimal conditions described above, inactivation kinetic studies were performed. As shown in FIG. 15, *C. coli* demonstrated rapid inactivation, with a decay rate half-life of ($T_{1/2}$) of ~15 minutes.

Specifically, FIG. 15 shows that exposure to an optimized $CuCl_2/H_2O_2$ formula results in rapid inactivation of *Campylobacter*. Purified preparations of *C. coli* were treated with an optimized $CuCl_2/H_2O_2$ formula and buffer condition, or mock inactivated (no $CuCl_2/H_2O_2$). Samples were taken at the indicated points and tested for viable *Campylobacter*. Open symbols indicate the absence of live bacteria. The dashed line shows the limit of detection. These kinetics indicate >20 logs of inactivation during the full 20-hr inactivation period. Based on the bacterial titers in our pilot manufacturing lots (~$10^9$ CFU/mL) this level of inactivation provides a high safety margin during the manufacturing process (up to 100 million-fold theoretical excess inactivation) while still maintaining overall bacterial structure (FIG. 14C).

Example 11

(Dual Oxidation-*Campylobacter* Vaccination Provides Protective Immunity in Rhesus Macaques)

As shown in this working example, Applicants determined vaccine efficacy through the monitoring of *Campylobacter* culture-confirmed enteric disease rates in 60 $CuCl_2/H_2O_2$-*C. coli*-immunized rhesus macaques as compared to unvaccinated control animals.

For this study, animals were vaccinated intramuscularly with the $CuCl_2/H_2O_2$-*C. coli* vaccine candidate (inactivated using 0.01% $H_2O_2$ and 2 µM $CuCl_2$), with a booster dose administered 6-months later. Vaccinated groups were selected based on prior disease history, with preference given to groups that had historically high incidence rates of *Campylobacter* infection. This approach provided increased robustness in evaluating protective efficacy. All adults/juveniles (n=59) received a 40-µg alum-adjuvanted dose, with 2 small infants (<2 Kg body weight) receiving a half-dose (20-µg). According to protocol, any animal diagnosed with *Campylobacter*-associated diarrhea during the first 14 days after vaccination would be excluded since vaccine-mediated protection would be unlikely to occur during this early period. One adult animal was excluded from the study due to *Campylobacter*-associated diarrhea on the day after vaccination. Serum samples were collected from all remaining vaccinated animals (n=59) at day 0 and at 6 months after primary vaccination at which time the animals received a booster dose of vaccine.

Figures 16A, 16B, 16C:
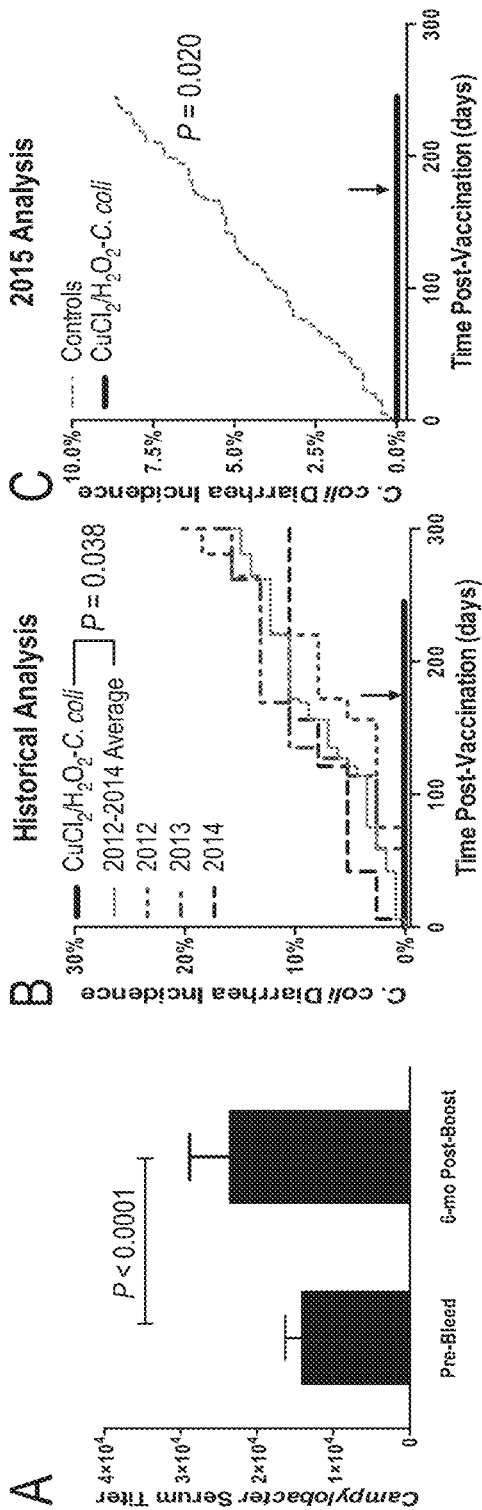
FIGS. 16A, 16B, and 16C show, according to particular aspects, that $CuCl_2$/$H_2O_2$-*C. coli* is immunogenic and protects rhesus macaques (RM) against naturally acquired *Campylobacter* infection.

Following primary vaccination, we observed a significant increase in *Campylobacter*-specific serum antibody titers (FIG. 16A, P<0.001) in addition to protection against *Campylobacter*-associated diarrheal disease in comparison with prior years within the same shelter group (FIG. 16B, P=0.038) or in comparison with other shelter groups during the 2015 *Campylobacter* season (FIG. 16C, P=0.020). The health of NHP is monitored daily and cases of diarrheal disease are documented in a searchable central database. Diarrhea incidence was monitored in the vaccinated cohort and compared to approximately 1,000 unvaccinated control animals in other similar shelter groups. Fecal samples were collected from any animal experiencing a diarrheal episode and tested for *C. coli, C. jejuni,* and *Shigella* spp. since these represent the main enteric pathogens associated with diarrhea among the animals.

Specifically, FIGS. 16A-16C show that dual oxidation-*C. coli* is immunogenic and protects RM against naturally acquired *Campylobacter* infection.

In FIG. 16A, serum samples were collected from animals just prior to vaccination, or 6 months following primary immunization and assayed for *Campylobacter*-specific antibody responses using an optimized, whole-cell ELISA, with all serum samples pre-adsorbed against *Shigella* (a gram-negative enteric bacteria) to reduce non-specific binding. Significance testing was performed using a paired student's t-test.

Subsequent to vaccination, animals were followed for 8 months for *C. coli*-associated diarrhea, and compared (FIG. 16B) to prior year diarrhea rates within the same shelter, or compared (FIG. 16C) to the rates of diarrheal incidence in other concurrent shelters (~1,000 control animals) monitored in 2015. Black arrows indicate the time of booster vaccination.

Interim analysis at 6 months after primary vaccination demonstrated no cases of *C. coli* or *C. jejuni*-associated diarrhea in the vaccinated group versus 76 cases of *Campylobacter*-associated diarrhea among the unvaccinated animals, representing a statistically significant protective effect against *Campylobacter* culture-positive diarrheal disease (P=0.035) after a single vaccination.

Since nearly all human vaccines require at least two doses for optimal protective efficacy and the durability of immunological memory is often improved following booster vaccination, a conservative approach was followed by administering a booster vaccination at the 6 month time point followed by continued monitoring of the incidence of diarrheal disease among the NHP. At 250 days after primary vaccination, more cases of *Campylobacter*-associated enteric disease had continued to accrue among the unvaccinated population (reaching 8.7% or a total of 92 animals) whereas none of the animals (0/59) in the vaccinated cohort showed signs of disease and the statistical significance between the two groups increased to P=0.020.

Example 12

(Methisazone Enhanced the Rate of Both Single and Dual Oxidation-Based Virus Inactivation)

As shown in this working example, Applicants determined that methisazone enhanced the rate of both single and dual oxidation-based virus inactivation. As shown in FIGS. 17A-C, the addition of methisazone was able to substantially increase the rate of dual-oxidation-based inactivation for vaccinia virus (VV, DNA genome) as well as dengue virus serotype 4 (DENV4, RNA genome) and chikungunya virus (CHIKV, RNA genome).

Further, while methisazone alone had a minimal impact on virus inactivation (FIGS. 17B & 17C), methisazone and $H_2O_2$ together (even in the absence of copper) demonstrated a synergistic enhancement for virus inactivation.

Specifically, FIGS. 17A, 17B, and 17C show, according to particular aspects, that methisazone enhanced the rate of both single and dual oxidation-based virus inactivation. (A) Vaccinia virus (PBS, pH=7.5), (B) dengue virus serotype 4 (DENV4, in 110 mM NaCl, 150 mM $NaPO_4$[pH=7.5], 2% D-sorbitol) and (C) Chikungunya virus (CHIKV, in PBS supplemented with 150 mM $NaPO_4$[pH=7.5]), were each treated with inactivation reagents as indicated in the figure. Concentrations for the different components were as follows: $H_2O_2$=0.004% (CHIKV) or 0.002% (DENV4 and VV); $CuCl_2$=1 µM (all viruses), methisazone (MZ)=10 µM (all viruses). The dotted line indicates the limit of detection (LOD).

Example 13

(Methisazone Enhanced the Rate of Dual Oxidation-Based Bacterial Inactivation)

As shown in this working example, Applicants determined that methisazone enhanced the rate of dual oxidation-based bacterial inactivation.

The results of working Example 12 were extended to bacteria (FIGS. 18A-C) where again the addition of methisazone to the dual-oxidation approach (e.g., $H_2O_2/CuCl_2$) substantially enhanced inactivation rates for *Campylobacter coli* (an exemplary gram-negative bacteria), *Listeria monocytogenes* (an exemplary gram-positive bacteria) and *Shigella dysenteriae* (an exemplary gram-negative bacteria).

Figures 18A, 18B, 18C:
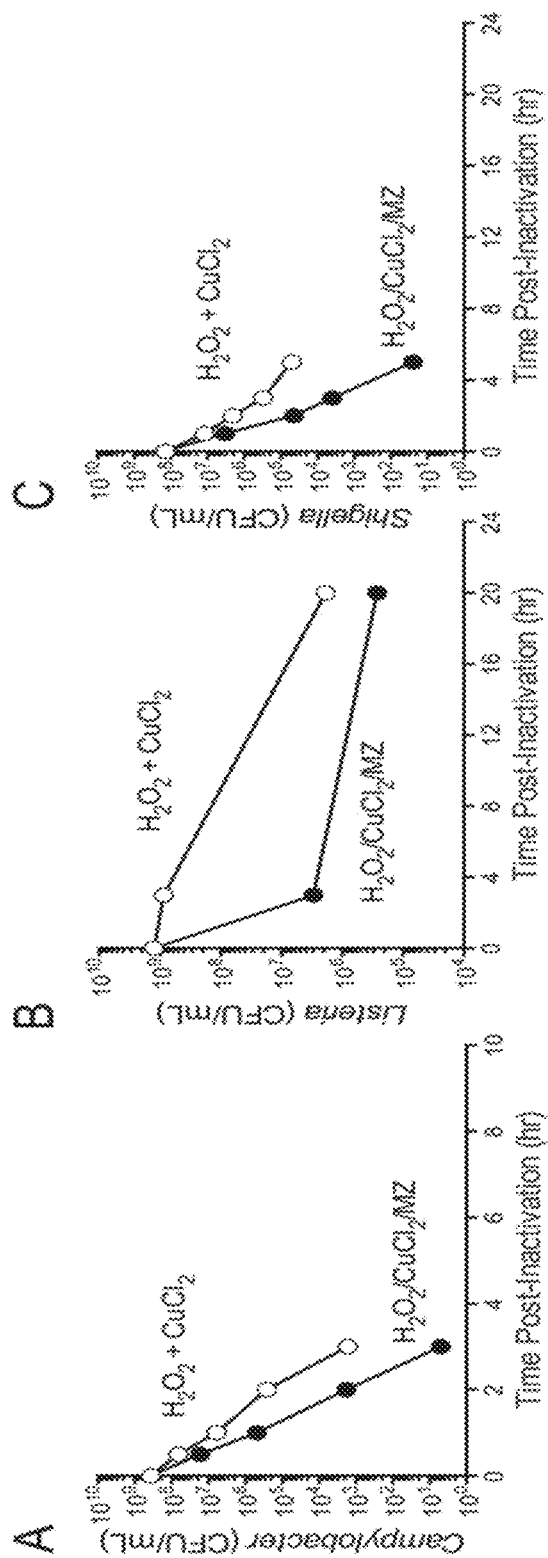
FIGS. 18A, 18B, and 18C show, according to particular aspects, that methisazone enhanced the rate of dual oxidation-based bacterial inactivation.

Specifically, FIGS. 18A, 18B, and 18C show, according to particular aspects, that methisazone enhanced the rate of dual oxidation-based bacterial inactivation. (A) *Campylobacter coli* (B) *Listeria monocytogenes* and (C) *Shigella dysenteriae* were buffer exchanged into 10 mM NaCl, 150 mM NaPO+[pH=7.5] and 2% D-sorbitol and treated with inactivation components as indicated in each panel. Viability post-inactivation, as determined through colony forming units per mL (CFU/mL), was followed over time. Concentrations of inactivation components were optimized for each type of bacteria as follows: *C. coli*: $H_2O_2$=0.01%, $CuCl_2$=2 M, methisazone (MZ)=20 µM; *L. monocytogenes*: $H_2O_2$=0.10%, $CuCl_2$=10 µM, methisazone (MZ)=100 µM; *S. dysenteriae*: $H_2O_2$=0.10%, $CuCl_2$=10 µM, MZ=100 µM; Open symbols represent conditions without MZ, while closed symbols indicate the addition of MZ. The limit of detection was 10 CFU/mL.

Example 14

(Methisazone Enhanced Inactivation Rates while Maintaining Antigenicity During Dual Oxidation-Based Viral Inactivation)

As shown in this working example, Applicants determined that methisazone enhanced inactivation rates while maintaining antigenicity during dual oxidation-based virus inactivation. To assess the impact of methisazone on antigenicity during inactivation, the exemplary model viruses CHIKV and DENV4 were treated with multiple inactivation approaches: high concentration $H_2O_2$ (single oxidation system), dual-oxidation (as described herein), or dual-oxidation with methisazone. As shown by the ELISA data in FIG. 19A (Chikungunya virus (CHIKV)) and 19B (dengue virus serotype 4 (DENV4)), the addition of methisazone to the dual-oxidation approach maintained or significantly improved antigenicity by reducing damage to neutralizing epitopes, while increasing the rate of inactivation by approximately 10- to 20-fold.

Figures 19A, 19B:
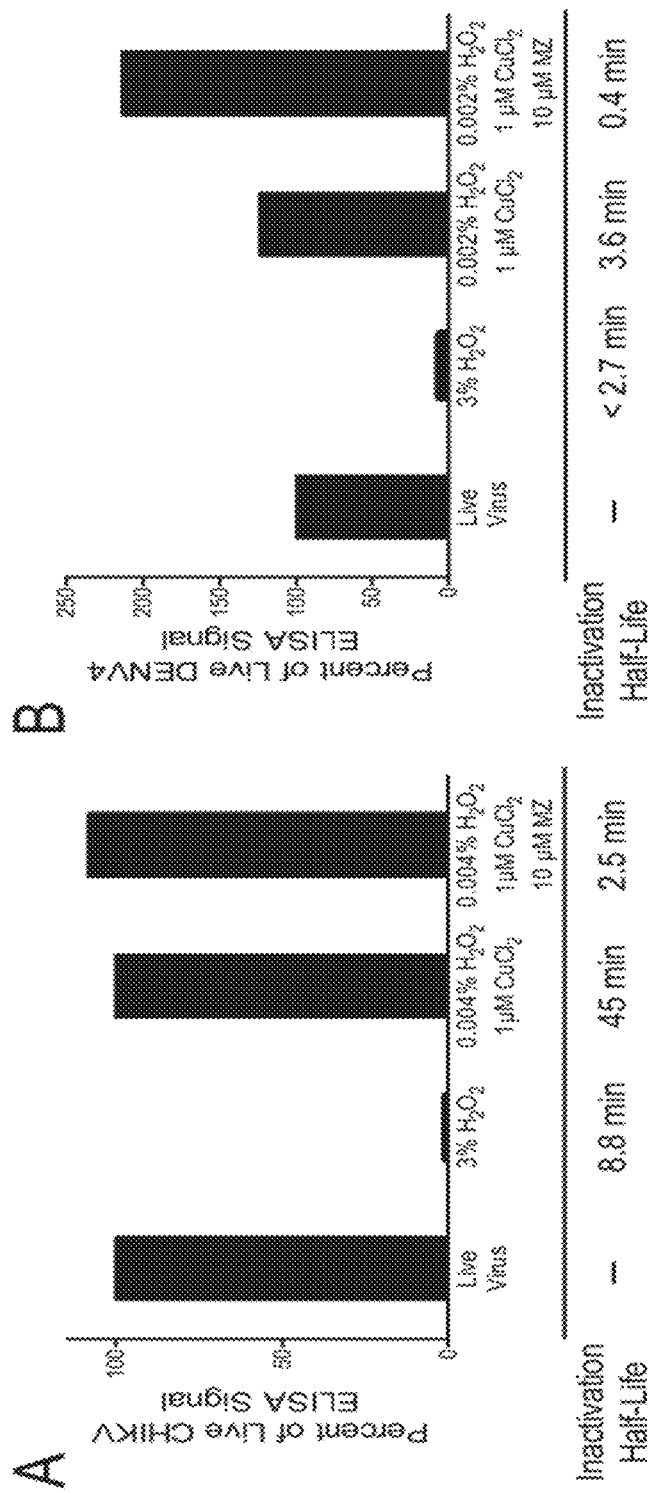
FIGS. 19A and 19B show, according to particular aspects, that methisazone enhanced inactivation rates while maintaining antigenicity during dual oxidation-based viral inactivation.

Specifically, FIGS. 19A and 19B show, according to particular aspects, that methisazone enhanced inactivation rates while maintaining antigenicity during dual oxidation-based virus inactivation. Chikungunya virus (CHIKV, in PBS supplemented with 150 mM $NaPO_4$[pH=7.5]) and dengue virus serotype 4 (DENV4, in 110 mM NaCl, 150 mM $NaPO_4$[pH=7.5], 2% D-sorbitol) were each treated for 20 hours at room temperature with the inactivation components indicated in the figure. Following virus treatment, antigen retention was tested with either (A) a CHIKV-specific sandwich ELISA comprised of two neutralizing monoclonal antibodies specific for the E1 and E2 structural proteins or (B) a DENV-specific sandwich ELISA comprised of two neutralizing monoclonal antibodies specific for the envelope structural protein. ELISA values indicate retained neutralizing epitopes and are expressed as a percentage of live virus controls. Both viruses were also treated with 3% $H_2O_2$ to show loss of neutralizing epitopes by a damaging inactivation approach. Inactivation half-lives for each condition are shown.

Example 15

(Chemical Analogs of Methisazone, or Methisazone Functional Groups Substructures or Combinations Thereof, Enhanced Inactivation and Maintenance of Antigenicity During Dual Oxidation-Based Viral Inactivation)

As shown in this working example, Applicants determined that chemical analogs of methisazone, or methisazone functional groups/substructures or combinations thereof, enhanced inactivation and maintenance of antigenicity during dual oxidation-based viral inactivation.

As mentioned above, methisazone is a compound originally developed as an in vivo antiviral agent. We tested several related compounds to determine if they provided similar enhancements to pathogen inactivation for vaccine development (FIGS. 20A-C). As shown with the exemplary model virus DENV4, several of these compounds, such as isatin β-thiosemicarbazone and N-propylisatin β-thiosemicarbazone, demonstrated results similar to methisazone including enhanced rates of inactivation while maintaining superior antigenicity in the dual-oxidation system. Interestingly, when using just the thiosemicarbazide moiety, we still observed enhancement of inactivation and superior antigenicity, whereas isatin or semicarbazide do not appear to increase the rate of inactivation, but still demonstrate protection of protein antigens from oxidative damage during inactivation. To explore if the separate major components (functional groups/substructures) of methisazone-related compounds could be combined in order to recapitulate optimal inactivation, we tested mixtures of isatin+thiosemicarbazide or isatin+semicarbazide. While isatin+semicarbazide still demonstrated antigen protection, there was no enhancement of virus inactivation. By contrast, isatin+thiosemicarbazide resulted in both rapid inactivation (more rapid than either component alone) as well as greatly increased antigenicity.

Specifically, FIGS. 20A, 20B, and 20C show, according to particular aspects, that chemical analogs of methisazone, or methisazone functional groups/substructures or combinations thereof, enhanced inactivation and maintenance of antigenicity during dual oxidation-based viral inactivation. (A) Related chemical compounds of the isatin β-thiosemicarbazone class are shown. (B) Dengue virus serotype 4 (DENV4, in 110 mM NaCl, 150 mM NaPO$_4$[pH=7.5], 2% D-sorbitol) was treated with dual oxidation components as indicated in each panel (H$_2$O$_2$=0.01%, CuCl$_2$=1 µM) in the absence or presence of different MZ-like compounds, with each compound used at a concentration of 10 µM. To assess inactivation, viable virus was tested by plaque assay at 1 hr post-inactivation. The dotted line indicates the limit of detection. (C) To quantitate antigenicity, a DENV-specific sandwich ELISA comprised of two neutralizing monoclonal antibodies specific for the envelope structural protein was performed at 20 hrs post-inactivation. ELISA values indicate retained neutralizing epitopes and are expressed as a percentage of live virus controls.

Example 16

(Increasing Levels of Methisazone Relative to the Transition Metal Component of the Dual Oxidation System Improved the Antigenicity and Inactivation Profile of the Dual Oxidation System)

As shown in this working example, Applicants determined that increasing levels of methisazone relative to the transition metal component of the dual oxidation system improved the antigenicity and inactivation profile of the dual oxidation system.

Figure 21:
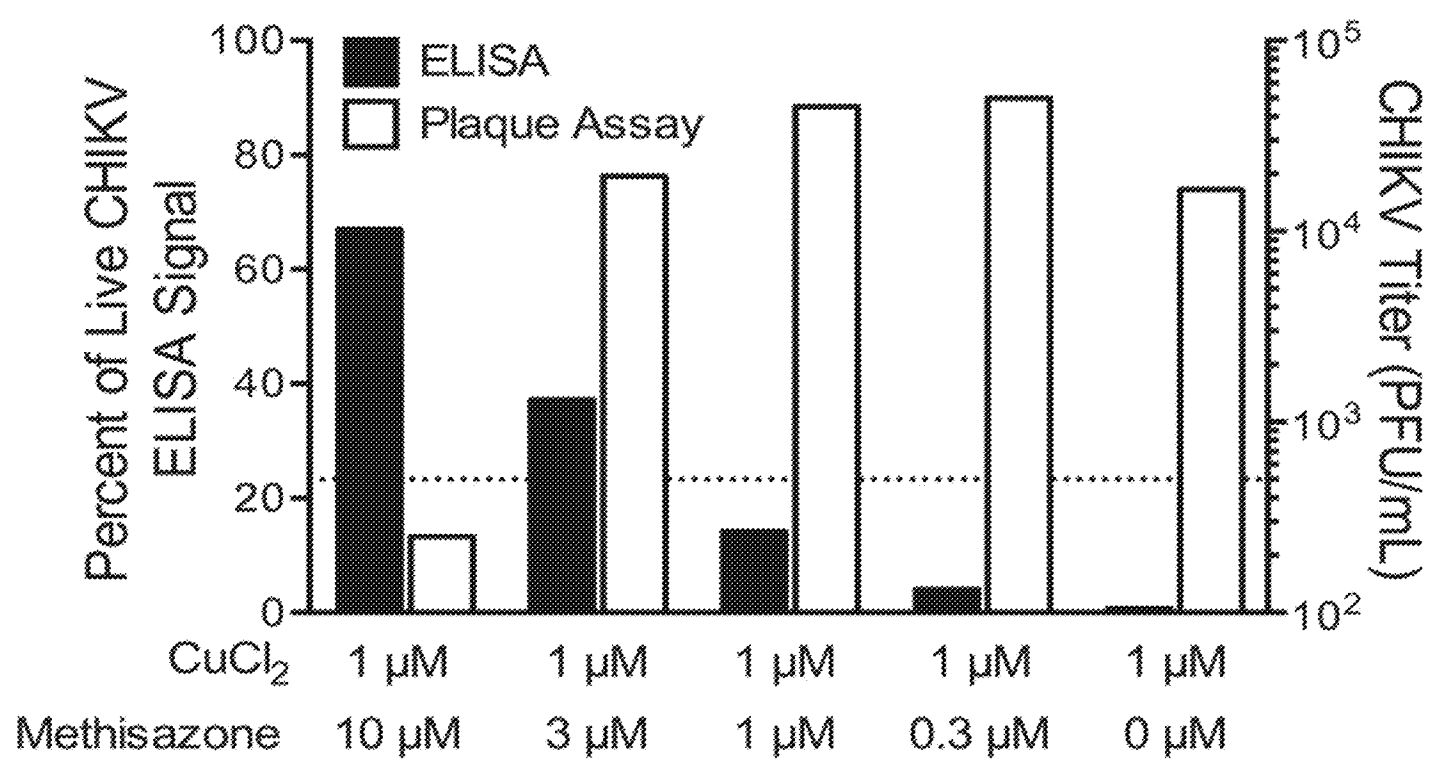

We examined the impact of relative concentrations of methisazone and the transition metal in the dual-oxidation system (FIG. 21). We found that increasing methisazone concentrations relative to the transition metal demonstrated concomitant improvements in both retained antigenicity and increased virus inactivation rates, with a preferred molar ratio of 10:1 (methisazone:transition metal).

Specifically, FIG. 21 shows, according to particular aspects, that increasing levels of methisazone relative to the transition metal component of the dual oxidation system improved the antigenicity and inactivation profile of the dual oxidation system. Chikungunya virus (CHIKV, in PBS supplemented with 150 mM NaPO$_4$[pH=7.5]) was treated with H$_2$O$_2$ (0.02%) and CuCl$_2$ (1 µM) at room temperature in the presence of decreasing concentrations of methisazone. Following treatment, virus was tested by plaque assay at 1 hr to assess inactivation, and tested for retained antigenicity at 20 hrs using a CHIKV-specific sandwich ELISA comprised of two neutralizing monoclonal antibodies specific for the E1 and E2 structural proteins. The limit of detection for the plaque assay is indicated by the dotted line.

References supporting the working examples and incorporated by reference herein for their respective teachings:

Sagripanti, J. L., L. B. Routson, and C. D. Lytle, *Virus inactivation by copper or iron ions alone and in the presence of peroxide*. Appl Environ Microbiol, 1993. 59(12): p. 4374-6.

Nieto-Juarez, J. I., et al., *Inactivation of MS2 coliphage in Fenton and Fenton-like systems: role of transition metals, hydrogen peroxide and sunlight*. Environ Sci Technol, 2010. 44(9): p. 3351-6.

Barbusiński, K., *Fenton Reaction—Controversy concerning the chemistry*. Ecological Chemistry and Engineering, 2009. 16(3): p. 347-358.

Sagripanti, J. L., *Metal-based formulations with high microbicidal activity*. Appl Environ Microbiol, 1992. 58(9): p. 3157-62.

McClatchey, K. D., *Clinical laboratory medicine*. 2nd ed. 2002, Philadelphia: Lippincott Wiliams & Wilkins. xiv, 1693 p.

Lippincott Williams & Wilkins., *Nursing. Deciphering diagnostic tests*. Nursing. 2008, Philadelphia, PA: Wolters Kluwer/Lippincott Williams & Wilkins. vii, 664 p.

Sagripanti, J. L., et al., *Mechanism of copper-mediated inactivation of herpes simplex virus*. Antimicrob Agents Chemother, 1997. 41(4): p. 812-7.

Sagripanti, J. L., P. L. Goering, and A. Lamanna, *Interaction of copper with DNA and antagonism by other metals*. Toxicol Appl Pharmacol, 1991. 110(3): p. 477-85.

Toyokuni, S. and J. L. Sagripanti, *Association between 8-hydroxy-2'-deoxyguanosine formation and DNA strand breaks mediated by copper and iron*, in *Free Radic Biol Med*. 1996: United States. p. 859-64.

Nguyen, T. T., et al., *Microbial inactivation by cupric ion in combination with H2O2: role of reactive oxidants*. Environ Sci Technol, 2013. 47(23): p. 13661-7.

Thompson R L, Minton S A, Jr., Officer J E, Hitchings G H. Effect of heterocyclic and other thiosemicarbazones on vaccinia infection in the mouse. J Immunol. 1953; 70:229-34.

Bauer D J. The antiviral and synergic actions of isatin thiosemicarbazone and certain phenoxypyrimidines in vaccinia infection in mice. Br J Exp Pathol. 1955; 36:105-14.

Bauer D J. Clinical experience with the antiviral drug marboran (1-methylisatin 3-thiosemicarbazone). Ann N Y Acad Sci. 1965; 130:110-7.

Bauer D J, Stvincent L, Kempe C H, Downie A W. Prophylactic Treatment of Small Pox Contacts with N-Methylisatin Beta-Thiosemicarbazone (Compound 33t57, Marboran). Lancet. 1963; 2:494-6.

Fox M P, Bopp L H, Pfau C J. Contact inactivation of RNA and DNA viruses by N-methyl isatin beta-thiosemicarbazone and CuSO4. Ann N Y Acad Sci. 1977; 284:533-43.

Logan J C, Fox M P, Morgan J H, Makohon A M, Pfau C J. *Arenavirus* inactivation on contact with N-substituted isatin beta-thiosemicarbazones and certain cations. J Gen Virol. 1975; 28:271-83.

Mikelens P E, Woodson B A, Levinson W E. Association of nucleic acids with complexes of N-methyl isatin-beta-thiosemicarbazone and copper. Biochem Pharmacol. 1976; 25:821-7. Rohde W, Shafer R, Idriss J, Levinson W. Binding of N-methyl isatin beta-thiosemicarbazone-copper complexes to proteins and nucleic acids. J Inorg Biochem. 1979; 10:183-94.

Pakravan P, Masoudian S. Study on the Interaction between Isatin-beta-Thiosemicarbazone and Calf Thymus DNA by Spectroscopic Techniques. Iran J Pharm Res. 2015; 14:111-23.

What is claimed is:

1. A method for producing an immunogenic vaccine composition comprising an inactivated pathogen, the method comprising: contacting a pathogen having an RNA or DNA genome with a Fenton reagent, comprising hydrogen peroxide in combination with a transition metal selected from Cu and/or Fe, and one or more compound(s) of formula I, II, III, IV, or V, in an amount and for a time-period sufficient for the reagent and the compound(s) to render the pathogen noninfectious while retaining pathogen immunogenicity, wherein for formula I:

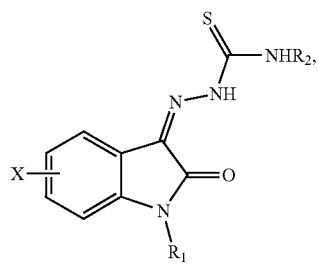

$R_1$ is independently H or C1-C4 alkyl optionally substituted with —OH;

$R_2$ is independently H, C1-C2 alkyl optionally substituted with —OH, or with aryl; and X is independently H or halogen; and pharmaceutically acceptable salts thereof, wherein for formula II:

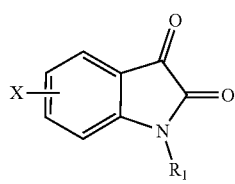

$R_1$ is H or C1-C4 alkyl optionally substituted with —OH; and

X is independently H or halogen; and salts, including pharmaceutically acceptable salts thereof;

wherein for formula III:

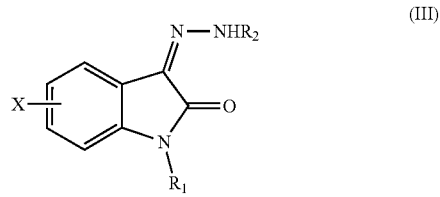

$R_1$ is H or C1-C4 alkyl optionally substituted with —OH;
X is independently H or halogen; and
$R_2$ is independently H, C1-C2 alkyl optionally substituted with —OH, or with aryl; and salts, including pharmaceutically acceptable salts thereof; and wherein for formulas IV and V:

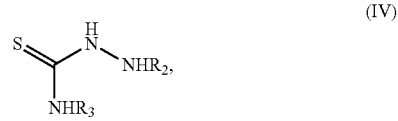

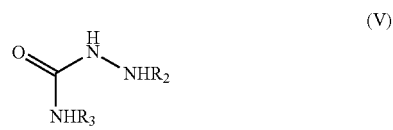

$R_2$ and $R_3$ are independently H, C1-C2 alkyl optionally substituted with —OH, or with aryl; and
salts, including pharmaceutically acceptable salts thereof; and combinations thereof.

2. The method of claim 1, further comprising verifying immunogenicity of the noninfectious pathogen using pathogen-specific antibody, B cell or T cell immunoassays, agglutination assays, or antigen-binding assays.

3. The method of claim 1, wherein a mixture of different transition metal ions are used in combination with hydrogen peroxide.

4. The method of claim 1, wherein the pathogen is a virus, or a bacterium.

5. The method of claim 4, wherein the pathogen is a virus, or a combination of different viruses.

6. The method of claim 5, wherein the virus is from Family Togaviridae, Flaviviridae, Poxviridae, or Orthomyxoviridae.

7. The method of claim 5, wherein the virus is from Family: Togaviridae, Genus: *Alphavirus*, Family: Flaviviridae, Genus: *Flavivirus*, Family: Poxviridae, Genus *Orthopoxvirus*, or Family: Orthomyxoviridae, Genus: *Influenzavirus*.

8. The method of claim 7, wherein the virus is chikungunya virus (CHIKV, Family: Togaviridae, Genus: *Alphavirus*), dengue virus serotypes 1-4 and yellow fever virus (DENV 1-4, YFV, Family: Flaviviridae, Genus: *Flavivirus*), vaccinia virus (VV, Family: Poxviridae, Genus: *Orthopoxvirus*), or influenza virus (Family: Orthomyxoviridae, Genus: *Influenzavirus*).

9. The method of claim 4, wherein the pathogen is a bacterium, or a combination of different bacteria.

10. The method of claim 9, wherein the bacterium is *Campylobacter* spp.

11. The method of claim 10, wherein the *Campylobacter* is *C. coli* or *C. jejuni*.

12. The method of claim 9, wherein the bacterium is *Shigella* spp.

13. The method of claim 9, wherein the bacterium is *Listeria* spp.

14. The method of claim 1, wherein the pathogen is isolated or purified prior to contacting with the Fenton reagent and the one or more compound(s).

15. The method of claim 1, wherein contacting the pathogen comprises contacting the pathogen with the Fenton reagent and the compound having formula I, wherein:
X and $R_2$ are H; and
$R_1$ is H (isatin β-thiosemicarbazone), —$CH_3$ (N-methyl-isatin β-thiosemicarbazone (methisazone)), or propyl (N-propyl-isatin β-thiosemicarbazone).

16. The method of claim 15, wherein $R_1$ is —$CH_3$ (N-methyl-isatin β-thiosemicarbazone (methisazone))

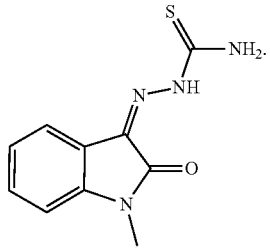

(VII)

17. The method of claim 1, wherein X of formula (II) is H, and $R_1$ of formula (II) is H (isatin), —$CH_3$ (N-methyl-isatin), or propyl (N-propyl-isatin); wherein X, $R_1$, and $R_2$ of formula (III) are H (indole, 2,3-dione, 3-hydrazone); wherein $R_2$ and $R_3$ of formula (IV) are H (thiosemicarbazide); and wherein $R_2$ and $R_3$ of formula (V) are H (semicarbazide).

18. The method of claim 1, wherein contacting the pathogen comprises contacting the pathogen with the Fenton reagent, thiosemicarbazide, and a compound having formula VI:

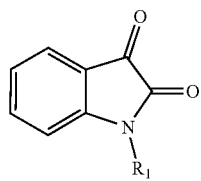

(VI)

wherein $R_1$ is H or C1-C4 alkyl.

19. The method of claim 18, wherein $R_1$ is H (isatin), —$CH_3$ (N-methyl-isatin), or propyl (N-propyl-isatin).

20. The method of claim 18, wherein $R_1$ is H (isatin).

21. An immunogenic vaccine composition having an inactivated pathogen with an RNA or DNA genome, and produced by the method of claim 1, wherein the vaccine has an antigenicity and/or immunogenicity greater than that obtainable by inactivation of the pathogen using hydrogen peroxide alone.

22. The immunogenic vaccine composition of claim 21, wherein the inactivated pathogen retains one or more predominant antigenic epitopes of the biologically active pathogen suitable to elicit a pathogen-specific antibody, B cell or T cell response, or to reduce infection by the pathogen, or decrease symptoms that result from infection by the pathogen.

23. A method of eliciting an immune response against a pathogen, the method comprising administering an immunogenic vaccine composition having an inactivated pathogen according to claim 21 to a subject, thereby eliciting in the subject an immune response against the pathogen.

24. The immunogenic vaccine composition of claim 21, wherein the inactivated pathogen is a virus, or a combination of different viruses.

25. The immunogenic vaccine composition of claim 24, wherein the virus is from the Family Togaviridae, Flaviviridae, Poxviridae, or Orthomyxoviridae.

26. The immunogenic vaccine composition of claim 25, wherein the virus is from Family: Togaviridae, Genus: *Alphavirus*, Family: Flaviviridae, Genus: *Flavivirus*, Family: Poxviridae, Genus *Orthopoxvirus*, or Family: Orthomyxoviridae, Genus: *Influenzavirus*.

27. The immunogenic vaccine composition of claim 26, wherein the virus is chikungunya virus (CHIKV, Family: Togaviridae, Genus: *Alphavirus*), dengue virus serotypes 1-4 and yellow fever virus (DENV 1-4, YFV, Family: Flaviviridae, Genus: *Flavivirus*), vaccinia virus (VV, Family: Poxviridae, Genus: *Orthopoxvirus*), or influenza virus (Family: Orthomyxoviridae, Genus: *Influenzavirus*).

28. The immunogenic vaccine composition of claim 21, wherein the inactivated pathogen is a bacterium, or a combination of different bacteria.

29. The immunogenic vaccine composition of claim 28, wherein the bacterium is *Campylobacter* spp., *Shigella* spp., or *Listeria* spp., or combinations thereof.

30. The immunogenic vaccine composition of claim 29, wherein the bacterium is *Campylobacter* spp.

31. The immunogenic vaccine composition of claim 30, wherein the bacterium is *Campylobacter C. coli* and/or *C. jejuni*.

* * * * *